United States Patent
Venskus et al.

(10) Patent No.: US 10,174,291 B2
(45) Date of Patent: Jan. 8, 2019

(54) GENETICALLY STABLE ONCOLYTIC RNA VIRUS, METHOD OF MANUFACTURING AND USE THEREOF

(71) Applicant: DITESAN LTD., Riga, Latvia (LV)

(72) Inventors: Dite Venskus, Jelgava (LV); Ivars Kalvins, Riga (LV); Dace Pjanova, Riga (LV); Ramona Petrovska, Riga (LV); Jurgis Auzins, Olaine (LV)

(73) Assignee: Ditesan Ltd., Riga (LV)

( * ) Notice: Subject to any disclaimer, the term of this patent is extended or adjusted under 35 U.S.C. 154(b) by 0 days.

(21) Appl. No.: 14/904,837

(22) PCT Filed: Jul. 16, 2014

(86) PCT No.: PCT/EP2014/065277
§ 371 (c)(1),
(2) Date: Jan. 13, 2016

(87) PCT Pub. No.: WO2015/007788
PCT Pub. Date: Jan. 22, 2015

(65) Prior Publication Data
US 2016/0376562 A1 Dec. 29, 2016

(30) Foreign Application Priority Data

Jul. 16, 2013 (EP) .................................. 13176757

(51) Int. Cl.
*C12N 15/00* (2006.01)
*A61K 48/00* (2006.01)
*C12N 7/00* (2006.01)
*A01K 67/00* (2006.01)

(52) U.S. Cl.
CPC ...... *C12N 7/00* (2013.01); *C12N 2770/32321* (2013.01); *C12N 2770/32332* (2013.01)

(58) Field of Classification Search
CPC ............ C12N 7/00; C12N 2770/32321; C12N 2770/32332
See application file for complete search history.

(56) References Cited

FOREIGN PATENT DOCUMENTS

| EP | 1 537 872 | | 6/2005 |
|---|---|---|---|
| WO | WO 01/37866 | * | 5/2001 |
| WO | WO 2003/105875 | * | 12/2003 |
| WO | WO 2004/054613 | * | 7/2004 |

OTHER PUBLICATIONS

Chua et al. Comparison of the complete nucleotide seuences of echovirus 7 strain UMMC and the prototype (Wallace) strain demonstrates significant genetic drift over time. J. Gen. Vir. 82:2629-2639, 2001.*
Ferdats: "Mechanism of Immunomodulation in the anti-tumour effect of the ECHO-7 enterovirus" Experimental Oncology, Jan. 1989, 11(5):43-48.

* cited by examiner

*Primary Examiner* — Quang Nguyen
(74) *Attorney, Agent, or Firm* — Duane Morris LLP; Thomas J. Kowalski; Deborah L. Lu

(57) ABSTRACT

In a method for manufacturing a modified enterovirus of ECHO 7 type by modification of native ECHO 7 virus, isolated by a known method from human feces and identified by genome sequence, the modification is performed initially conducting the virus adaptation in cancer cells, attenuated by anti-cancer agent dacarbazine, further passaging the modified virus in human embryonal fibroblast culture, followed by propagation in human melanoma cells and further passaging in human embryonal fibroblast culture, that was treated by ribavirin, isolation and purification by known method. The modified virus is suitable for treating various tumours.

2 Claims, 11 Drawing Sheets
Specification includes a Sequence Listing.

FIG. 1

Comparison of genomes of the unmodified (native) virus and modified virus

N: Unmodified (native) virus
M: Modified virus

```
           1                                                            50
N      TTAAAACAGC CTGTGGGTTG TTCCCACCCA CAGGGCCCAC TGGGCGCTAG
M      .......... .......... .......... .......... ..........
           51                                                          100
N      CACACTGGTA TCACGGTACC TTTGTGCGCC TGTTTTATAT CCCCCTCCCC
M      .......... .......... C......... .........C. T.........
           101                                                         150
N      ACTGTAACTT AGAGAAATCA CATAAACGAT CAATAGAAGG CGCAGCACAC
M      .......... ...AG...G. .........G. ...C...TA. .T...T....
           151                                                         200
N      CAGCTGAGTC TTGACCAAGC ACTTCTGTTT CCCCGGACTG AGTATCAATA
M      ..A.....C. CC........ .........A ........C. ....A.....
           201                                                         250
N      GACTGCTCAC GCGGTTGAAG GAGAAAACGT TCGTTACCCG GCCAACTACT
M      .G......G. ....C..... .T........ .......... .....T....
           251                                                         300
N      TCGAGAAACC TAGTACCACC ATGAAAGTTG CGCAGTGTTT CGCTCAGCAC
M      .......... .......... .....G.... ......C... .....C....
           301                                                         350
N      AACCCCAGTG TAGATCAGGT CGATGAGTCA CCGCATTCCC CACGGGCGAC
M      .......... .......... .......... .....C.... ..........
           351                                                         400
N      CGTGGCGGTG GCTGCGTTGG CGGCCTGCCT ATGGGGCAAC CCATGGGACG
M      .......... ......C... .......... .......... ..........
           401                                                         450
N      CTTCAATACT GACATGGTGC GAAGAGTCTA TTGAGCTAGT TGGTAGTCCT
M      .......... .......... .......... ........A. ..........
           451                                                         500
N      CCGGCCCCTG AATGCGGCTA ATCCTAACTG CGGAGCAAGT GCCCACAAAC
M      .......... .......... .......... ...G...... ..........
           501                                                         550
N      CAGTGGGTAG CTTGTCGTAA CGGGCAACTC TGCAGCGGAA CCGACTACTT
M      ........G. .......... ....T...C. .......... ..........
           551                                                         600
N      TGGGTGTCCG TGTTTCCTTT TATTCTTATT CTGGCTGCTT ATGGTGACAA
M      .......... .......... .......... .......... ..........
           601                                                         650
N      TTGAGAGATT GTTACCATAT AGCTATTGGA TTGGCCATCC GGTGACTAAC
M      .......... ...R...... .......... ......R..T .....G....
           651                                                         700
N      AGAGCAATTA TATACCTCTT TGTTGGATTT ATACCACTTA ATTCCACTAA
M      .......C.. ....T..... .......... ........G. ..........G
           701                                                         750
N      TTACAACACT CTGCTACACA TTATTTACTT AAAACCAAGA AGATGGGAGC
M      .......... ........T. ......G... ...TA..... ..........
           751                                                         800
N      ACAAGTATCA ACACAAAAAA CTGGTGCACA TGAGACCGT TTGAGCGCTA
M      .........G ........G. .......... C......... ..........
           801                                                         850
N      ACGGAAGCTC CATCATTCAC TACACCAACA TCAATTACTA CAAAGATGCA
M      .....CA... T......... ..T....... ....C..... ..........
```

```
    851                                                900
N   GCATCCAACT CAGCCAACAG GCAAGACTTC ACCCAAGATC CAGGCAAATT
M   .......... .......... ...G..T... .....G.... ....T..G..
    901                                                950
N   CACCGAACCG GTCAAGGATA TCATGATCAA GTCAATGCCC GCCCTAAACT
M   ...T...... .......... .......... A..G...... ..........
    951                                               1000
N   CACCGACCGT GGAGGAGTGT GGGTACAGTG ATAGGGTGAG ATCCATAACG
M   .....T...C .........C ........C. .C........ ....C.....
    1001                                              1050
N   CTCGGCAACT CAACCATTAC CACTCAGGAG AGTGCAAATG TAGTTGTTGG
M   .......... .......... ......A..A ........C. ..........
    1051                                              1100
N   CTATGGCGGG TGGCCAGAGT ACTTGAAAGA TGAAGAAGCT ACTGCGGAAG
M   .......A.. .......... .......... .......... ..........
    1101                                              1150
N   ATCAACCAAC ACAACCCGAT GTAGCCACAT GCAGGTTTTA CACGCTGGAA
M   ....G..... .......... ........R. .......C.. ....T.....
    1151                                              1200
N   TCCGTCCAGT GGGAGAAAAA TTCCGCTGGA TGGTGGTGGA AGTTCCCCGA
M   .......... .......... .AG....... .......... ..........
    1201                                              1250
N   AGCACTTAAG GACATGGGCC TCTTTGGTCA AAACATGCAT TACCACTACC
M   .......... .......... .......... G.......T. ........T.
    1251                                              1300
N   TCGGTAGAGC AGGCTACACT ATACACGTGC AGTGCAATGC ATCCAAATTC
M   .......... .......... .....T.... .......C.. .........T
    1301                                              1350
N   CACCAAGGCT GTCTACTTGT TGTCTGTGTA CCTGAGGCTG AGATGGGGTG
M   ..T..G.... .......... .......... .....A.... ..........
    1351                                              1400
N   TTCCAAAGTG GACGGTACTG TAAATGAGCA GGAATTGACG GAGGGTGAAA
M   ....C.GAC. ...AAAGAG. .TGC..C.AT .A.CC.C... A.........
    1401                                              1450
N   CGGATATGAA GCTTGAACCC ACCAGAACCA CAGGCGTACG CCGAGTGCAA
M   ...CGCAC.. .T.......A ....A..... ......GC.A .AC.......
    1451                                              1500
N   TCCGCAGTGT ACAACGCGGG TATGGGCGTC GGCGTGGGGA ACCTCACCAT
M   ...AT..... G......... .......A.. .......... ..........
    1501                                              1550
N   CTTCCCTCAC CAGTGGATCA ACCTGCGCAC TAACAACTGT GCTACAATTG
M   ..A....... .......... ..T....... ...T.....C ..........
    1551                                              1600
N   TGATGCCATA CATAAATAGT GTACCCATGG ATAACATGTT TAGGCACTAC
M   .......G.. T......TCA .......... .......... ..........
    1601                                              1650
N   AACTTCACGC TAATGATGAT CCCATTTGCA CCCCTGGATT ACACCAACCA
M   ..T....... .....G.... .......... .......... ...ATGC...
    1651                                              1700
N   AGCATCTACG TACGTACCTA TAACTGTCAC AATAGCACCA ATGTGTGCTG
M   .......GA. .........G .......... ......C... ........A.
    1701                                              1750
N   AATACAATGG TTTGAGGCTC GTTACCTCGC AAGGGTTGCC AGTGATGAAC
M   .......... ...A.....G .C.TA.CA.. .....C.... ....C.A..T
    1751                                              1800
N   ACACCGGGAA GCAATCAGTT CCTGACATCG GATGACTTTC AATCACCTTC
M   .......... .......... TA........ .....T.... ....C.....
    1801                                              1850
N   GGCTATGCCA CAATTTGATG TGACTCCAGA CATGGACATC CCAGGTGAAG
M   .......... .......... .......GC. .......... ..........
```

FIG. 1 Cont'd

```
       1851                                                  1900
N  TGAACAACCT CATGGAGATT GCAGAGGTTG ACTCGGTGGT ACCTGTTAAC
M  ..C....... .......... .....A.... .T........ ..........
       1901                                                  1950
N  AACAATGAGG CCAATCTGAA AAGCATGGAC GCATACCGCA TACCGGTGAA
M  ....C..C.. .........C. .......... .....T.A.. ..GA......
       1951                                                  2000
N  CRCAGGAAAT CAACAAGGTG AAAAGATATT TGGTTTCCAA ATACAACCCG
M  .......... ..C....... .......... C.C......G ..........
       2001                                                  2050
N  GGCTTGATTC AGTGTTAAG AGAACACTGC TAGGTGAGAT GCTCAATTAT
M  ....G..... .......... .......... ........AG. ..........
       2051                                                  2100
N  TACACGCACT GGTCAGGGAG CATTAAGCTA ACATTTATGT TTTGTGGTTC
M  ...G...... .......... .......... .....C.CA. ..........
       2101                                                  2150
N  AGCAATGGCC ACGGGCAAAT TACTCTTAGC ATACTCACCA CCTGGCGCCG
M  .......... ........GC .......... ......C... ..........
       2151                                                  2200
N  ATGTACCGAC TAGCAGAAAG GAGGCAATGC TGGGAACCCA TGTCATCTGG
M  ........G. .......... ....C....A .......... .A........
       2201                                                  2250
N  GACTTTGGGC TGCAATCCAG TTGTGTTCTG TGTGTTCCAT GGATCAGCCA
M  .....A.... .......... ...C.....A ...A...... ........T..
       2251                                                  2300
N  GACACACTAC AGGTTGGTGC AGCAGGATGA GTACACCGGC GCCGGCTATA
M  ......T..T C.CC.A.... .A........ ........A.. .......A..G
       2301                                                  2350
N  TCACCTGCTG GTACCAAACA AGTATAGTGG TTCCACCCGG CACACCCAAA
M  .......... ....T..G... G......... .......... ..........C
       2351                                                  2400
N  AAGTGTGTCA TCCTGTGCTT TGTGTCAGCG TGTAATGATT TCTCCGTGAG
M  ..........G .......... .......... ........C. .........C.
       2401                                                  2450
N  CATGCTGAGT GACACACCAT TCATCGGCCA AACAGCACTG CTGCAGAGCC
M  .......C.. .......... .......... ....A..... ..A..AG.TG
       2451                                                  2500
N  CTGTGGAAGA AGCTGAAGAG AACGCAGTTG CACGTGTGGC TGACACAATT
M  A.AC...C.T G..C.TCA.C ..T.....A. .CA.G..A... ...T......
       2501                                                  2550
N  GCCAGTGGGC CCAGCAACTC CGAGAGCGTT CCTGCACTAA CAGCAGTTGA
M  .......... .......... .ACT...A.. .......... .C........
       2551                                                  2600
N  GACTGGGCAC ACATCACAGG TAGTGCCTAG TGACACAATG CAAACAAGGC
M  .......... .......... ...A...... ...T...... .......C...
       2601                                                  2650
N  ATGTGAAGAA CTACCATTCG AGATCTGAGT CAACAATAGA GAACTTCCTT
M  ....A..... .......... C........A. .......... ..........
       2651                                                  2700
N  AGCAGGTCCG CCTGTGTGTA TATTGAAGAG TACTATACCA ACACTGAAAC
M  ...C....G. ........A.. .......... ....T..... .AGA.C..G.
       2701                                                  2750
N  CAGACAAAAT TTATACATGT TGCCCACTAT AAATACTAGA TGGATGGTGC
M  ...CGCC... AGG....... CATGG..... ....G..... A.........
       2751                                                  2800
N  AATTGAGGAG AAAGTTTGAG ATGTTCACAT ACATGAGGTT TGACATGGAA
M  ........C. ..........A C......... .....C..... ...T......G
       2801                                                  2850
N  ATCACATTTG TTATCACTAG TAGACAACTG CATCGAACTA GCATGCCGCA
M  .......... .......... .......... .C.G.G.... ....CG....
```

FIG. 1 Cont'd

```
     2851                                            2900
N  GGACATGCCG GTACTGACAC ACCAAATCAT GTATGTACCA CCTGGTGGTC
M  A......... CC........ .......... ....A.....C ..........
     2901                                            2950
N  CAGTACCAAA CAGTGTGGAC GATTACGCAT GGCAAACTTC GACTAACCCA
M  .......... ......AC.. ....TT.... .......... ......T....
     2951                                            3000
N  AGTGTCTTTT GGACTGAGGG CAATGCCCCA CCGCGTATGT CCATACCATT
M  ...A...... .......... ........C. .......... ..........
     3001                                            3050
N  CATAAGCATA GGGAATGCAT ACAGCAACTT TTATGATGGG TCCTCGCACT
M  T......... .......... .......... ......C..R .GG.......
     3051                                            3100
N  TCTTACAATA TGGGGTATAT GGCTACAACA CATTAAACAA CATGGGGAAA
M  ...C....A. .........C ........TG .......... ......C...
     3101                                            3150
N  TTATACGTAC GCCATGTGAA CAACCACACA CCATACCAAA TGACCAGTAC
M  .......C.. .......... ...AG..... ..G.....G. ...T......
     3151                                            3200
N  GGTTAGTGTG TACTTTAAAC CCAAACATGT CAGAGCGTGG GTGCCGAGAC
M  .A..C..... .......... ........A. .....T.... .....A....
     3201                                            3250
N  CACCACGTCT GTGCCCCTAC AAAAATGCAT GGAACGTTAA CTTTGAACCA
M  ........T. ..........T .TT..AT.TA .T........ ......C...
     3251                                            3300
N  ACAAACGTAA CTGATTCAAG ATCAAGTATC ACATATATTC CTGAGACGGT
M  ..C...C... .......... ........A. ......G.G. .A...C..TA.
     3301                                            3350
N  CAAACCAGAC CTATCAAAAG CTGGAGCTTT CGGCCACCAG TCCGGTGCTG
M  .CGT..G..A G.CCGT.C.. .....AAA.. .......... ..........
     3351                                            3400
N  TTTATGTGGG TAACTACAGA GTGGTGAATA GGCACCTCGC CACGCACAAC
M  ....C..... ...T...... A.A.....C. .......... ..........
     3401                                            3450
N  GACTGGCAAA ACTGTGTGTG GGAAGACTAC AACAGAGACC TCCTTGTGAG
M  .......... .......... .......... .......... ..........
     3451                                            3500
N  CACCACCACA GCCCATGGGT GTGACACCAT AGCCAGATGC CAGTGCACAA
M  ......T... .......... ......T... .........T .........G
     3501                                            3550
N  CAGGCGTGTA CTTTTGTGCC TCAAGGAACA AACACTACCC AGTCACCTTT
M  .......A.. T......... .......... ....T..... .........C
     3551                                            3600
N  GAGGGGCCAG GCCTGGTGGA AGTTCAGGAG AGTGAGTACT ACCCAAAAAG
M  .......... ..T....... .......... ..C....... ..........
     3601                                            3650
N  ATACCAATCC CATGTGCTTC TAGCTGCAGG ATTTTCTGAA CCAGGCGATT
M  .Y.T..G... ..C....... .......... .......... ..G.......
     3651                                            3700
N  GTGGTGGAAT CCTCAGGTGT GAACATGGTG TCATCGGTAT CGTCACCATG
M  ....C..... ......A... C....C..C. .G........ ..........
     3701                                            3750
N  GGTGGAGAGG GGGTCGTTGG GTTTGCCGAC GTCCGAGACC TACTGTGGTT
M  .......... .......... .......... ...A...... ..........
     3751                                            3800
N  AGAGGATGAT GCCATGGAAC AGGGCGTAAG AGACTATGTT GAACAACTAG
M  .......... .......... .......... .......... ..........
     3801                                            3850
N  GAAATGCTTT TGGCTCAGGT TTCACCAACC AAATTTGTGA ACAAGTCAAC
M  .......... C......... .......T.. .......... ...G......
```

FIG. 1 Cont'd

```
     3851                                                      3900
N    CTCCTCAAAG AGTCACTGGT TGGACAGGAC TCCATTCTGG AGAAATCCCT
M    .......... .....T.... .........T ...T...... .A........
     3901                                                      3950
N    TAAAGCCCTA GTTAAGATTA TCTCAGCACT GGTCATTGTA GTGAGAAATC
M    ...G..T... .......... .......... .....R.... ..........
     3951                                                      4000
N    ACGATGACCT CATCACAGTG ACTGCCACTC TAGCCCTCAT TGGTTGCACC
M    ........T. ...A..G..T ..C....... ....TT.A.. ..........
     4001                                                      4050
N    TCTTCTCCAT GGCGGTGGCT CAAACAGAAA GTGTCACAAT ATTATGGAAT
M    ........G. .......... ...G.....G .......... ..........
     4051                                                      4100
N    ACCCATGGCT GAGCGACAAA ACAATGGCTG GCTCAAGAAG TTCACTGAGA
M    .....G...C .......... .....A.... .......... ...T......
     4101                                                      4150
N    TGACCAATGC CTGCAAGGGC ATGGAGTGGA TAGCCATCAA AATTCAAAAA
M    .......C.. .......... .......... .......A.. .........G
     4151                                                      4200
N    TTTATTGAGT GGCTTAAAGT CAAGAT-CTA CCAGAAGTGT AGGAAAAACA
M    .......... .......... ......T..G ..G......A ..........
     4201                                                      4250
N    TGAGTTCCTC AACAGACTAT AACAACTACC ACTCTTGGAA GAGTCAGATT
M    C......... .....G...A .G...T.... ....C..A..- ...C......
     4251                                                      4300
N    GCCACCATAG AACAAAGTGC ACCATCGCAG AGTGACCAGG AGCAACTGTT
M    ..A....... .G..G..... .......... .....T..A. ........C..
     4301                                                      4350
N    TTCCAATGTC CAGTACTTCG CCCACTATTG CAGAAAGTAT GCGCCACTGT
M    C....C... .......... ....T..... .......... .......T...
     4351                                                      4400
N    ATGCAGCTGA GGCAAAGAGA GTGTTCTCCC TTGAGAAGAA AATGAGCAAT
M    .C..T..C.. A..G...... .......A.. .......... ..........C
     4401                                                      4450
N    TACATACAGT TCAAGTCCAA ATGCCGTATT GAGCCTGTAT GTTTGCTCNT
M    .......... .......... .......... .......... .C..A...C.
     4451                                                      4500
N    ACATGGCAGC CCAGGGGCCG GAAAATCCGT GGCCACCAAC CTGATTGGCA
M    .......... .......... ....G..... .......... T.........
     4501                                                      4550
N    GATCACTCGC TGAAAAACTC AACAGCTCAG TGTACTCCCT ACCACCAGAC
M    ...C...... A......... .......T.. .R........ ..........
     4551                                                      4600
N    CCAGATCACT TGATGGCTA CAAACAGCAA GCGGTCGTGA TCATGGATGA
M    ..C..C.... ....C..... ...G...... .......... ..........
     4601                                                      4650
N    TCTATGCCAA AATCCTGATG GAAAAGATGT GTCATTGTTC TGTCAAATGG
M    CT........ .......... .......... C...C.A..T .....G....
     4651                                                      4700
N    TTTCCAGTGT GGACTTTGTA CCACCGATGG CTGCGCTAGA GGAGAAAGGC
M    ....T..C.. .......... .......... .......... ...A.....A
     4701                                                      4750
N    ATTCTGTTCA CCTCCCCGTT TGTCCTGGCA TCAACCAATG CTGGGTCCAT
M    ..C..A..T. .......... C..GT..... .........C. ..........
     4751                                                      4800
N    CAATGCACCA ACTGTGTCAG ACAGCAGAGC CCTCGCTAGG AGATTCCACT
M    .........C .......T.. .......... G......... ..........
     4801                                                      4850
N    TTGACATGAA CATTGAAGTC ATTCCATGT ACAGTCAAAA TGGCAAGATC
M    .......... .......... .....T.... .......... C.........
```

FIG. 1 Cont'd

```
     4851                                                     4900
N    AACATGCCCA TGTCAGTTAA GACGTGTGAT GAAGAGTGTT GTCCAGTCAA
M    .......... .......... A..A...... .......... .......T...
     4901                                                     4950
N    CTTCAAGAGG TGCTGCCCGC TGGTGTGTGG AAAGGCCATG CAGTTCATTG
M    ......A... ..........T .......... .......Y... ..A.......
     4951                                                     5000
N    ACAGAAGAAC TCAAGTTAGA TACTCGCTGG ACATGCTAGT TACTGAGATG
M    .T..G..... .......... ..T....... .......... ......A...
     5001                                                     5050
N    TTTAGGGAGT ACAACCACAG ACACAGTGTG GGAGCCACCC TTGAGGCTCT
M    .......... .T......T.. .......... .........T. .....A....
     5051                                                     5100
N    GTTCCAAGGG CCACCAGTCT ACAGAGAGAT CAAAATTAGT GTCGCACCAG
M    .......... .......... .......... .......C..C .....C....
     5101                                                     5150
N    AGACACCACC ACCACCAGCT ATTGCTGACT TACTGAAATC AGTGGACAGT
M    .......C.. .......... .......T.. .......... ..........
     5151                                                     5200
N    GAAGCTGTGA GAGAGTACTG CAAAGAAAAG GGATGGCTTG TGCCAGAGAT
M    .......... .G..A..... ...G..G.GA ..G....... ..........
     5201                                                     5250
N    CAACTCCACC CTACAAATTG AGAAGCATGT GAGCCGGGCA TTCATCTGTC
M    ...T..T... .........A. .......... ...TA.A... .....A...T
     5251                                                     5300
N    TGCAAGCACT AACCACGTTT GTTTCAGTTG CTGGAATAAT ATACATTATT
M    .A.....C... .......... .......... ....T..... ..........
     5301                                                     5350
N    TACAAGCTAT TTGCAGGTTT CCAAGGCGCA TACACAGGGA TGCCCAACCA
M    .....AT... .......... .........C .......... ..........
     5351                                                     5400
N    GAAACCCAAG GTGCCCACCC TGAGACAAGC CAAAGTGCAA GGCCCAGCGT
M    ......T... .......... ......G... ......A..G ..........
     5401                                                     5450
N    TTGAGTTTGC TGTGGCGATG ATGAAGAGGA ACTCCAGTAC AGTGAAAACC
M    .......C.. .......... .....A.... ..G....... ...A......
     5451                                                     5500
N    GAGTACGGTG AGTTCACCAT GCTTGGCATT TATGACAGGT GGGCGGTGTT
M    .......... .A........ .......... ..C....A... ..........
     5501                                                     5550
N    ACCACGCCAC GCCAAACCTG GCCCAACCAT CTTGATGAAT GACCAGGAAG
M    ...G...... .....G.... ....C..... .......... ..T.......
     5551                                                     5600
N    TCGGCGTGTT GGATGCCAAG GAACTAGTGG ATAAGGATGG GACAAACCTA
M    .......... .......... ......T.. .....A..... .......T...
     5601                                                     5650
N    GAACTGACAC TCCTGAAGCT CAACAGTAAT GAGAAGTTCA GAGACATCAG
M    ...T....T. .......... ....C....C ..A....... ....T...T..
     5651                                                     5700
N    AGGGTTCCTA GCCAAAGAAG AGGTTGAGGT GAATGAAGCT GTCCTAGCAA
M    G.....T... ..A.G..... .......A.. .......... ..........
     5701                                                     5750
N    TAAACACAAG CAAGTTCCCC AACATGTACA TACCAGTGGG CCAGGTGACT
M    .....T..... ...A.....T .......... .......... ..........
     5751                                                     5800
N    GACTACGGGT TCCTGAACCT GGGTGGGACG CCCACTAAGA GAATGCTCAT
M    .......... .T........ ...A.....T .....G.... ..........
     5801                                                     5850
N    GTACAACTTC CCCACTAGAG CAGGTCAGTG TGGTGGTGTC CTCATGTCCA
M    ...T...... ..A....... .......... ...A...... ........A.
```

FIG. 1 Cont'd

```
       5851                                                      5900
N  CTGGGAAAGT CCTGGGGATA CATGTTGGTG GGAATGGTCA TCAAGGGTTC
M  .A........ ......A... .....A..A. ........A. ..........
       5901                                                      5950
N  TCAGCAGCAC TCCTCAAGCA CTACTTCAAC GATGAACAAG GTGAAATAGA
M  ......G... ......G... .......... ..G..G..G. ..........
       5951                                                      6000
N  GTTCATTGAG AGCTCAAAGG ACGCGGGGTT CCCTATCATC AACACACCCA
M  A......... .......... ........A. .....G.G.. .....T....
       6001                                                      6050
N  GCAAGACCAA ACTGGAACCA AGTGTCTTCC ACCAG-TGTT TGAAGGCAAC
M  .T.....A.. .T........ .....G..T. ......G... C..G......
       6051                                                      6100
N  AAAGAACCCA GCAGTCCTCA GAAATGGTGA TCCACGACTC AAAGCCAACT
M  ..G.....-. ..G.....T. .......G.. C......... ..........
       6101                                                      6150
N  TTGAGGAGGC CATCTTCTCC AAATACATTG GCAATGTCAA CACGCATGTG
M  .C.....A.. A......... ..G....... .......... .........A
       6151                                                      6200
N  GATGAGTACA TGTTGGAAGC TGTGGACCAT TATGCAGGAC AACTGGCTAC
M  .......... .......G.. .......... .......... ....A.....
       6201                                                      6250
N  TCTGGACATC AGCACGGAAC CAATGAAGCT GGAGGATGCC GTGTATGGTA
M  .......... ..T.....G. .C........ A.....C... ..........
       6251                                                      6300
N  CAGAGGGGCT GGAAGCACTA GACCTAACAA CCAGTGCAGG CTACCCTTAT
M  .......... .......... ........C. .......... .........C
       6301                                                      6350
N  GTTGCCCTGG GCATCAAGAA GAGAGACATC CTATCTAAGA AGACCAGGGA
M  ..G....... .......... A.....T..T .......... ....T.AA..
       6351                                                      6400
N  CCTCACTAAG TTGAAAGAAT GCATGGACAA GTATGGCCTA AACCTGCCAA
M  .......... .....G.... .......... A......... ..TT......
       6401                                                      6450
N  TGGTAACCTA TGTGAAAGAT GAGCTCAGAT CTGCAGAGAA GGTGGCCAAA
M  .......... C..C...... ...T.G.... ....T..... .........G
       6451                                                      6500
N  GGAAAATCCA GGCTTATTGA AGCTTCCAGT TTGAATGACT CAGTGGCAAT
M  .......... .......... G.....T... C.C....... ....A.....
       6501                                                      6550
N  GAGACAGACA TTTGGAAACC TGTACAAAAC CTTCCACCTC AACCCAGGCA
M  ...G..A... ........TT .A..T..G.. ...T...... .....G....
       6551                                                      6600
N  TTGTGACGGG CAGTGCAGTT GGGTGTGACC CAGATCTGTT TTGGAGCAAG
M  .C..T..... ......T... .........T. .....G.... ..........
       6601                                                      6650
N  ATACCAGTCA TGTTGGATGG ACATCTCATA GCTTTTGATT ACTCAGGCTA
M  ..C..T..T. ..C.T..... .......... ........C. .T........
       6651                                                      6700
N  TGATGCTAGC CTCAGCCCAG TGTGGTTTGC ATGTCTGAAA CTGCTCCTAG
M  ...C...... .......... .......... ....T..... ..T.......
       6701                                                      6750
N  AGAAGCTTGG GTACACACAC AAGGAAACAA ACTACATAGA TTACCTCTGC
M  ....A..A.. ...T....A. .......... .......... .........T
       6751                                                      6800
N  AACTCCCACC ACCTGTACAG AGACAAACAC TACTTTGTGC GAGGTGGTAT
M  ..T....T.. .......T.. ......G... ........AA ....C.....
       6801                                                      6850
N  GCCATCAGGG TGTTCTGGCA CCAGCATCTT TAACTCAATG ATTAACAACA
M  .......... .....A.... .......A.. ...T..C... ..........
```

FIG. 1 Cont'd

```
      6851                                            6900
N   TCATAATCAG GACACTCATG CTGAAAGTGT ACAAGGGCAT TGACTTGGAC
M   .......... ...T...... .....G..T. .T..A..... ...T......
      6901                                            6950
N   CAATTCAGGA TTATTGCCTA TGGTGATGAT GTGATTGCTT CCTACCCGTG
M   .........A. .G........ ...G...... .......... ....T.....
      6951                                            7000
N   GCCCATTGAT GCTTCCCTGC TAGCTGAAGC AGGAAAAGAT TATGGTTTGA
M   ...T..C... .....G...T .......... .......... .........A.
      7001                                            7050
N   TCATGACACC AGCAGATAAA GGAGAGTGCT TCAATGAAGT CAACTGGACG
M   .......C.. ......C... ..C....... ....C..G.. A.C.......
      7051                                            7100
N   AATGTCACCT TCCTGAAAAG GTACTTTAGA GCAGATGAGC AATACCCATT
M   .....G.... .T........ .........G .......... ..........
      7101                                            7150
N   CCTGGTCCAC CCTGTTATGC CCATGAAAGA CATCCATGAA TCTATTAGAT
M   T........T .......... .A......G.. .........G ........G.
      7151                                            7200
N   GGACCAAAGA TCCAAAGAAC ACCCAAGATC ATGTGCGCTC GCTGTGCCTA
M   .......... ...C...... ..A..G.... .......... ..........
      7201                                            7250
N   TTGGCTTGGC ACAATGGGGA GCACGAATAT GAGGAGTTCA TTCGCAAAAT
M   .......... ....C..... ...A...... .........T. ........G..
      7251                                            7300
N   CAGAAAGCGT GCCAGTTGGA CGCTGTTTGA CCCTACCTGC GTTTTCAACC
M   .....-.... ...C.....G .....C.... .......C.. T.........A
      7301                                            7350
N   CTGCGCAGGA AGTGGTTGGA CTCCTTTTAA AATAA-AGCA CAATTTAGTA
M   .......... .....C..... .......... ...T.G.... T....-....
      7351                                            7400
N   AATTTGAATT GGCTTAACCC TACCGCACTA ACCGAACTAG ATAACGGTGC
M   ...CAT.... .......... .......TG. .........T. ....AA....
      7401                                    7437
N   GGTAGGGGTA AATTCTCCGC ATTCGGTGCG GTCGAGG
M   .......... .......... .......... .-------

Sequence identity: 90.3%
```

FIG. 2

Comparison of amino acid sequences of the unmodified (native) virus and modified virus

N: Unmodified (native) virus
M: Modified virus

```
      1                                                        50
N   MGAQVSTQKT GAHETXLSAN GSSIIHYTNI NYYKDAASNS ANRQDFTQDP
M   .......... .......... .H........ .......... ..........
     51                                                       100
N   GKFTEPVKDI MIKSMPALNS PTVEECGYSD RVRSITLGNS TITTQESANV
M   .......... .......... .SA....... ....L..... ..........
    101                                                       150
N   VVGYGGWPEY LKDEEATAED QPTQPDVATC RFYTLESVQW EKNSAGWWWK
M   .....R.... .......... .......... .......... ..........
    151                                                       200
N   FPEALKDMGL FGQNMHYHYL GRAGYTIHVQ CNASKFHQGC LLVVCVPEAE
M   .......... .....L.... .......... .......... ..........
    201                                                       250
N   MGCSKVDGTV NEQELTEGET DMKLEPTRTT GVRRVQSAVY NAGMGVGVGN
M   ....QT.KE. AAMN..K... AH.F...K.. .GHT...I.C .....I....
    251                                                       300
N   LTIFPHQWIN LRTNNCATIV MFYINSVPMD NMFRHYNFTL MMIPFAPLDY
M   ...Y...... .......... .......... .......... .V........
    301                                                       350
N   TNQASTYVPT TVTIAPMCAE YNGLRLVTSQ GLPVMNTPGS NQFLTSDDFQ
M   NA...E...V .......... ......AYQ. ....L..... ...M......
    351                                                       400
N   SPSAMPQFDV TPDMDIPGEV NNLMEIAEVD SVVPVNNNEA NLKSMDAYRI
M   .......... ..H....... H......... .......TA. ..Q.....H.
    401                                                       450
N   PVNXGNQQGE KIFGFQIQFG LDSVFKRTLL GEMLNYYTHW SGSIKLTFMF
M   E....H.... ...A...... .......... ..V....A.. ........T.
    451                                                       500
N   CGSAMATGKL LLAYSPPGAD VPTSRKEAML GTHVIWDFGL QSSCVLCVPW
M   .......... .......... ..A...Q..M ....I...L. ........I..
    501                                                       550
N   ISQTHYPLVQ QDEYTGAGYI TCWYQTSIVV PPGTPKKCVI LCFVSACNDF
M   .......... .....S..NV ......G... .....N...V ..........
    551                                                       600
N   SVSMLSDTPF IGQTALLQSP VEEAEENAVA RVADTIASGP SNSESVPALT
M   ..R..R.... ....T...GD TDV.VN.... .......... ...T.I....
    601                                                       650
N   AVETGHTSQV VPSDTMQTRH VKNYHSRSES TIENFLSPSA CVYIEEYYTN
M   .......... E......... .......... .......... ......FTK.
    651                                                       700
N   TETRQNLYML PTINTRWMVQ LRRKFEMFTY MRFDMEITFV ITSRQLHRTS
M   DQDSA.R..S W...ARR... ......L... .......... ......PG..
    701                                                       750
N   MPQDMPVLTH QIMYVPPGGP VPNSVDDYAW QTSTNPSVFW TEGNAPPRMS
M   TA....P... ....I..... .....T.F.. ........I.. ..........
    751                                                       800
N   IFFISIGNAY SNFYDGSSHF LQYGVYGYNT LNNMGKLYVR HVNNHTPYQM
M   .......... ......W... S.N......A .........A. ...KD.....
    801                                                       850
N   TSTVSVYFKP KHVRAWVPRP PRLCPYKNAW NVNFEPTNVT DSRSSITYIP
M   S..IR..... ..I.V..... ......IKSS ....D...L. ........V.
```

```
          851                                                    900
    N  ETVKPDLSKA GAFGHQSGAV YVGNYRVVNR HLATHNDWQN CVWEDYNRDL
    M  D.IR.EVRT. .K........ ......I... .......... ..........
          901                                                    950
    N  LVSTTTAHGC DTIAPCQCTT GVYFCASRNK HYPVTFEGPG LVEVQESEYY
    M  .......... ........A. .......... .......... ..........
          951                                                   1000
    N  PKRYQSHVLL AAGFSEPGDC GGILRCEHGV IGIVTMGGEG VVGFADVRDL
    M  ...X...... .......... ......Q... .......... ..........
         1001                                                   1050
    N  LWLEDDAMEQ GVRDYVEQLG NAFGSGFTNQ ICEQVNLLKE SLVGQDSILE
    M  .......... .......... .......... .......... ..........
         1051                                                   1100
    N  KSLKALVKII SALVIVVRNH DDLITVTATL ALIGCTSSPW RWLKQKVSQY
    M  .......... ....X..... .......... .......... ..........
         1101                                                   1150
    N  YGIPMAERQN NGWLKKFTEM TNACKGMEWI AIKIQKFIEW LKVKIYQKCR
    M  ....R..... .S........ .......... .......... .....LPEVK
         1151                                                   1200
    N  KNMSSSTDYN NYHSWKSQIA TIEQSAPSQS DQEQLFSNVQ YFAHYCRKYA
    M  EKHEFLNRLK QLPLLE.... .......... .......... ..........
         1201                                                   1250
    N  PLYAAEAKRV FSLEKKMSNY IQFKSKCRIE PVCLLKHGSP GAGKSVATNL
    M  .......... .......... .......... ......L... ..........
         1251                                                   1300
    N  IGRSLAEKLN SSVYSLPPDP DHFDGYKQQA VVIMDDLCQN PDGKDVSLFC
    M  .......... .......... .......... .......... ..........
         1301                                                   1350
    N  QMVSSVDFVP PMAALEEKGI LFTSPFVLAS TNAGSINAPT VSDSRALARR
    M  .......... .......... .......... .......... ..........
         1351                                                   1400
    N  FHFDMNIEVI SMYSQNGKIN MPMSVKTCDE ECCPVNFKRC CPLVCGKAMQ
    M  .......... .......... .......... .......... ..........
         1401                                                   1450
    N  FIDRRTQVRY SLDMLVTEMF REYNHRHSVG ATLEALFQGP PVYREIKISV
    M  .......... .......... .......... .......... ..........
         1451                                                   1500
    N  APETPPPPAI ADLLKSVDSE AVREYCKEKG WLVPEINSTL QIEKHVSRAF
    M  .......... .......... ......R... .......... ..........
         1501                                                   1550
    N  ICLQALTTFV SVAGIYIIY KLFAGFQGAY TGMPNQKPKV PTLRQAKVQG
    M  .......... .......... .......... .......... ..........
         1551                                                   1600
    N  PAFEFAVAMM KRNSSTVKTE YGEFTMLGIY DRWAVLPRHA KPGPTILMND
    M  .......... ...A...... .......... .K........ ..........
         1601                                                   1650
    N  QEVGVLDAKE LVDKDGTNLE LTLLKLNSNE KFRDIRGFLA KEEVEVNEAV
    M  .......... .......... ......R.. .......... R.........
         1651                                                   1700
    N  LAINTSKFPN MYIPVGQVTD YGFLNLGGTP TKRMLMYNFP TRAGQCGGVL
    M  .......... .......... .......... .......... ..........
         1701                                                   1750
    N  MSTGKVLGIH VGGNGHQGFS AALLKHYFND EQGEIEFIES SKDAGFPIIN
    M  .......... ....R....E .......... .......... .......V..
         1751                                                   1800
    N  TPSETKLEPS VFHQCLKATK NPAVLRNGDP RLKANFEEAI FSKYIGNVNT
    M  .......... .....VFEGN. E......... .......... ..........
         1801                                                   1850
    N  HVDEYMLEAV DHYAGQLATL DISTEPMKLE DAVYGTEGLE ALDLTTSAGY
    M  .......... .......... .......... .......... ..........
```

FIG. 2 Cont'd

```
      1851                                                    1900
N   PYVALGIKKR DILSKKTRDL TKLKECMDKY GLNLPMVTYV KDELRSAEKV
M   .......... .......K.. .......... .......... ..........
      1901                                                    1950
N   AKGKSRLIEA SSLNDSVAMR QTFGNLYKTF HLNPGIVTGS AVGCDPDLFW
M   .......... .......... .......... .......... .......V..
      1951                                                    2000
N   SKIPVMLDGH LIAFDYSGYD ASLSPVWFAC LKLLLEKLGY THKETNYIDY
M   .......... .......... .......... .......... .N........
      2001                                                    2050
N   LCNSHHLYRD KHYFVRGGMP SGCSGTSIFN SMINNIIIRT LMLKVYKGID
M   .......... .......... .......... .......... ..........
      2051                                                    2100
N   LDQFRIIAYG DDVIASYPWP IDASLLAEAG KDYGLIMTPA DKGECFNEVN
M   .....M.... .......... .......... .......... .........T
      2101                                                    2150
N   WTNVTFLKRY FRADEQYPFL VHPVMPMKDI HESIPWTKDP KNTQDSVRSL
M   .......... .......... .......... .......... ..........
      2151                              2196
N   CLLAWHNGEH EYEEFIRKIR KRASWTLFDP TCVFNPAQEV VGLLLK
M   .........Q .......... SVPVGRCLTL PAFSTLRRKW LDSF--

Sequence identity: 91%
```

FIG. 2 Cont'd

GENETICALLY STABLE ONCOLYTIC RNA VIRUS, METHOD OF MANUFACTURING AND USE THEREOF

TECHNICAL FIELD

The invention relates to development of a novel biotechnologically produced anti-cancer preparation, namely to a genetically stable oncolytic RNA virus, a method for manufacturing the oncolytic virus, and use thereof.

BACKGROUND ART

The ability of viruses to kill cancer cells is known for more than a century [Kelly, E.; Russell, S. J. History of oncolytic viruses: genesis to genetic engineering. Mol. Ther. 2007, 15, pp. 651-659] and there were numerous promising successes in experimental cancer therapy with various viruses, nevertheless their use in clinical practice is hampered by the difficulty to foresee the interaction between the tumour and its host, as well as the virus and response of human immune system to viral antibodies.

Although the clinical investigations regarding the use of viruses in cancer therapy commenced more than 50 years ago, at present only two viruses are approved for clinical use in cancer therapy. They are adenovirus with deleted E1B 55K gene (Garber, K. China approves world's first oncolytic virus therapy for cancer treatment. J. Natl. Cancer Inst. 2006, 98, pp. 298-300) and unmodified passivized Picornaviridae Enterovirus of Echo type (Eurasian patent 007839; European patent application 03733607), acting as antitumour immunostimulant.

Therefore, the development of novel efficient oncolytic viruses is still a topical problem (Han Hsi Wong, Nicholas R. Lemoine, Yaohe Wang, Viruses 2010, 2, pp. 78-106).

In order to increase the potential of virus so selectively infect cancer cells and heighten the oncolytic activity, a number of modified viruses have been disclosed. They are characterised by deletion of specific genes, thus preventing their propagation in normal cells, or integration of additional genes for improving the oncolytic properties.

However, the limited knowledge concerning the genetical modifications that provide for selectivity and efficiency against the tumour cells, results in modified viruses with lower cytolytic activity, compared to origin, or higher anti-virus response of human immune system (S. Meerani, Yang Yao, Oncolytic viruses in cancer therapy. European Journal of Scientific Research, vol. 40 no. 1 (2010), pp. 156-171; Han Hsi Wong, Nicholas R. Lemoine, Yaohe Wang, Viruses 2010, 2, 78-106).

Although viruses are well-established tools for conveying vectors into cell, their use is limited by the high immunogenicity of viruses (Peng, Z. Current status of gendicine in China: recombinant human Ad-p53 agent for treatment of cancers. Hum. Gene. Ther. 2005, 16, 1016-1027).

One of the most serious adverse properties of non-modified ECHO type viruses, including ECHO 7, is their ability to cause infections that may have a fatal result (Wreghitt T. G., Gandy G. M., King A., Sutehall G., Fatal neonatal ECHO 7 virus infection, The Lancet, vol. 324, p. 465, 1984). These viruses are known to be responsible for hand, foot and mouth disease in Malaysia (http://www.vadscornercom/ecovirus7.html), for myocarditis in leukemic child (Midula M., Marzetti G., Borra G., Sabatino G., Myocarditis associated with ECHO 7 type infection in leukemic child, Acta Paediatrica Volume 65, Issue 4, pp. 649-651, July 1976), aseptic meningitis, paralytic disease and fever (http://virology-online.com/viruses/Enteroviruses6.htm). Therefore pathogenicity is one of the major limitations that must be overcome in using ECHO 7 type viruses in treating cancer patients.

DISCLOSURE OF THE INVENTION

Technical Problem

Therefore, the problem to solve was the development a highly efficient, selective oncolytic virus without pathogenicity in normal cells and low immunological response, and possessing high genetic stability. It is well known and recognised that RNA viruses mutate very easily upon passage in cell cultures, which can change the phenotype, leading to increased pathogenicity. Thus, for preparation of oncolytic virus-based medicine by using a wild non-pathogenic ECHO 7 virus strain as the starting material, it is of extreme importance to find a procedure which would allow to generate an oncolytic modification of this virus that would retain non-pathogenic character of the original virus and be genetically stable.

Solution to the Problem

This problem was surprisingly solved by a targeted modification of a single-strand RNA virus by developing a method that utilized the high mutation potential of single strand RNA virus in combination with a specifically targeted selection of mutants, providing for fast separation from the pool of mutant species with high and selective oncolytic activity. Many cancer cells are resistant to the virus (the virus can not enter the cell and survive there). By careful selection of cell lines where the virus is modified and by proper pre-treatment of the cancer cells it is possible to create a genetically stable and non-pathogenic virus for cancer treatment. The virus provided by the invention is in fact the first disclosure of a genetically stable oncolytic virus, based on ECHO-7 type virus, said genetically stable virus bring usable for long term manufacturing (a multiple reproduction) as medicine.

SHORT DESCRIPTION OF THE INVENTION

We have developed a method for modifying the native ECHO 7 virus, identified by genome sequence SeqNo2, the method comprising initially conducting the virus adaptation in cancer cells, attenuated by an anti-cancer agent such as dacarbazine, passaging the modified virus in human embryonal fibroblast culture, propagation in human melanoma cells and passaging in human embryonal fibroblast culture, optionally treated by ribavirin, isolation of the virus and purification of the virus. The virus can be isolated and purified by known methods. The use of anticancer agent such as dacarbazine in subtoxic concentrations for modification of cancer cells and using these treated cancer cells as host cells for virus replication has led to creation of mutant virus with stable genome applicable as highly effective medicine for treatment of cancer.

More than one type of cell lines can be used during conducting the virus adaptation.

BRIEF DESCRIPTION OF THE FIGURES

FIG. 1 is a comparison of genomes of the modified virus (Seq ID No 1) and unmodified (native) virus (Seq ID No 2), and FIG. 2 is a comparison of amino acid sequences of the modified virus (Seq ID No 4) and unmodified (native) virus (Seq ID No 5).

SEQUENCE LISTING FREE TEXT

Seq ID No 1: Modified virus;
Seq ID No 2: Unmodified (native) virus;
Seq ID No 3: Modified virus after propagation for 12 months;
Seq ID No 4: Amino acid sequence of the modified virus;
Seq ID No 5: Amino acid sequence of the unmodified virus;
Seq ID No 6: Primer Eo7-1F; Seq ID No 7: Primer Eo7-1R;
Seq ID No 8: Primer Eo7-2F; Seq ID No 9: Primer Eo7-2R;
Seq ID No 10: Primer Eo7-3F; Seq ID No 11: Primer Eo7-3R;
Seq ID No 12: Primer Eo7-4F; Seq ID No 13: Primer Eo7-4R;
Seq ID No 14: Primer Eo7-5F; Seq ID No 15: Primer Eo7-5R;
Seq ID No 16: Primer Eo7-6F; Seq ID No 17: Primer Eo7-6R;
Seq ID No 18: Primer Eo7-7F; Seq ID No 19: Primer Eo7-7R;
Seq ID No 20: Primer Eo7-8F; Seq ID No 21: Primer Eo7-8R;
Seq ID No 22: Primer Eo7-9F; Seq ID No 23: Primer Eo7-10F;
Seq ID No 24: Primer Eo7-9R; Seq ID No 25: Primer Eo7-11F;
Seq ID No 26: Primer Eo7-11R; Seq ID No 27: Primer Eo7-12F;
Seq ID No 28: Primer Eo7-12R; Seq ID No 29: Primer Eo7-13F;
Seq ID No 30: Primer Eo7-13R; Seq ID No 31: Primer Eo7-14F;
Seq ID No 32: Primer Eo7-14R; Seq ID No 33: Primer Eo7-15F;
Seq ID No 34: Primer Eo7-15R; Seq ID No 35: Primer Eo7-16F;
Seq ID No 36: Primer Eo7-17F; Seq ID No 37: Primer Eo7-16R;
Seq ID No 38: Primer Eo7-18F; Seq ID No 39: Primer Eo7-18R;
Seq ID No 40: Primer Eo7-19F; Seq ID No 41: Primer Eo7-19R;
Seq ID No 42: Primer Eo7-20F; Seq ID No 43: Primer Eo7-20R;
Seq ID No 44: Primer Eo7-21F; Seq ID No 45: Primer Eo7-21R;
Seq ID No 46: Primer Eo7-22F; Seq ID No 47: Primer Eo7-22R;
Seq ID No 48: Primer Eo7-23F; Seq ID No 49: Primer Eo7-23R;
Seq ID No 50: Primer Eo7-24F; Seq ID No 51: Primer Eo7-24R;
Seq ID No 52: Primer Eo7-25F; Seq ID No 53: Primer Eo7-25R;
Seq ID No 54: Primer Eo7-26F; Seq ID No 55: Primer Eo7-26R.

DETAILED DESCRIPTION OF THE INVENTION

We have unexpectedly discovered the suitability for this purpose of a known Echo 7 type Picornaviridae enterovirus, isolated from a human intestine. The original nucleotide sequence, determined by a standard method, was found to be rather similar to that of Wallace type Picornaviridae Enterovirus.

Checking the oncolytic activity of isolated native enteroviruses in tissue of angiosarcoma demonstrated that neither individual viruses nor their combinations in a dose $3\times10^5$ $TCID_{50}/0.03$ ml possessed substantial oncolytic activity with exception of ECHO 7 type that showed more promising activity (Table 1).

TABLE 1

Influence of viruses on angiosarcoma tissue culture

| Virus | Number of animals | Number of regressed tumours on Day 4 after infecting | Isolated (surviving) virus | Viral titer on Day 4, $TCD_{50}$/0.1 ml |
|---|---|---|---|---|
| ECHO 4 | 6 | 0 | ECHO 4 | $10^6$-$10^7$ |
| ECHO 7 | 6 | 0 | ECHO 7 | $10^5$-$10^6$ |
| Coxsackie B-5 | 6 | 0 | Coxsackie B-5 | $10^7$-$10^8$ |
| ECHO 4 + ECHO 7 | 6 | 2 | ECHO 7 | $10^9$ |
| ECHO 4 + Coxsackie B-5 | 6 | 1 | ECHO 4, Coxsackie B-5 | $10^3$ } $10^8$ |
| ECHO 7 + Coxsackie B-5 | 6 | 0 | ECHO 7 | $10^4$ } $10^8$ |
| Control | 6 | 0 | | $10^8$ |

The instability of the genome of the RNA single strand viruses is a well-known fact; therefore, such viruses usually are not selected for constructing oncolytic viral agents.

The modification of the isolated native virus was realised in several consecutive steps.

The first step takes advantage of the high mutation potential of RNA viruses (on average one mutation on each replication) to develop a cytopathic mutant by replicating the virus in trypsinized monolayer of human embryonic fibroblast culture in presence of calf serum.

Cells were incubated for 10 days, carrying out the passage each time when the cells in culture had degenerated for 50%.

Testing the selected virus in RD cell culture a pronounced cytopathic effect was observed already in 24 hours after infection. The titer of the developed virus, determined by last dilution method was $TCID_{50}=1\times10^{-8}$.

This strain was propagated, isolated and stored at −70° C. for further use in producing selective and genetically stable oncolytic strain.

The virus so obtained was modified, using specially developed method comprising three steps.

1st Modification Step in a First Tumour Cell Line

In the first modification step, the virus was propagated in tumour cell lines attenuated by anticancer agent. Human breast adenocarcinoma cell line (MCF-7) was used in this step.

A monolayer of these cells was treated with dacarbazine DTIC in sub toxic dose (20 μM). After treating with dacarbazine, the cells were transferred to fresh culture medium and contacted with the virus, and the propagation continued without adding serum. After 24 hours from contacting with the virus, the cells were removed and the virus was isolated from the media.

The virus was repeatedly propagated (passaged) in human embryonic fibroblast cell culture and again used for infecting the MCF-7 cell line. This procedure was repeated 10 times. Thus, this modification step comprises alternately propagating the virus in human breast adenocarcinoma cells and human embryonic fibroblast cells.

2nd Modification Step in a Second Tumour Cell Line

In the next modification step, the virus as described above, was contacted with gastric adenocarcinoma cell culture. A monolayer of these cells was treated with dacarbazine DTIC in sub toxic dose (20 µM).

The monolayer of these cells was infected by the virus, which was isolated after the modification in the first step, and the propagation continued in a culture medium without serum.

After 24 hours from contacting with the virus, the cells were removed and virus isolated from the media. The virus was repeatedly propagated (passaged) in human embryonic fibroblast cell culture, and thereafter again used for infecting the gastric adenocarcinoma cell line. This procedure was repeated 10 times. Thus, this second modification step comprises alternately propagating the virus in gastric adenocarcinoma cells and in human embryonic fibroblast cells.

In the first modification step and in the second modification step, the propagation procedure was always finished by propagating the virus last in the human embryonic fibroblast culture.

3rd Modification Step in Human Melanoma Cells

The virus produced in the second step was used for infecting human tumours, obtained in surgery.

Melanoma cancer tissues were obtained in surgery from 23 patients previously treated by chemotherapy.

Tissues were infected by the modified virus and incubated at 37° C. in the absence of carbon dioxide. Before being used for infecting a new tissue material (fresh melanoma tissue from another patient), the modified virus was repeatedly propagated in human embryonic fibroblast culture to titer 7 lg $TCID_{50}$/1 ml.

The modified virus was propagated in human embryonic fibroblast cell culture that was treated by 5 mM ribavirin 7 hours before infection and cultivated for 24 hours. The virus was isolated from the culture, and the procedure of propagating the virus in the fibroblast culture was repeated 10 times.

Finally, the virus was isolated, purified and propagated in human embryonic fibroblast culture without addition of ribavirin.

The propagated virus was used for sequence determination. The genome of the modified virus differs from that of frozen unmodified native virus (Echo 7 type Wallace strain from NCBI database) for about 10%, the coat part for about 12%.

The virus modified by the described method was found to be surprisingly stable. Its genome changed for only 0.7% after continuous passaging for 12 months (propagation for 12 months in human embryonal lung culture MRC 5). Especially important is the fact that the modified virus (further on MV) is characterised by exceptionally high cytopathic effect on malignant cells and low cytotoxicity on normal cell lines as well as no toxicity in vivo in mice.

In experiments with cell lines MV was found to be cytotoxic for melanoma cell lines FM9, FM55, FM94 and SK-Me126, gastric carcinoma cells, human oral squamous cell carcinoma SCC25 cells, human epithelial cell line derived from a lung carcinoma (A549), acute monocyte leukemia THP-1 cells, rabdomyosarcoma RD cells, human pancreatic adenocarcinoma HPAF-II cells, human breast adenocarcinoma cells (MCF-7) as well as on primary cell cultures of gastric adenocarcinoma GC1 and thyroid cancer line HA007. In animal experiments, MV caused regression of murine sarcoma M-1, mice fibrosarcoma MX-17 as well as transplantable tumours—Moloney sarcoma (SM) and KRS-321 sarcoma.

In a clinical pilot study, a group of 46 melanoma stage I patients no progress of melanoma was observed for 50 months in 43 patients, treated with MV. In the control group, melanoma progressed for 10 of 31 patients undergoing standard therapy.

In a 50 months study of 44 stage II melanoma patients the progress of melanoma was stopped in 38 patients, compared to control group of 36 patients undergoing standard therapy, where melanoma did not progress in 15 patients, but did progress in 21 patient. No serious adverse effects were observed for patients treated with MV.

INDUSTRIAL APPLICABILITY

We have developed a novel virus strain (MV) with original genome sequence, stable against genetic drift, possessing cytopathic activity against various types of tumours, characterized by low incidence of adverse effects and low toxicity that can be used with advantage in cancer virotherapy. Thus, we have unexpectedly solved the main obstacle in wider use of RNA viruses in medicine—obtained genetically stable strain that can be used in standardized continuous manufacturing of oncolytic viral preparation. The viral preparation can be used in anticancer therapy against a variety of tumour cells.

EXAMPLES

The present invention is described in Examples in more detail. However, the invention is not construed as being limited to the examples.

Virus

The virus modified according to the invention is ECHO-7 virus (Picornaviridae family, Enterovirus genus, ECHO (Enteric Cytopathic Human Orphan) type 7, group IV, positive-sense single stranded RNA virus). The native virus can be identified by genome sequence Seq Id No 2.

Example 1

The Isolation and Characterization of the Original Virus Strain

A known method for isolation (A. C. Rentz, J. E. Libbey, R. S. Fujinami, F. G. Whitby, and C. L. Byington. Investigation of Treatment Failure in Neonatal Echovirus 7 Infection. The Pediatric Infectious Disease Journal, Volume 25, Number 3, March 2006, 259) and propagation in BS—C-1 cell line (CCL 26; ATCC) was used (Libbey J E, McCright I J, Tsunoda I, et al. Peripheral nerve protein, PO, as a potential receptor for Theiler's murine encephalomyelitis virus. J Neurovirol. 2001; 7:97-104. Pevear D C, Tull T M, Seipel M E, et al. Activity of pleconaril against enteroviruses. Antimicrob Agents Chemother. 1999; 43:2109-2115). Virus propagation and determination of titer was conducted in concordance with the published method (Zurbriggen A, Fujinami R S. A neutralization-resistant Theiler's virus variant produces an altered disease pattern in the mouse central nervous system. J Virol. 1989; 63:1505-1513).

Example 2

Virus Modification

In the first modification step, the virus was propagated in tumour cell lines attenuated by an anticancer agent. Initially, for propagation was used the human breast adenocarcinoma cell culture (MCF-7), cultivated in DME medium (Sigma-Aldrich) with 10% serum (Gibco) and antibiotics (100 IU/ml penicillin, 100 IU/ml streptomycin) at 37° C. under atmosphere, containing 5% $CO_2$ until developing of the monolayer.

The obtained monolayer of these cells was treated with dacarbazine DTIC in sub toxic dose (20 μM). After treating with dacarbazine cells were transferred to fresh culture medium without added serum, the cells contacted with virus and the propagation continued.

After 24 hours from contacting with the virus the cells were removed and virus isolated from the media. The virus was repeatedly propagated in human embryonal fibroblast cell culture and again used for infecting the MCF-7 cell line. This procedure was repeated 10 times.

In the next, second step, the virus as described above, was contacted with gastric adenocarcinoma cell culture. The cell culture for propagation was cultivated in DME medium (Sigma-Aldrich) with 10% serum (Gibco) and antibiotics (100 IU/ml penicillin, 100 IU/ml streptomycin) at 37° C. under atmosphere, containing 5% $CO_2$ until developing of the monolayer.

The obtained monolayer of these cells was treated with dacarbazine DTIC in sub toxic dose (20 μM). After treating with dacarbazine cells were transferred to fresh culture medium without added serum, the cells contacted with virus and the propagation continued.

After 24 hours from contacting with the virus the cells were removed and virus isolated from the media. The virus was repeatedly propagated in human embryonal fibroblast cell culture and again used for infecting the gastric adenocarcinoma cell line. This procedure was repeated 10 times.

In the third step, the virus produced in the second step was used for infecting human tumours, obtained in surgery. Melanoma cancer tissues were obtained in surgery from 23 patients previously treated by chemotherapy.

The tumour cells were separated from fat cells, necrotic tissue and blood, kept at 0° C. for 24 hours, fragmented and as approximately 0.1 $cm^3$ large tissue pieces immersed in Eagle medium (4 ml of medium for 10 mg of tissue), infected with the prepared virus and incubated in the absence of carbon dioxide at 37° C.

The medium was replaced by a fresh portion every day until the destruction of tumour, determined morphologically and visually by the oxidation level of medium.

The virus titer was determined every day in tumor tissue fee medium sample. The reproduction rate of virus was determined from the virus titer at the conclusion of an experiment in comparison with that on Day 0. Such modification of virus was performed in tissues obtained from 23 patients. Before being used for infecting a new tissue material, the modified virus was each time repeatedly propagated in human embryonal fibroblast culture to titer 7 lg $TCID_{50}/1$ ml.

The modified virus was propagated in human embryonal fibroblast cell culture that was treated by 5 mM ribavirin 7 hours before infection and cultivated for 24 hours. Virus was isolated from culture medium, and the procedure repeated 10 times.

Finally, the virus was isolated, purified and propagated in human embryonal fibroblast culture without addition of ribavirin.

The propagated virus sample was used for determination of genome sequence, anticancer activity and replicative stability by passaging it for 12 months in human embryonal fibroblast culture with repeated determination of genome sequence (Seq ID No 1).

Example 3

Determination of Virus Genome Sequence

The isolation, amplification and sequencing of the isolated, modified and cultivated virus genome were performed according to the known method [Chua B H, McMinn P C, Lam S K, Chua K B. Comparison of the complete nucleotide sequences of echovirus 7 strains UMMC and the prototype (Wallace) strain demonstrates significant genetic drift over time. J Gen Virol. 2001 November; 82 (Pt 11): 2629-39].

For this purpose, 96 enteroviruses with complete genome sequence were selected from the NCBI Gene bank. The complete genome sequences for these viruses were downloaded and compared by Vector NTI program. Based on the results of comparing the most conservative regions of virus genomes were determined and 13 degenerated oligonucleotide pairs selected in these regions, covering the length of the potential enteroviruses genome. After the synthesis of the first 13 fragments, another 13 nucleotide pairs were produced. These oligonucleotide pairs were virus-specific and designed so as to produce overlaying fragments. After the building of the full genome sequence the virus genome was repeatedly sequenced with the virus-specific primers.

Example 3.1

The Genome Sequence of the Unmodified (Native) Virus

The sequence of the native virus was produced from 26 separate overlapping PCR fragments, synthesized from the primers listed in Table 2.

TABLE 2

Primers used to sequence the complete genome of viruses.

| Primer | Sequence (5'-3') | Length (bp) | Position | Target region |
|---|---|---|---|---|
| Eo7-1F | TTAAAACAGCCTGTGGGTTG | 20 | 1-20 | 5' UTR |
| Eo7-1R | GAAACACGGACACCCAAAGTAG | 22 | 545-566 | 5' UTR |
| Eo7-2F | CCATGGGACGCTTCAATACT | 20 | 391-410 | 5' UTR |
| Eo7-2R | GCACCAGTCTTTTGTGTCGA | 20 | 758-777 | VP4 |
| Eo7-3F | CGACTACTTTGGGTGTCCGTGTTTC | 25 | 542-566 | 5' UTR |
| Eo7-3R | TCDGGRAAYTTCCACCACCACCC | 23 | 1178-1200 | VP2 |
| Eo7-4F | CGACAGGGTGAGATCCCTAA | 20 | 979-998 | VP2 |
| Eo7-4R | TTTCACCCTTCGTGAGGTTC | 20 | 1381-1400 | VP2 |
| Eo7-5F | GCATCYAARTTYCAYCARGG | 20 | 1289-1308 | VP2 |

TABLE 2-continued

Primers used to sequence the complete genome of viruses.

| Primer | Sequence (5'-3') | Length (bp) | Position | Target region |
|---|---|---|---|---|
| Eo7-5R | CACATKGGKGCAATSGTGAC | 20 | 1676-1695 | VP2 |
| Eo7-6F | GTGGATCAACTTGCGCACTA | 20 | 1513-1532 | VP2 |
| Eo7-6R | AAATTGTGGCATAGCCGAAG | 20 | 1797-1816 | VP3 |
| Eo7-7F | GTCACSATTGCMCCMATGTG | 20 | 1676-1695 | VP2 |
| Eo7-7R | CTTNATRCTYCCTGACCAGTGTG | 23 | 2055-2077 | VP3 |
| Eo7-8F | AAGCATGGACGCATATCACA | 20 | 1921-1940 | VP3 |
| Eo7-8R | GATATGGGTTCCCACATTGC | 20 | 2174-2194 | VP3 |
| Eo7-9F | CACACTGGTCAGGRAGYATNAAG | 23 | 2055-2077 | VP3 |
| Eo7-10F | CAAGTGTGTCGTCCTGTGCT | 20 | 2350-2369 | VP3 |
| Eo7-9R | CCTATTGGCGCTGTCTTGAT | 20 | 2694-2713 | VP1 |
| Eo7-11F | ACCAAAGATCAAGACAGCGC | 20 | 2687-2706 | VP1 |
| Eo7-11R | TTGGCACCCACACTCTGATA | 20 | 3178-3197 | VP1 |
| Eo7-12F | ACCAGTCCGGTGCTGTTTAC | 20 | 3336-3355 | VP1-2A |
| Eo7-12R | TCCCAYACACARTTYTGCCAGTC | 23 | 3401-3423 | 2A |
| Eo7-13F | CARAAYTGTGTGTGGGAAGACTA | 23 | 3407-3429 | 2A |
| Eo7-13R | CCCTGYTCCATKGCTTCATCYTCYARC | 27 | 3748-3774 | 2A-2B |
| Eo7-14F | TTACCCAGTCACCTTCGAGG | 20 | 3535-3554 | 2A |
| Eo7-14R | TGTTTTTCCTTCACTTCCGG | 20 | 4181-4200 | 2C |
| Eo7-15F | GTTRGARGATGATGCNATGGARCARGG | 27 | 3748-3774 | 2A-2B |
| Eo7-15R | TCAATACGGYRTTTGSWCTTGAA | 23 | 4409-4431 | 2C |
| Eo7-16F | CCTYTRTAYGCVGCYGARGC | 20 | 4343-4362 | 2C |
| Eo7-17F | TTCAAGWSCAAAYRCCGTATTGA | 23 | 4409-4431 | 2C |
| Eo7-16R | AAYTGAATGGCCTTHCCACACAC | 23 | 4922-4944 | 2C |
| Eo7-18F | CTDGTGTGTGGRAAGGCYATNCA | 23 | 4919-4941 | 2C |
| Eo7-18R | TATGCTCCYTGRAARCCTGCAAA | 23 | 5309-5330 | 3A-3B |
| Eo7-19F | CAAGCCCTAACCACGTTTGT | 20 | 5252-5271 | 3A |
| Eo7-19R | ACCCGTAGTCAGTCACCTGG | 20 | 5740-5759 | 3C |
| Eo7-20F | TTTGCAGGMTTYCARGGWGCATA | 23 | 5309-5330 | 3A-3B |
| Eo7-20R | GCYCTWGTGGGRAAGTTRTACAT | 23 | 5723-5745 | 3C |
| Eo7-21F | GTGTTGGATGCCAAGGAACT | 20 | 5555-5574 | 3C |
| Eo7-21R | ATGGGCTCCGATCTGATGTC | 20 | 6203-6222 | 3D |
| Eo7-22F | TTCCCCACWAGRGCAGGCCARTGYGG | 26 | 5907-5832 | 3C |
| Eo7-22R | CTCCAAAABASRTCYGGGTCRCA | 23 | 6572-6594 | 3D |
| Eo7-23F | TGAAGGAATGCATGGACAAA | 20 | 6360-6379 | 3D |
| Eo7-23R | ATGGGTATTGCTCATCTGCC | 20 | 7078-7097 | 3D |
| Eo7-24F | TGYGACCCRGAYSTVTTTTGGAG | 23 | 6572-6594 | 3D |
| Eo7-24R | TCRTGDATDTCYTTCATGGGCA | 22 | 7116-7137 | 3D |
| Eo7-25F | CCTGGACGAATGTGACCTTT | 20 | 7041-7060 | 3D |
| Eo7-25R | CCCTACCGCACTTTTATCCA | 20 | 7384-7403 | 3' UTR |
| Eo7-26F | ATCCAYGARTCHATYAGRTGGAC | 23 | 7130-7152 | 3D |
| Eo7-26R | CCGCACCGAATGCGGAGAATTTAC | 24 | 7404-7427 | 3' UTR |

UTR- untranslated region.

The 5'-terminal and the 3'-terminal sequences were obtained, using 5'-RACE and 3'-RACE methods, correspondingly.

As a result, the full genome sequence of the unmodified virus was found to consist of 7434 nucleotides, excluding the poly A sequence (Seq ID No 2). The untranslatable 5'-terminal (5'NTR) contains 742 nucleotides, followed by coding part starting with start codon (AUG) at position 743, containing codons for 2196 amino acids and ending with stop codon (UAA) at position 7331 (Seq ID No 2). The untranslatable 3'-terminal (3'NTR) of this strain contains 100 nucleotides, followed by poly A sequence.

Example 3.2

The Sequence of the Modified Virus (MV)

The sequence of the starting virus was produced from 26 separate overlapping PCR fragments, synthesized using the primers listed in Table 2.

The 5'-terminal and the 3'-terminal sequences were obtained, using 5'-RACE and 3'-RACE methods, correspondingly.

As a result, the full genome sequence of the modified virus was found to consist of 7427 nucleotides, excluding the poly A sequence (Seq ID No 1). The untranslatable 5'-terminal (5'NTR) of this strain contains 742 nucleotides, followed by the coding sequence. The coding part that contains information about the virus polyprotein, begins with the start codon (AUG) at position 743, contains codons for 2194 amino acids and ends with stop codon (UAA) at position 7325 (Seq ID No 1). The untranslatable 3'-terminal (3'NTR) of this strain contains 100 nucleotides, followed by poly A sequence.

Example 3.3

The Genome Sequence of the Modified Virus after Propagation for 12 Months

The sequence of the modified virus was produced from 26 separate overlapping PCR fragments, synthesized the primers listed in Table 2.

The 5'-terminal and the 3'-terminal sequences of this strain were obtained, using 5'-RACE and 3'-RACE methods, correspondingly.

As a result, the full genome sequence of the modified virus was found to consist of 7427 nucleotides, excluding the poly a sequence (Seq ID No 3). The untranslatable 5'-terminal (5'NTR) contains 742 nucleotides, followed by coding part, starting with start codon (AUG) at position 743, containing codons for 2194 amino acids and ending with stop codon (UAA) at position 7325 (Seq ID No 3). The untranslatable 3'-terminal (3'NTR) of this strain contains 100 nucleotides, followed by poly A sequence.

Example 3.4

Comparison of Genomes of Modified Virus (MV) and Native Strain

Comparison of genomes of modified virus (MV) and starting strain is provided in FIG. 1.

The difference in nucleotide sequence, calculated by programme Vector NTI is substantial, 10% for the complete genome and 12% for the part coding the virus coat proteins. The amino acid sequences for the modified and starting strains are listed in FIG. 2.

Example 3.5

The Genome Sequence of the Modified Virus after Propagation for 12 Months

The changes in the sequence of modified virus (MV) genome after continuous passaging for 12 months did not exceed 0.7% of the initial sequence.

All found changes were one nucleotide replacements, partially the mute mutations (without change of amino acid). If the amino acid was changed, its position was in the genome polymorphic part, evidently without relevant influence on virus activity.

Example 4

Virus Passaging

Virus MV was passaged by known methods and propagated for 12 months in human embryonal lung culture MRC 5 (Instituto Zooprofilattico Sperimentale della Lombardia e dell Emilia, Brescia—Laboratorio Centro Substrati Cellulari, Catalogue No. BS CL 68 (origin: American Type Culture centre Collection, Rockville, Md., USA), free of bacteria, viruses, fungi or mycoplasmas, and later stored frozen at −70° C.

Example 5

Determination of Anti-Cancer Activity of the Modified Virus (MV)

In experiments with cell lines, MV was found to cytotoxic for melanoma cell lines FM9, FM55, FM94 and SK-Mel26, gastric carcinoma cells, human oral squamous cell carcinoma SCC25 cells, human epithelial cell line derived from a lung carcinoma (A549), acute monocyte leukemia THP-1 cells, rabdomiosarcoma RD cells, human pancreatic adenocarcinoma HPAF-II cells, human breast adenocarcinoma cells (MCF-7) as well as on primary cell cultures of gastric adenocarcinoma GC1 and thyroid cancer line HA007. Thus, for example, MV injections for 3 days caused reducing of sarcoma M-1 mass in 55% (in 11 of 22) of animals, compared with 6% (in 1 of 18) spontaneous regression in the control group.

Transplanting sarcoma KRS-321 on Day 5 after the injecting MV in a dose $15\times10^6$ $TCID_{50}$ on Wistar rats in 44% of animals (11/25) the regression of tumour was observed, while in the control group there were no cases of regression.

Testing the anti-cancer activity of the virus sample after the 12 months passaging on the same cancer cell lines and transplanted tumours no statistically significant difference from the original MV was observed.

Neither MV nor the virus passaged for 12 months caused any toxic reactions in intact mice.

Example 6

Anti-Cancer Activity of Modified Virus in Treating Patients

Treating of melanoma patients by the modified virus (MV) was conducted according to the following scheme: therapy was commenced 2-3 weeks after the excision of the tumour by intramuscular administration of 2 ml of solution with titer $2\times10^6$ $TCID_{50}$/ml-$2\times10^8$ $TCID_{50}$/ml for 3 days consecutively with supporting injections at monthly intervals according to the same 3 day schedule. After the fourth month, the virus preparation was administered once monthly for the next 8 months. In the next 2 years the supporting therapy was continued with the same dose, gradually increasing the interval between administrations to 6, 8 and 12 weeks.

In a clinical pilot study, a group of 46 melanoma stage I patients no progress of melanoma was observed for 50 months in 43 patients, treated with MV. In the control group, melanoma progressed for 10 of 31 patients undergoing standard therapy.

In a 50 months study of 44 stage II melanoma patients the progress of melanoma was stopped in 38 patients, compared to control group of 36 patients undergoing standard therapy, where melanoma did not progress in 15 patients, but did progress in 21 patients.

The efficiency of treatment is characterized by the following examples:

Case 1. Female, age 76, Melanoma cutis dorsi

Op. 11 Sep. 2009. Excisio to cutis dorsi pT4b N0 M0
SN biopsy was not performed
Ex consilio: follow-up
Op. Jul. 4 2010. LAE *axillaris sin.*
Mts l/n *axillaris sin*
Ex consilio: Roferon
Roferon 6 mil 3× per week from 24 Jun. 2010 till 30 Aug. 2010.
The treatment was discontinued due to the side effects.
From October 2010 the therapy with virus preparation in 2 ml dose with titer $2\times10^6$ $TCID_{50}$/ml-$2\times10^8$ $TCID_{50}$/ml was commenced. The treatment was well tolerated, and no progression of the disease was documented until 1 Feb. 2012.
Case 2. Female, age 42, Melanoma cutis dorsi
Op. 25 May 2008. Excisio tu cutis dorsi
pT4a N0 M0, Clark V, Breslow 9 mm
SN biopsy was not performed
Virus preparation (2 ml with titer $2\times10^6$ $TCID_{50}$/ml-$2\times10^8$ $TCID_{50}$/ml was administered from 27 Jun. 2008 till 27 Jun. 2011.
21 Jan. 2011. US examination: recurrence in the scar
Op. 2 Feb. 2011. Excisio. Histological examination: granuloma.
Virus preparation (2 ml with titer $2\times10^6$ $TCID_{50}$/ml-$2\times10^8$ $TCID_{50}$/ml was continued till 27 Jun. 2011.
During the observation period (till December 2011) no evidence of the disease progression was documented.
Case 3. Female, age 57, Melanoma cutis dorsi
Op. 19 Aug. 2007. Excisio tu cutis dorsi
P T3b N0 M0
SN biopsy was not performed
Recommendations: follow-up
Op. 10 Dec. 2009. LAE colli dx. Histological examination: mts l/n colli dx Progression of the disease—US examination on 22 Feb. 2010: mts l/n colli 22 Feb. 2010. Ex consilio: no surgery was recommended due to bulky disease Virus preparation (2 ml with titer $2\times10^6$ $TCID_{50}$/ml-$2\times10^8$ $TCID_{50}$/ml was administered from 22 Feb. 2010 and still is in progress.
Last visit at clinic on 22 Nov. 2011—the disease has stabilized.
Case 4. Female, age 58, Melanoma cutis dorsi
Op. April 2004. Excisio tu cutis dorsi, LAE *axillaris sin.*
pT4b, N2c, M0 (Breslow 15 mm)
Reexcisio January 2006, September 2006 (local recurrence)
Therapy with IFN from October 2006 till May 2007.
Reexcisio cum dermoplasticum February 2007, May 2007, September 2007.
Virus preparation (2 ml with titer $2\times10^6$ $TCID_{50}$/ml-$2\times10^8$ $TCID_{50}$/ml was administrated from February 2008 till April 2011.
Visceral metastasis February 2011.
Exitus letalis October 2011.
Dose Form and Administration
The viral preparation for therapeutic treatment can be in the form of injectable aqueous solution containing the modified virus having the stable genome sequence as explained above, for example in the titer of $2\times10^6$ $TCID_{50}$/ml-$2\times10^8$ $TCID_{50}$/ml. The solution carrying the virus can be any physiologically acceptable sterile solution, especially sodium chloride solution. The preparation is stored and transported in frozen condition and defrozen at room temperature before the use. The preparation can be in vials or other container units in volumes that correspond a single dose injected at a time to the patient.

The preparation can be administered by injecting it intramuscularly (i.m.) to the patient after the excision of the tumour in question, when the wound has healed. The dosage can be 2 ml of the above-mentioned solution at a time The intramuscular administration by injection is repeated according to the planned therapy schedule.

The invention claimed is:

1. A modified enterovirus of ECHO 7 type, having the genome sequence of SEQ ID No 1.

2. A modified enterovirus having a genome sequence having at least 99% sequence identity to SEQ ID No 1.

* * * * *

SEQUENCE LISTING

```
<160> NUMBER OF SEQ ID NOS: 55

<210> SEQ ID NO 1
<211> LENGTH: 7427
<212> TYPE: RNA
<213> ORGANISM: Enterovirus sp. Echo 7
<220> FEATURE:
<221> NAME/KEY: CDS
<222> LOCATION: (743)..(7327)
<223> OTHER INFORMATION: Modified virus

<400> SEQUENCE: 1
uuaaaacagc cuguggguug uucccaccca cagggcccac ugggcgcuag cacacuggua     60
ucacgguacc cuugugcgcc uguuuuaucu uccccucccc acuguaacuu agaagaauga    120
cauaaacggu caacagauag cucaguacac caacugagcc ccgaccaagc acuucuguua    180
ccccggaccg aguaacaaua ggcugcucgc gcggcugaag gugaaaacgu ucguuacccg    240
gccaauuacu ucgagaaacc uaguaccacc augaagguug cgcagcguuu cgcuccgcac    300
aaccccagug uagaucaggu cgaugaguca ccgcacuccc cacgggcgac cguggcggug    360
gcugcgcugg cggccugccu auggggcaac ccaugggacg cuucaauacu gacauggugc    420
gaagagucua uugagcuaau ugguaguccu ccggccccug aaugcggcua auccuaacug    480
cggggcaagu gcccacaaac caguggguggg cuugucguaa cggguaaccc ugcagcggaa    540
ccgacuacuu ugggguguccg uguuuccuuu uauucuuauu cuggcugcuu auggugacaa    600
```

-continued

```
uugagagauu guurccauau agcuauugga uuggccrucu ggugaguaac agagcaauca    660
uauuccucuu uguuggauuu auaccacuug auuccacuag uuacaacacu cugcuacaua    720
uuauuugcuu aaauacaaga ag aug gga gca caa gua ucg aca caa aag acu    772
                         Met Gly Ala Gln Val Ser Thr Gln Lys Thr
                          1               5                  10 ggu gca cac gag acc sgu uug agc gcu aac gga cac ucu auc auu cac    820
Gly Ala His Glu Thr Xaa Leu Ser Ala Asn Gly His Ser Ile Ile His
                 15                  20                  25 uau acc aac auc aac uac uac aaa gau gca gca ucc aac uca gcc aac    868
Tyr Thr Asn Ile Asn Tyr Tyr Lys Asp Ala Ala Ser Asn Ser Ala Asn
                 30                  35                  40 agg cag gau uuc acc cag gau cca ggu aag uuc acu gaa ccg guc aag    916
Arg Gln Asp Phe Thr Gln Asp Pro Gly Lys Phe Thr Glu Pro Val Lys
             45                  50                  55 gau auc aug auc aaa ucg aug ccc gcc cua aac uca ccg ucc gcg gag    964
Asp Ile Met Ile Lys Ser Met Pro Ala Leu Asn Ser Pro Ser Ala Glu
         60                  65                  70 gag ugc ggg uac agc gac agg gug aga ucc cua acg cuc ggc aac uca   1012
Glu Cys Gly Tyr Ser Asp Arg Val Arg Ser Leu Thr Leu Gly Asn Ser
75                   80                  85                  90 acc auu acc acu caa gaa agu gca aac gua guu guu ggc uau ggc agg   1060
Thr Ile Thr Thr Gln Glu Ser Ala Asn Val Val Val Gly Tyr Gly Arg
                 95                 100                 105 ugg cca gag uac uug aaa gau gaa gaa gcu acu gcg gaa gau cag cca   1108
Trp Pro Glu Tyr Leu Lys Asp Glu Glu Ala Thr Ala Glu Asp Gln Pro
             110                 115                 120 aca caa ccc gau gua gcc acr ugc agg uuc uac acg uug gaa ucc guc   1156
Thr Gln Pro Asp Val Ala Xaa Cys Arg Phe Tyr Thr Leu Glu Ser Val
         125                 130                 135 cag ugg gag aaa aau agc gcu gga ugg ugg ugg aag uuc ccc gaa gca   1204
Gln Trp Glu Lys Asn Ser Ala Gly Trp Trp Trp Lys Phe Pro Glu Ala
     140                 145                 150 cuu aag gac aug ggc cuc uuu ggu cag aac aug cuu uac cac uau cuc   1252
Leu Lys Asp Met Gly Leu Phe Gly Gln Asn Met Leu Tyr His Tyr Leu
155                 160                 165                 170 ggu aga gca ggc uac acu aua cau gug cag ugc aac gca ucc aaa uuu   1300
Gly Arg Ala Gly Tyr Thr Ile His Val Gln Cys Asn Ala Ser Lys Phe
                 175                 180                 185 cau cag ggc ugu cua cuu guu guc ugu gua ccu gaa gcu gag aug ggg   1348
His Gln Gly Cys Leu Leu Val Val Cys Val Pro Glu Ala Glu Met Gly
             190                 195                 200 ugu ucc cag acg gac aaa gag guu gcu gcg aug aac cuc acg aag ggu   1396
Cys Ser Gln Thr Asp Lys Glu Val Ala Ala Met Asn Leu Thr Lys Gly
         205                 210                 215 gaa acg gcg cac aag uuu gaa cca acc aaa acc aca ggc ggc cac aca   1444
Glu Thr Ala His Lys Phe Glu Pro Thr Lys Thr Thr Gly Gly His Thr
     220                 225                 230 gug caa ucc aua gug ugc aac gcg ggu aug ggc auc ggc gug ggg aac   1492
Val Gln Ser Ile Val Cys Asn Ala Gly Met Gly Ile Gly Val Gly Asn
235                 240                 245                 250 cuc acc auc uac ccu cac cag ugg auc aac uug cgc acu aau aac ugc   1540
Leu Thr Ile Tyr Pro His Gln Trp Ile Asn Leu Arg Thr Asn Asn Cys
                 255                 260                 265 gcu aca auu gug aug ccg uau aua aau uca gua ccc aug gau aac aug   1588
Ala Thr Ile Val Met Pro Tyr Ile Asn Ser Val Pro Met Asp Asn Met
             270                 275                 280 uuu agg cac uac aau uuc acg cua aug gug auc cca uuu gca ccc cug   1636
Phe Arg His Tyr Asn Phe Thr Leu Met Val Ile Pro Phe Ala Pro Leu
```

-continued

```
                  285                 290                 295
gau uac aau gcc caa gca ucu gag uac gua ccu gua acu guc aca aua       1684
Asp Tyr Asn Ala Gln Ala Ser Glu Tyr Val Pro Val Thr Val Thr Ile
    300                 305                 310 gcc cca aug ugu gca gaa uac aau ggu uua agg cug gcu uac cag caa       1732
Ala Pro Met Cys Ala Glu Tyr Asn Gly Leu Arg Leu Ala Tyr Gln Gln
315                 320                 325                 330 ggg cug cca gug cua aau aca ccg gga agc aau cag uuu aug aca ucg       1780
Gly Leu Pro Val Leu Asn Thr Pro Gly Ser Asn Gln Phe Met Thr Ser
                335                 340                 345 gau gau uuu caa ucc ccu ucg gcu aug cca caa uuu gau gug acu ccg       1828
Asp Asp Phe Gln Ser Pro Ser Ala Met Pro Gln Phe Asp Val Thr Pro
        350                 355                 360 cac aug gac auc cca ggu gaa gug cac aac cuc aug gag auu gca gaa       1876
His Met Asp Ile Pro Gly Glu Val His Asn Leu Met Glu Ile Ala Glu
            365                 370                 375 guu gau ucg gug gua ccu guu aac aac acu gcg gcc aau cug caa agc       1924
Val Asp Ser Val Val Pro Val Asn Asn Thr Ala Ala Asn Leu Gln Ser
    380                 385                 390 aug gac gca uau cac aua gag gug aac rca gga aau cac caa ggu gaa       1972
Met Asp Ala Tyr His Ile Glu Val Asn Xaa Gly Asn His Gln Gly Glu
395                 400                 405                 410 aag aua uuc gcu uuc cag aua caa ccc ggg cug gau uca gug uuu aag       2020
Lys Ile Phe Ala Phe Gln Ile Gln Pro Gly Leu Asp Ser Val Phe Lys
                415                 420                 425 aga aca cug cua ggu gaa gug cuc aau uau uac gcg cac ugg uca ggg       2068
Arg Thr Leu Leu Gly Glu Val Leu Asn Tyr Tyr Ala His Trp Ser Gly
        430                 435                 440 agc auu aag cua aca uuc aca uuu ugu ggu uca gca aug gcc acg ggc       2116
Ser Ile Lys Leu Thr Phe Thr Phe Cys Gly Ser Ala Met Ala Thr Gly
            445                 450                 455 aag cua cuc uua gca uac ucc cca ccu ggc gcc gau gua ccg gcu agc       2164
Lys Leu Leu Leu Ala Tyr Ser Pro Pro Gly Ala Asp Val Pro Ala Ser
    460                 465                 470 aga aag cag gca aug aug gga acc cau auc auc ugg gac uua ggg cug       2212
Arg Lys Gln Ala Met Met Gly Thr His Ile Ile Trp Asp Leu Gly Leu
475                 480                 485                 490 caa ucc agu ugc guu cua ugu auu cca ugg auc agu cag aca cau uau       2260
Gln Ser Ser Cys Val Leu Cys Ile Pro Trp Ile Ser Gln Thr His Tyr
                495                 500                 505 cgc cua gug caa cag gau gag uac acc agc gcc ggc aau guc acc ugc       2308
Arg Leu Val Gln Gln Asp Glu Tyr Thr Ser Ala Gly Asn Val Thr Cys
        510                 515                 520 ugg uau cag aca ggu aua gug guu cca ccc ggc aca ccc aac aag ugu       2356
Trp Tyr Gln Thr Gly Ile Val Val Pro Pro Gly Thr Pro Asn Lys Cys
            525                 530                 535 guc guc cug ugc uuu gug uca gcg ugu aau gac uuc ucc gug cgc aug       2404
Val Val Leu Cys Phe Val Ser Ala Cys Asn Asp Phe Ser Val Arg Met
    540                 545                 550 cug cgu gac aca cca uuc auc ggc caa aca aca cug cua caa ggu gau       2452
Leu Arg Asp Thr Pro Phe Ile Gly Gln Thr Thr Leu Leu Gln Gly Asp
555                 560                 565                 570 acg gac gug gcc guc aac aau gca gua gcc agg gua gcu gau aca auu       2500
Thr Asp Val Ala Val Asn Asn Ala Val Ala Arg Val Ala Asp Thr Ile
                575                 580                 585 gcc agu ggg ccc agc aac ucc acu agc auu ccu gca cua acc gca guu       2548
Ala Ser Gly Pro Ser Asn Ser Thr Ser Ile Pro Ala Leu Thr Ala Val
        590                 595                 600 gag acu ggg cac aca uca cag gua gag ccu agu gau aca aug caa aca       2596
```

```
                    Glu Thr Gly His Thr Ser Gln Val Glu Pro Ser Asp Thr Met Gln Thr
                            605                 610                 615 cgg cau gua aag aac uac cau ucg cga ucu gaa uca aca aua gag aac                          2644
Arg His Val Lys Asn Tyr His Ser Arg Ser Glu Ser Thr Ile Glu Asn
        620                 625                 630 uuc cuu agc cgg ucg gcc ugu gua uau auu gaa gag uac uuu acc aaa                          2692
Phe Leu Ser Arg Ser Ala Cys Val Tyr Ile Glu Glu Tyr Phe Thr Lys
635                 640                 645                 650 gau caa gac agc gcc aau agg uac aug uca ugg acu aua aau gcu aga                          2740
Asp Gln Asp Ser Ala Asn Arg Tyr Met Ser Trp Thr Ile Asn Ala Arg
                655                 660                 665 agg aug gug caa uug agg cga aag uuu gaa cug uuc aca uac aug cgg                          2788
Arg Met Val Gln Leu Arg Arg Lys Phe Glu Leu Phe Thr Tyr Met Arg
        670                 675                 680 uuu gau aug gag auc aca uuu guu auc acu agu aga caa cug ccu ggg                          2836
Phe Asp Met Glu Ile Thr Phe Val Ile Thr Ser Arg Gln Leu Pro Gly
685                 690                 695 acu agc auc gcg caa gac aug ccg cca cug aca cac caa auc aug uau                          2884
Thr Ser Ile Ala Gln Asp Met Pro Pro Leu Thr His Gln Ile Met Tyr
        700                 705                 710 aua ccc ccu ggu ggu cca gua cca aac agu gug acc gau uuu gca ugg                          2932
Ile Pro Pro Gly Gly Pro Val Pro Asn Ser Val Thr Asp Phe Ala Trp
715                 720                 725                 730 caa acu ucg acu aau cca agu auc uuu ugg acu gag ggc aau gcc ccc                          2980
Gln Thr Ser Thr Asn Pro Ser Ile Phe Trp Thr Glu Gly Asn Ala Pro
                735                 740                 745 ccg cgu aug ucc aua cca uuu aua agc aua ggg aau gca uac agc aac                          3028
Pro Arg Met Ser Ile Pro Phe Ile Ser Ile Gly Asn Ala Tyr Ser Asn
        750                 755                 760 uuu uau gac ggr ugg ucg cac uuc uca caa aau ggg gua uac ggc uac                          3076
Phe Tyr Asp Xaa Trp Ser His Phe Ser Gln Asn Gly Val Tyr Gly Tyr
765                 770                 775 aau gca uua aac aac aug ggc aaa uua uac gca cgc cau gug aac aaa                          3124
Asn Ala Leu Asn Asn Met Gly Lys Leu Tyr Ala Arg His Val Asn Lys
        780                 785                 790 gac aca ccg uac cag aug ucc agu acg auu cgu gug uac uuu aaa ccc                          3172
Asp Thr Pro Tyr Gln Met Ser Ser Thr Ile Arg Val Tyr Phe Lys Pro
795                 800                 805                 810 aaa cau auc aga gug ugg gug cca aga cca cca cgu uug ugc ccu uau                          3220
Lys His Ile Arg Val Trp Val Pro Arg Pro Pro Arg Leu Cys Pro Tyr
                815                 820                 825 auu aaa ucu agu aac guu aac uuu gac cca acc aac cua acu gau uca                          3268
Ile Lys Ser Ser Asn Val Asn Phe Asp Pro Thr Asn Leu Thr Asp Ser
        830                 835                 840 aga uca agu aua aca uau gug cca gac acu auc cgu ccg gaa guc cgu                          3316
Arg Ser Ser Ile Thr Tyr Val Pro Asp Thr Ile Arg Pro Glu Val Arg
845                 850                 855 aca gcu gga aaa uuc ggc cac cag ucc ggu gcu guu uac gug ggu aau                          3364
Thr Ala Gly Lys Phe Gly His Gln Ser Gly Ala Val Tyr Val Gly Asn
                860                 865                 870 uac aga aua gug aac agg cac cuc gcc acg cac aac gac ugg caa aac                          3412
Tyr Arg Ile Val Asn Arg His Leu Ala Thr His Asn Asp Trp Gln Asn
875                 880                 885                 890 ugu gug ugg gaa gac uac aac aga gac cuc cuu gug agc acc acu aca                          3460
Cys Val Trp Glu Asp Tyr Asn Arg Asp Leu Leu Val Ser Thr Thr Thr
                895                 900                 905 gcc cau ggg ugu gac acu aua gcc aga ugu cag ugc aca gca ggc gua                          3508
Ala His Gly Cys Asp Thr Ile Ala Arg Cys Gln Cys Thr Ala Gly Val
        910                 915                 920
```

-continued

| | |
|---|---|
| uau uuu ugu gcc uca agg aac aaa cau uac cca guc acc uuc gag ggg<br>Tyr Phe Cys Ala Ser Arg Asn Lys His Tyr Pro Val Thr Phe Glu Gly<br>     925                   930               935 | 3556 |
| cca ggc uug gug gaa guu cag gag agc gag uac uac cca aaa aga yau<br>Pro Gly Leu Val Glu Val Gln Glu Ser Glu Tyr Tyr Pro Lys Arg Xaa<br>     940                   945               950 | 3604 |
| cag ucc cac gug cuu cua gcu gca gga uuu ucu gaa ccg ggc gau cgu<br>Gln Ser His Val Leu Leu Ala Ala Gly Phe Ser Glu Pro Gly Asp Cys<br>955                   960               965               970 | 3652 |
| ggc gga auc cuc aga ugu caa cac ggc gug auc ggu auc guc acc aug<br>Gly Gly Ile Leu Arg Cys Gln His Gly Val Ile Gly Ile Val Thr Met<br>                      975               980               985 | 3700 |
| ggu gga gag ggg guc guu ggg uuu gcc gac guc aga gac cua cug ugg<br>Gly Gly Glu Gly Val Val Gly Phe Ala Asp Val Arg Asp Leu Leu Trp<br>             990               995               1000 | 3748 |
| uua gag gau gau gcc aug gaa cag ggc gua aga gac uau guu gaa<br>Leu Glu Asp Asp Ala Met Glu Gln Gly Val Arg Asp Tyr Val Glu<br>     1005                  1010                1015 | 3793 |
| caa cua gga aau gcu uuc ggc uca ggu uuc acc aau caa auu ugu<br>Gln Leu Gly Asn Ala Phe Gly Ser Gly Phe Thr Asn Gln Ile Cys<br>     1020                  1025                1030 | 3838 |
| gaa cag guc aac cuc cuc aaa gag uca uug guu gga cag gau ucu<br>Glu Gln Val Asn Leu Leu Lys Glu Ser Leu Val Gly Gln Asp Ser<br>     1035                  1040                1045 | 3883 |
| auu cug gaa aaa ucc cuu aag gcu cua guu aag auu auc uca gca<br>Ile Leu Glu Lys Ser Leu Lys Ala Leu Val Lys Ile Ile Ser Ala<br>     1050                  1055                1060 | 3928 |
| cug guc ruu gua gug aga aau cac gau gau cuc aua acg guu acc<br>Leu Val Xaa Val Val Arg Asn His Asp Asp Leu Ile Thr Val Thr<br>     1065                  1070                1075 | 3973 |
| gcc acu cua gcu uua auu ggu ugc acc ucu ucu ccg ugg cgg ugg<br>Ala Thr Leu Ala Leu Ile Gly Cys Thr Ser Ser Pro Trp Arg Trp<br>     1080                  1085                1090 | 4018 |
| cuc aag cag aag gug uca caa uau uau gga aua ccc agg gcc gag<br>Leu Lys Gln Lys Val Ser Gln Tyr Tyr Gly Ile Pro Arg Ala Glu<br>     1095                  1100                1105 | 4063 |
| cga caa aac aau agc ugg cuc aag aag uuu acu gag aug acc aac<br>Arg Gln Asn Asn Ser Trp Leu Lys Lys Phe Thr Glu Met Thr Asn<br>     1110                  1115                1120 | 4108 |
| gcc ugc aag ggc aug gag ugg aua gcc aua aaa auu caa aag uuu<br>Ala Cys Lys Gly Met Glu Trp Ile Ala Ile Lys Ile Gln Lys Phe<br>     1125                  1130                1135 | 4153 |
| auu gag ugg cuu aaa guc aag auu cug ccg gaa gug aag gaa aaa<br>Ile Glu Trp Leu Lys Val Lys Ile Leu Pro Glu Val Lys Glu Lys<br>     1140                  1145                1150 | 4198 |
| cac gag uuc cuc aac agg cua aag caa uua cca cuc cua gag agc<br>His Glu Phe Leu Asn Arg Leu Lys Gln Leu Pro Leu Leu Glu Ser<br>     1155                  1160                1165 | 4243 |
| cag auu gca acc aua gag cag agu gca cca ucg cag agu gau caa<br>Gln Ile Ala Thr Ile Glu Gln Ser Ala Pro Ser Gln Ser Asp Gln<br>     1170                  1175                1180 | 4288 |
| gag caa cuc uuc ucc aac guc cag uac uuc gcc cau uau ugc aga<br>Glu Gln Leu Phe Ser Asn Val Gln Tyr Phe Ala His Tyr Cys Arg<br>     1185                  1190                1195 | 4333 |
| aag uau gcg cca uug uac gcu gcc gaa gcg aag aga gug uuc uca<br>Lys Tyr Ala Pro Leu Tyr Ala Ala Glu Ala Lys Arg Val Phe Ser<br>     1200                  1205                1210 | 4378 |
| cuu gag aag aaa aug agc aac uac aua cag uuc aag ucc aaa ugc<br>Leu Glu Lys Lys Met Ser Asn Tyr Ile Gln Phe Lys Ser Lys Cys<br>     1215                  1220                1225 | 4423 |

| | | | | | | | | | | |
|---|---|---|---|---|---|---|---|---|---|---|
| cgu | auu | gag | ccu | gua | ugc | uua | cuc | cua | cau | ggc agc cca ggg gcc | 4468
| Arg | Ile | Glu | Pro | Val | Cys | Leu | Leu | Leu | His | Gly Ser Pro Gly Ala |
| | 1230 | | | | 1235 | | | | 1240 | |
| gga | aag | ucc | gug | gcc | acc | aac | uug | auu | ggc | aga ucc cuc gca gaa | 4513
| Gly | Lys | Ser | Val | Ala | Thr | Asn | Leu | Ile | Gly | Arg Ser Leu Ala Glu |
| | 1245 | | | | 1250 | | | | 1255 | |
| aaa | cuc | aac | agc | ucu | gur | uac | ucc | cua | cca | cca gac ccc gac cac | 4558
| Lys | Leu | Asn | Ser | Ser | Xaa | Tyr | Ser | Leu | Pro | Pro Asp Pro Asp His |
| | 1260 | | | | 1265 | | | | 1270 | |
| uuu | gac | ggc | uac | aag | cag | caa | gcg | guc | gug | auc aug gau gac uua | 4603
| Phe | Asp | Gly | Tyr | Lys | Gln | Gln | Ala | Val | Val | Ile Met Asp Asp Leu |
| | 1275 | | | | 1280 | | | | 1285 | |
| ugc | caa | aau | ccu | gau | gga | aaa | gau | guc | uca | cua uuu ugu cag aug | 4648
| Cys | Gln | Asn | Pro | Asp | Gly | Lys | Asp | Val | Ser | Leu Phe Cys Gln Met |
| | 1290 | | | | 1295 | | | | 1300 | |
| guu | ucu | agc | gug | gac | uuu | gua | cca | ccg | aug | gcu gcg cua gag gaa | 4693
| Val | Ser | Ser | Val | Asp | Phe | Val | Pro | Pro | Met | Ala Ala Leu Glu Glu |
| | 1305 | | | | 1310 | | | | 1315 | |
| aaa | gga | auc | cua | uuu | acc | ucc | ccg | uuc | gug | uug gca uca acc aac | 4738
| Lys | Gly | Ile | Leu | Phe | Thr | Ser | Pro | Phe | Val | Leu Ala Ser Thr Asn |
| | 1320 | | | | 1325 | | | | 1330 | |
| gcu | ggg | ucc | auc | aau | gca | ccc | acu | gug | ucu | gac agc aga gcg cuc | 4783
| Ala | Gly | Ser | Ile | Asn | Ala | Pro | Thr | Val | Ser | Asp Ser Arg Ala Leu |
| | 1335 | | | | 1340 | | | | 1345 | |
| gcu | agg | aga | uuc | cac | uuu | gac | aug | aac | auu | gaa guc auu ucu aug | 4828
| Ala | Arg | Arg | Phe | His | Phe | Asp | Met | Asn | Ile | Glu Val Ile Ser Met |
| | 1350 | | | | 1355 | | | | 1360 | |
| uac | agu | caa | aac | ggc | aag | auc | aac | aug | ccc | aug uca guu aaa aca | 4873
| Tyr | Ser | Gln | Asn | Gly | Lys | Ile | Asn | Met | Pro | Met Ser Val Lys Thr |
| | 1365 | | | | 1370 | | | | 1375 | |
| ugu | gau | gaa | gag | ugu | ugu | cca | guu | aac | uuc | aaa agg ugc ugc ccg | 4918
| Cys | Asp | Glu | Glu | Cys | Cys | Pro | Val | Asn | Phe | Lys Arg Cys Cys Pro |
| | 1380 | | | | 1385 | | | | 1390 | |
| uug | gug | ugu | gga | aag | gcy | aug | caa | uuc | auu | gau agg aga acu caa | 4963
| Leu | Val | Cys | Gly | Lys | Ala | Met | Gln | Phe | Ile | Asp Arg Arg Thr Gln |
| | 1395 | | | | 1400 | | | | 1405 | |
| guu | aga | uau | ucg | cug | gac | aug | cua | guu | acu | gaa aug uuu agg gag | 5008
| Val | Arg | Tyr | Ser | Leu | Asp | Met | Leu | Val | Thr | Glu Met Phe Arg Glu |
| | 1410 | | | | 1415 | | | | 1420 | |
| uau | aac | cau | aga | cac | agu | gug | gga | gcc | acu | cuu gaa gcu cug uuc | 5053
| Tyr | Asn | His | Arg | His | Ser | Val | Gly | Ala | Thr | Leu Glu Ala Leu Phe |
| | 1425 | | | | 1430 | | | | 1435 | |
| caa | ggg | cca | cca | guc | uac | aga | gag | auc | aaa | auc agc guc gcc cca | 5098
| Gln | Gly | Pro | Pro | Val | Tyr | Arg | Glu | Ile | Lys | Ile Ser Val Ala Pro |
| | 1440 | | | | 1445 | | | | 1450 | |
| gag | aca | ccc | cca | cca | cca | gcu | auu | gcu | gau | uua cug aaa uca gug | 5143
| Glu | Thr | Pro | Pro | Pro | Pro | Ala | Ile | Ala | Asp | Leu Leu Lys Ser Val |
| | 1455 | | | | 1460 | | | | 1465 | |
| gac | agu | gaa | gcu | gug | agg | gaa | uac | ugc | aag | gag aga ggg ugg cuu | 5188
| Asp | Ser | Glu | Ala | Val | Arg | Glu | Tyr | Cys | Lys | Glu Arg Gly Trp Leu |
| | 1470 | | | | 1475 | | | | 1480 | |
| gug | cca | gag | auc | aau | ucu | acc | cua | caa | aua | gag aag cau gug agu | 5233
| Val | Pro | Glu | Ile | Asn | Ser | Thr | Leu | Gln | Ile | Glu Lys His Val Ser |
| | 1485 | | | | 1490 | | | | 1495 | |
| aga | gca | uuc | aua | ugu | uua | caa | gcc | cua | acc | acg uuu guu uca guu | 5278
| Arg | Ala | Phe | Ile | Cys | Leu | Gln | Ala | Leu | Thr | Thr Phe Val Ser Val |
| | 1500 | | | | 1505 | | | | 1510 | |
| gcu | ggu | aua | aua | uac | auu | auu | uac | aaa | uua | uuu gca ggu uuc caa | 5323
| Ala | Gly | Ile | Ile | Tyr | Ile | Ile | Tyr | Lys | Leu | Phe Ala Gly Phe Gln |

-continued

|  |  |  |  |  |  |  |  |  |  |  |  |
|---|---|---|---|---|---|---|---|---|---|---|---|
| | | | 1515 | | | 1520 | | | 1525 | | |

| ggc | gcc | uac | aca | ggg | aug | ccc | aac | cag | aaa | ccu | aag | gug | ccc | acc | 5368 |
|---|---|---|---|---|---|---|---|---|---|---|---|---|---|---|---|
| Gly | Ala | Tyr | Thr | Gly | Met | Pro | Asn | Gln | Lys | Pro | Lys | Val | Pro | Thr | |
| | | | 1530 | | | 1535 | | | 1540 | | | | | | |

| cug | aga | cag | gcc | aaa | gua | cag | ggc | cca | gcg | uuu | gag | uuc | gcu | gug | 5413 |
| Leu | Arg | Gln | Ala | Lys | Val | Gln | Gly | Pro | Ala | Phe | Glu | Phe | Ala | Val | |
| | 1545 | | | | 1550 | | | | 1555 | | | | | | |

| gcg | aug | aug | aaa | agg | aac | gcc | agu | aca | gua | aaa | acc | gag | uac | ggu | 5458 |
| Ala | Met | Met | Lys | Arg | Asn | Ala | Ser | Thr | Val | Lys | Thr | Glu | Tyr | Gly | |
| | | 1560 | | | | 1565 | | | | 1570 | | | | | |

| gaa | uuc | acc | aug | cuu | ggc | auu | uac | gac | aag | ugg | gcg | gug | uua | ccg | 5503 |
| Glu | Phe | Thr | Met | Leu | Gly | Ile | Tyr | Asp | Lys | Trp | Ala | Val | Leu | Pro | |
| | | 1575 | | | | 1580 | | | | 1585 | | | | | |

| cgc | cac | gcc | aag | ccu | ggc | ccc | acc | auc | uug | aug | aau | gau | cag | gaa | 5548 |
| Arg | His | Ala | Lys | Pro | Gly | Pro | Thr | Ile | Leu | Met | Asn | Asp | Gln | Glu | |
| | | 1590 | | | | 1595 | | | | 1600 | | | | | |

| guc | ggc | gug | uug | gau | gcc | aag | gaa | cua | guu | gau | aaa | gau | ggg | aca | 5593 |
| Val | Gly | Val | Leu | Asp | Ala | Lys | Glu | Leu | Val | Asp | Lys | Asp | Gly | Thr | |
| | 1605 | | | | 1610 | | | | 1615 | | | | | | |

| aau | cua | gaa | uug | acu | cuc | cug | aag | cuc | aac | cgu | aac | gaa | aag | uuc | 5638 |
| Asn | Leu | Glu | Leu | Thr | Leu | Leu | Lys | Leu | Asn | Arg | Asn | Glu | Lys | Phe | |
| | 1620 | | | | 1625 | | | | 1630 | | | | | | |

| aga | gau | auu | agg | ggg | uuu | cua | gca | aga | gaa | gag | guu | gaa | gug | aau | 5683 |
| Arg | Asp | Ile | Arg | Gly | Phe | Leu | Ala | Arg | Glu | Glu | Val | Glu | Val | Asn | |
| | | 1635 | | | | 1640 | | | | 1645 | | | | | |

| gaa | gcu | guc | cua | gca | aua | aau | aca | agc | aaa | uuc | ccu | aac | aug | uac | 5728 |
| Glu | Ala | Val | Leu | Ala | Ile | Asn | Thr | Ser | Lys | Phe | Pro | Asn | Met | Tyr | |
| | | 1650 | | | | 1655 | | | | 1660 | | | | | |

| aua | cca | gug | ggc | cag | gug | acu | gac | uac | ggg | uuu | cug | aac | cug | gga | 5773 |
| Ile | Pro | Val | Gly | Gln | Val | Thr | Asp | Tyr | Gly | Phe | Leu | Asn | Leu | Gly | |
| | | 1665 | | | | 1670 | | | | 1675 | | | | | |

| ggg | acu | ccc | acg | aag | aga | aug | cuc | aug | uau | aac | uuc | cca | acu | aga | 5818 |
| Gly | Thr | Pro | Thr | Lys | Arg | Met | Leu | Met | Tyr | Asn | Phe | Pro | Thr | Arg | |
| | 1680 | | | | 1685 | | | | 1690 | | | | | | |

| gca | ggu | cag | ugu | gga | ggu | guc | cuc | aug | uca | aca | ggg | aaa | guc | cug | 5863 |
| Ala | Gly | Gln | Cys | Gly | Gly | Val | Leu | Met | Ser | Thr | Gly | Lys | Val | Leu | |
| | 1695 | | | | 1700 | | | | 1705 | | | | | | |

| gga | aua | cau | gua | gga | ggg | aau | gga | cau | caa | ggg | uuc | uca | gcg | gca | 5908 |
| Gly | Ile | His | Val | Gly | Gly | Asn | Gly | His | Gln | Gly | Phe | Ser | Ala | Ala | |
| | 1710 | | | | 1715 | | | | 1720 | | | | | | |

| cuc | cuc | agg | cac | uac | uuc | aac | gag | gag | cag | ggu | gaa | aua | gaa | uuc | 5953 |
| Leu | Leu | Arg | His | Tyr | Phe | Asn | Glu | Glu | Gln | Gly | Glu | Ile | Glu | Phe | |
| | 1725 | | | | 1730 | | | | 1735 | | | | | | |

| auu | gag | agc | uca | aag | gac | gcg | gga | uuc | ccu | gug | auc | aac | acu | ccc | 5998 |
| Ile | Glu | Ser | Ser | Lys | Asp | Ala | Gly | Phe | Pro | Val | Ile | Asn | Thr | Pro | |
| | 1740 | | | | 1745 | | | | 1750 | | | | | | |

| agu | aag | aca | aaa | uug | gaa | cca | agu | gug | uuu | cac | cag | gug | uuc | gag | 6043 |
| Ser | Lys | Thr | Lys | Leu | Glu | Pro | Ser | Val | Phe | His | Gln | Val | Phe | Glu | |
| | 1755 | | | | 1760 | | | | 1765 | | | | | | |

| ggc | aac | aag | gaa | cca | gcg | guc | cuu | aga | aau | ggg | gac | cca | cga | cuc | 6088 |
| Gly | Asn | Lys | Glu | Pro | Ala | Val | Leu | Arg | Asn | Gly | Asp | Pro | Arg | Leu | |
| | 1770 | | | | 1775 | | | | 1780 | | | | | | |

| aaa | gcc | aac | uuc | gag | gaa | gca | auc | uuc | ucc | aag | uac | auu | ggc | aau | 6133 |
| Lys | Ala | Asn | Phe | Glu | Glu | Ala | Ile | Phe | Ser | Lys | Tyr | Ile | Gly | Asn | |
| | 1785 | | | | 1790 | | | | 1795 | | | | | | |

| guc | aac | acg | cau | gua | gau | gag | uac | aug | uug | gag | gcu | gug | gac | cau | 6178 |
| Val | Asn | Thr | His | Val | Asp | Glu | Tyr | Met | Leu | Glu | Ala | Val | Asp | His | |
| | 1800 | | | | 1805 | | | | 1810 | | | | | | |

| uau | gca | gga | caa | cua | gcu | acu | cug | gac | auc | agu | acg | gag | ccc | aug | 6223 |

```
Tyr Ala Gly Gln Leu Ala Thr Leu Asp Ile Ser Thr Glu Pro Met
    1815            1820            1825 aag cua gag gac gcc gug uau ggu aca gag ggg cug gaa gca cua       6268
Lys Leu Glu Asp Ala Val Tyr Gly Thr Glu Gly Leu Glu Ala Leu
    1830            1835            1840 gac cua acc acc agu gca ggc uac ccu uac gug gcc cug ggc auc       6313
Asp Leu Thr Thr Ser Ala Gly Tyr Pro Tyr Val Ala Leu Gly Ile
    1845            1850            1855 aag aaa aga gau auu cua ucu aag aag acu aaa gac cuc acu aag       6358
Lys Lys Arg Asp Ile Leu Ser Lys Lys Thr Lys Asp Leu Thr Lys
    1860            1865            1870 uug aag gaa ugc aug gac aaa uau ggc cua aau uug cca aug gua       6403
Leu Lys Glu Cys Met Asp Lys Tyr Gly Leu Asn Leu Pro Met Val
    1875            1880            1885 acc uac guc aaa gau gag uug aga ucu gcu gag aag gug gcc aag       6448
Thr Tyr Val Lys Asp Glu Leu Arg Ser Ala Glu Lys Val Ala Lys
    1890            1895            1900 gga aaa ucc agg cuu auu gag gcu ucu agu cuc aau gac uca gua       6493
Gly Lys Ser Arg Leu Ile Glu Ala Ser Ser Leu Asn Asp Ser Val
    1905            1910            1915 gca aug agg caa aca uuu gga aau uua uau aag acc uuu cac cuc       6538
Ala Met Arg Gln Thr Phe Gly Asn Leu Tyr Lys Thr Phe His Leu
    1920            1925            1930 aac ccg ggc auc guu acg ggc agu gcu guu ggg ugu gau cca gau       6583
Asn Pro Gly Ile Val Thr Gly Ser Ala Val Gly Cys Asp Pro Asp
    1935            1940            1945 gug uuu ugg agc aag auc ccu guu aug cuu gau gga cau cuc aua       6628
Val Phe Trp Ser Lys Ile Pro Val Met Leu Asp Gly His Leu Ile
    1950            1955            1960 gcu uuu gac uau uca ggc uau gac gcu agc cuc agc cca gug ugg       6673
Ala Phe Asp Tyr Ser Gly Tyr Asp Ala Ser Leu Ser Pro Val Trp
    1965            1970            1975 uuu gca ugu uug aaa cuu cuc cua gag aaa cua ggg uau aca aac       6718
Phe Ala Cys Leu Lys Leu Leu Leu Glu Lys Leu Gly Tyr Thr Asn
    1980            1985            1990 aag gaa aca aac uac aua gau uac cuc ugu aau ucc cau cac cug       6763
Lys Glu Thr Asn Tyr Ile Asp Tyr Leu Cys Asn Ser His His Leu
    1995            2000            2005 uau aga gac aag cac uac uuu gua aga ggc ggu aug cca uca ggg       6808
Tyr Arg Asp Lys His Tyr Phe Val Arg Gly Gly Met Pro Ser Gly
    2010            2015            2020 ugu uca ggc acc agc aua uuu aau ucc aug auu aac aac auc aua       6853
Cys Ser Gly Thr Ser Ile Phe Asn Ser Met Ile Asn Asn Ile Ile
    2025            2030            2035 auc agg acu cuc aug cug aag guu uau aaa ggc auu gau uug gac       6898
Ile Arg Thr Leu Met Leu Lys Val Tyr Lys Gly Ile Asp Leu Asp
    2040            2045            2050 caa uuc aga aug auu gcc uau ggg gau gau gug auu gcu ucc uau       6943
Gln Phe Arg Met Ile Ala Tyr Gly Asp Asp Val Ile Ala Ser Tyr
    2055            2060            2065 ccg ugg ccu auc gau gcu ucg cug uua gcu gaa gca gga aaa gau       6988
Pro Trp Pro Ile Asp Ala Ser Leu Leu Ala Glu Ala Gly Lys Asp
    2070            2075            2080 uau ggu uua auc aug acc cca gca gac aaa ggc gag ugc uuc aac       7033
Tyr Gly Leu Ile Met Thr Pro Ala Asp Lys Gly Glu Cys Phe Asn
    2085            2090            2095 gag gua acc ugg acg aau gug acc uuu cug aaa agg uac uuu agg       7078
Glu Val Thr Trp Thr Asn Val Thr Phe Leu Lys Arg Tyr Phe Arg
    2100            2105            2110
```

| | | | | | | | | | | | | | | |
|---|---|---|---|---|---|---|---|---|---|---|---|---|---|---|
| gca | gau | gag | caa | uac | cca | uuu | cug | guc | cau | ccu | guu | aug | cca | aug | 7123 |
| Ala | Asp | Glu | Gln | Tyr | Pro | Phe | Leu | Val | His | Pro | Val | Met | Pro | Met | |
| | 2115 | | | | 2120 | | | | 2125 | | | | | | | aag gac auc cau gag ucu auu agg ugg acc aaa gau ccc aag aac 7168
Lys Asp Ile His Glu Ser Ile Arg Trp Thr Lys Asp Pro Lys Asn
2130 2135 2140 aca cag gau cau gug cgc ucg cug ugc cua uug gcu ugg cac aac 7213
Thr Gln Asp His Val Arg Ser Leu Cys Leu Leu Ala Trp His Asn
2145 2150 2155 ggg gag caa gaa uau gag gag uuu auu cgc aag auc aga agc gug 7258
Gly Glu Gln Glu Tyr Glu Glu Phe Ile Arg Lys Ile Arg Ser Val
2160 2165 2170 ccc guu ggg cgc ugc uug acc cua ccc gcu uuu uca aca cug cgc 7303
Pro Val Gly Arg Cys Leu Thr Leu Pro Ala Phe Ser Thr Leu Arg
2175 2180 2185 agg aag ugg cug gac ucc uuu uaa aauuagagca uaauuaguaa aucauaauug 7357
Arg Lys Trp Leu Asp Ser Phe
2190 gcuuaacccu accgcaugaa ccgaacuuga uaaaagugcg guagggguaa auucuccgca 7417 uucggugcgg 7427

```
<210> SEQ ID NO 2
<211> LENGTH: 7434
<212> TYPE: RNA
<213> ORGANISM: Enterovirus sp. Echo 7
<220> FEATURE:
<221> NAME/KEY: CDS
<222> LOCATION: (743)..(7333)
<223> OTHER INFORMATION: Unmodified (native) virus
<220> FEATURE:
<221> NAME/KEY: misc_feature
<222> LOCATION: (4448)..(4448)
<223> OTHER INFORMATION: n = any nucleotide

<400> SEQUENCE: 2
```
uuaaaacagc cuguggguug uucccaccca cagggcccac ugggcgcuag cacacuggua    60
ucacgguacc uuugugcgcc uguuuuauau cccccuccc acuguaacuu agagaaauca   120
cauaaacgau caauagaagg cgcagcacac cagcugaguc uugaccaagc acuucuguuu   180
ccccggacug aguaucaaua gacugcucac gcgguugaag gagaaaacgu ucguacccg    240 gccaacuacu ucgagaaacc uaguaccacc augaaaguug cgcaguguuu cgcucagcac   300
aaccccagug uagaucaggu cgaugaguca ccgcauuccc cacgggcgac cguggcggug   360
gcugcguugg cggccugccu auggggcaac ccauggacg cuucaauacu gacaugguugc    420 gaagagucua uugagcuagu gguaguccu ccggcccug aaugcggcua auccuaacug     480
cggagcaagu gcccacaaac caguggguag cuugucguaa cggcaacuc ugcagcggaa     540 ccgacuacuu uggguguccg uguuccuuu uauucuuauu cuggcugcuu auggugacaa    600
uugagagauu guuaccauau agcuauugga uuggccaucc ggugacuaac agagcaauca   660
uauuccucuu uguuggauuu auaccacuug auucccacuag uuacaacacu cugcuacaca   720
uuauuuacuu aaaaaccaaga ag aug gga gca caa gua uca aca caa aaa acu    772
                              Met Gly Ala Gln Val Ser Thr Gln Lys Thr
                              1                5                    10 ggu gca cau gag acc sgu uug agc gcu aac gga agc ucc auc auu cac      820
Gly Ala His Glu Thr Xaa Leu Ser Ala Asn Gly Ser Ser Ile Ile His
        15                    20                    25 uac acc aac auc aau uac uac aaa gau gca gca ucc aac uca gcc aac      868
Tyr Thr Asn Ile Asn Tyr Tyr Lys Asp Ala Ala Ser Asn Ser Ala Asn
        30                    35                    40

| | | | | | | | | | | | | | | | |
|---|---|---|---|---|---|---|---|---|---|---|---|---|---|---|---|
| agg | caa | gac | uuc | acc | caa | gau | cca | ggc | aaa | uuc | acc | gaa | ccg | guc | aag | 916 |
| Arg | Gln | Asp | Phe | Thr | Gln | Asp | Pro | Gly | Lys | Phe | Thr | Glu | Pro | Val | Lys |
| | 45 | | | | 50 | | | | 55 | | | | | | |
| gau | auc | aug | auc | aag | ucg | aug | ccc | gcc | cua | aac | uca | ccg | acc | gug | gag | 964 |
| Asp | Ile | Met | Ile | Lys | Ser | Met | Pro | Ala | Leu | Asn | Ser | Pro | Thr | Val | Glu |
| | 60 | | | | 65 | | | | 70 | | | | | | |
| gag | ugu | ggg | uac | agu | gau | agg | gug | aga | ucc | aua | acg | cuc | ggc | aac | uca | 1012 |
| Glu | Cys | Gly | Tyr | Ser | Asp | Arg | Val | Arg | Ser | Ile | Thr | Leu | Gly | Asn | Ser |
| 75 | | | | | 80 | | | | 85 | | | | | | 90 |
| acc | auu | acc | acu | cag | gag | agu | gca | aau | gua | guu | guu | ggc | uau | ggc | ggg | 1060 |
| Thr | Ile | Thr | Thr | Gln | Glu | Ser | Ala | Asn | Val | Val | Val | Gly | Tyr | Gly | Gly |
| | | | | 95 | | | | 100 | | | | | 105 | | |
| ugg | cca | gag | uac | uug | aaa | gau | gaa | gaa | gcu | acu | gcg | gaa | gau | caa | cca | 1108 |
| Trp | Pro | Glu | Tyr | Leu | Lys | Asp | Glu | Glu | Ala | Thr | Ala | Glu | Asp | Gln | Pro |
| | | 110 | | | | 115 | | | | 120 | | | | | |
| aca | caa | ccc | gau | gua | gcc | aca | ugc | agg | uuu | uac | acg | cug | gaa | ucc | guc | 1156 |
| Thr | Gln | Pro | Asp | Val | Ala | Thr | Cys | Arg | Phe | Tyr | Thr | Leu | Glu | Ser | Val |
| | 125 | | | | 130 | | | | 135 | | | | | | |
| cag | ugg | gag | aaa | aau | ucc | gcu | gga | ugg | ugg | ugg | aag | uuc | ccc | gaa | gca | 1204 |
| Gln | Trp | Glu | Lys | Asn | Ser | Ala | Gly | Trp | Trp | Trp | Lys | Phe | Pro | Glu | Ala |
| | 140 | | | | 145 | | | | 150 | | | | | | |
| cuu | aag | gac | aug | ggc | cuc | uuu | ggu | caa | aac | aug | cau | uac | cac | uac | cuc | 1252 |
| Leu | Lys | Asp | Met | Gly | Leu | Phe | Gly | Gln | Asn | Met | His | Tyr | His | Tyr | Leu |
| 155 | | | | | 160 | | | | 165 | | | | | | 170 |
| ggu | aga | gca | ggc | uac | acu | aua | cac | gug | cag | ugc | aau | gca | ucc | aaa | uuc | 1300 |
| Gly | Arg | Ala | Gly | Tyr | Thr | Ile | His | Val | Gln | Cys | Asn | Ala | Ser | Lys | Phe |
| | | | | 175 | | | | 180 | | | | | 185 | | |
| cac | caa | ggc | ugu | cua | cuu | guu | ugc | gua | ccu | gag | gcu | gag | aug | ggg | | 1348 |
| His | Gln | Gly | Cys | Leu | Leu | Val | Cys | Val | Pro | Glu | Ala | Glu | Met | Gly |
| | | | | 190 | | | | 195 | | | | | 200 | | |
| ugu | ucc | aaa | gug | gac | ggu | acu | gua | aau | gag | cag | gaa | uug | acg | gag | ggu | 1396 |
| Cys | Ser | Lys | Val | Asp | Gly | Thr | Val | Asn | Glu | Gln | Glu | Leu | Thr | Glu | Gly |
| | 205 | | | | 210 | | | | | | | 215 | | | |
| gaa | acg | gau | aug | aag | cuu | gaa | ccc | acc | aga | acc | aca | ggc | gua | cgc | cga | 1444 |
| Glu | Thr | Asp | Met | Lys | Leu | Glu | Pro | Thr | Arg | Thr | Thr | Gly | Val | Arg | Arg |
| | 220 | | | | 225 | | | | | | | 230 | | | |
| gug | caa | ucc | gca | gug | uac | aac | gcg | ggu | aug | ggc | guc | ggc | gug | ggg | aac | 1492 |
| Val | Gln | Ser | Ala | Val | Tyr | Asn | Ala | Gly | Met | Gly | Val | Gly | Val | Gly | Asn |
| 235 | | | | 240 | | | | | 245 | | | | | | 250 |
| cuc | acc | auc | uuc | ccu | cac | cag | ugg | auc | aac | cug | cgc | acu | aac | aac | ugu | 1540 |
| Leu | Thr | Ile | Phe | Pro | His | Gln | Trp | Ile | Asn | Leu | Arg | Thr | Asn | Asn | Cys |
| | | | | 255 | | | | 260 | | | | | 265 | | |
| gcu | aca | auu | gug | aug | cca | uac | aua | aau | agu | gua | ccc | aug | gau | aac | aug | 1588 |
| Ala | Thr | Ile | Val | Met | Pro | Tyr | Ile | Asn | Ser | Val | Pro | Met | Asp | Asn | Met |
| | | | 270 | | | | 275 | | | | | 280 | | | |
| uuu | agg | cac | uac | aac | uuc | acg | cua | aug | aug | auc | cca | uuu | gca | ccc | cug | 1636 |
| Phe | Arg | His | Tyr | Asn | Phe | Thr | Leu | Met | Met | Ile | Pro | Phe | Ala | Pro | Leu |
| | 285 | | | | | | 290 | | | | | 295 | | | |
| gau | uac | acc | aac | caa | gca | ucu | acg | uac | gua | ccu | aua | acu | guc | aca | aua | 1684 |
| Asp | Tyr | Thr | Asn | Gln | Ala | Ser | Thr | Tyr | Val | Pro | Ile | Thr | Val | Thr | Ile |
| | 300 | | | | 305 | | | | | | | 310 | | | |
| gca | cca | aug | ugu | gcu | gaa | uac | aau | ggu | uug | agg | cuc | guu | acc | ucg | caa | 1732 |
| Ala | Pro | Met | Cys | Ala | Glu | Tyr | Asn | Gly | Leu | Arg | Leu | Val | Thr | Ser | Gln |
| 315 | | | | 320 | | | | | 325 | | | | | | 330 |
| ggg | uug | cca | gug | aug | aac | aca | ccg | gga | agc | aau | cag | uuc | cug | aca | ucg | 1780 |
| Gly | Leu | Pro | Val | Met | Asn | Thr | Pro | Gly | Ser | Asn | Gln | Phe | Leu | Thr | Ser |
| | | | | 335 | | | | 340 | | | | | 345 | | |
| gau | gac | uuu | caa | uca | ccu | ucg | gcu | aug | cca | caa | uuu | gau | gug | acu | cca | 1828 |
| Asp | Asp | Phe | Gln | Ser | Pro | Ser | Ala | Met | Pro | Gln | Phe | Asp | Val | Thr | Pro |

-continued

|  |  |  |  |  |  |  |  |  |  |  |  |  |  |  |  |
|---|---|---|---|---|---|---|---|---|---|---|---|---|---|---|---|
| | | 350 | | | | 355 | | | | | 360 | | | | |
| gac | aug | gac | auc | cca | ggu | gaa | gug | aac | aac | cuc | aug | gag | auu | gca | gag | 1876
| Asp | Met | Asp | Ile | Pro | Gly | Glu | Val | Asn | Asn | Leu | Met | Glu | Ile | Ala | Glu |
| | | 365 | | | | 370 | | | | 375 | | | | | |
| guu | gac | ucg | gug | gua | ccu | guu | aac | aac | aau | gag | gcc | aau | cug | aaa | agc | 1924
| Val | Asp | Ser | Val | Val | Pro | Val | Asn | Asn | Asn | Glu | Ala | Asn | Leu | Lys | Ser |
| | | 380 | | | | | 385 | | | | 390 | | | | |
| aug | gac | gca | uac | cgc | aua | ccg | gug | aac | rca | gga | aau | caa | caa | ggu | gaa | 1972
| Met | Asp | Ala | Tyr | Arg | Ile | Pro | Val | Asn | Xaa | Gly | Asn | Gln | Gln | Gly | Glu |
| 395 | | | | 400 | | | | | 405 | | | | | 410 | |
| aag | aua | uuu | ggu | uuc | caa | aua | caa | ccc | ggg | cuu | gau | uca | gug | uuu | aag | 2020
| Lys | Ile | Phe | Gly | Phe | Gln | Ile | Gln | Pro | Gly | Leu | Asp | Ser | Val | Phe | Lys |
| | | | | 415 | | | | 420 | | | | | 425 | | |
| aga | aca | cug | cua | ggu | gag | aug | cuc | aau | uau | uac | acg | cac | ugg | uca | ggg | 2068
| Arg | Thr | Leu | Leu | Gly | Glu | Met | Leu | Asn | Tyr | Tyr | Thr | His | Trp | Ser | Gly |
| | | | 430 | | | | | 435 | | | | 440 | | | |
| agc | auu | aag | cua | aca | uuu | aug | uuu | ugu | ggu | uca | gca | aug | gcc | acg | ggc | 2116
| Ser | Ile | Lys | Leu | Thr | Phe | Met | Phe | Cys | Gly | Ser | Ala | Met | Ala | Thr | Gly |
| | | 445 | | | | 450 | | | | | 455 | | | | |
| aaa | uua | cuc | uua | gca | uac | uca | cca | ccu | ggc | gcc | gau | gua | ccg | acu | agc | 2164
| Lys | Leu | Leu | Leu | Ala | Tyr | Ser | Pro | Pro | Gly | Ala | Asp | Val | Pro | Thr | Ser |
| | 460 | | | | | 465 | | | | 470 | | | | | |
| aga | aag | gag | gca | aug | cug | gga | acc | cau | guc | auc | ugg | gac | uuu | ggg | cug | 2212
| Arg | Lys | Glu | Ala | Met | Leu | Gly | Thr | His | Val | Ile | Trp | Asp | Phe | Gly | Leu |
| 475 | | | | 480 | | | | | 485 | | | | | 490 | |
| caa | ucc | agu | ugu | guu | cug | ugu | guu | cca | ugg | auc | agc | cag | aca | cac | uac | 2260
| Gln | Ser | Ser | Cys | Val | Leu | Cys | Val | Pro | Trp | Ile | Ser | Gln | Thr | His | Tyr |
| | | | | 495 | | | | 500 | | | | | 505 | | |
| agg | uug | gug | cag | cag | gau | gag | uac | acc | ggc | gcc | ggc | uau | auc | acc | ugc | 2308
| Arg | Leu | Val | Gln | Gln | Asp | Glu | Tyr | Thr | Gly | Ala | Gly | Tyr | Ile | Thr | Cys |
| | | | 510 | | | | | 515 | | | | 520 | | | |
| ugg | uac | caa | aca | agu | aua | gug | guu | cca | ccc | ggc | aca | ccc | aaa | aag | ugu | 2356
| Trp | Tyr | Gln | Thr | Ser | Ile | Val | Val | Pro | Pro | Gly | Thr | Pro | Lys | Lys | Cys |
| | | 525 | | | | 530 | | | | | 535 | | | | |
| guc | auc | cug | ugc | uuu | gug | uca | gcg | ugu | aau | gau | uuc | ucc | gug | agc | aug | 2404
| Val | Ile | Leu | Cys | Phe | Val | Ser | Ala | Cys | Asn | Asp | Phe | Ser | Val | Ser | Met |
| | 540 | | | | | 545 | | | | 550 | | | | | |
| cug | agu | gac | aca | cca | uuc | auc | ggc | caa | aca | gca | cug | cug | cag | agc | ccu | 2452
| Leu | Ser | Asp | Thr | Pro | Phe | Ile | Gly | Gln | Thr | Ala | Leu | Leu | Gln | Ser | Pro |
| 555 | | | | 560 | | | | | 565 | | | | | 570 | |
| gug | gaa | gaa | gcu | gaa | gag | aac | gca | guu | gca | cgu | gug | gcu | gac | aca | auu | 2500
| Val | Glu | Glu | Ala | Glu | Glu | Asn | Ala | Val | Ala | Arg | Val | Ala | Asp | Thr | Ile |
| | | | | 575 | | | | 580 | | | | | 585 | | |
| gcc | agu | ggg | ccc | agc | aac | ucc | gag | agc | guu | ccu | gca | cua | aca | gca | guu | 2548
| Ala | Ser | Gly | Pro | Ser | Asn | Ser | Glu | Ser | Val | Pro | Ala | Leu | Thr | Ala | Val |
| | | | 590 | | | | | 595 | | | | 600 | | | |
| gag | acu | ggg | cac | aca | uca | cag | gua | gug | ccu | agu | gac | aca | aug | caa | aca | 2596
| Glu | Thr | Gly | His | Thr | Ser | Gln | Val | Val | Pro | Ser | Asp | Thr | Met | Gln | Thr |
| | | 605 | | | | 610 | | | | | 615 | | | | |
| agg | cau | gug | aag | aac | uac | cau | ucg | aga | ucu | gag | uca | aca | aua | gag | aac | 2644
| Arg | His | Val | Lys | Asn | Tyr | His | Ser | Arg | Ser | Glu | Ser | Thr | Ile | Glu | Asn |
| | 620 | | | | | 625 | | | | 630 | | | | | |
| uuc | cuu | agc | agg | ucc | gcc | ugu | gug | uau | auu | gaa | gag | uac | uau | acc | aac | 2692
| Phe | Leu | Ser | Arg | Ser | Ala | Cys | Val | Tyr | Ile | Glu | Glu | Tyr | Tyr | Thr | Asn |
| 635 | | | | 640 | | | | | 645 | | | | | 650 | |
| acu | gaa | acc | aga | caa | aau | uua | uac | aug | uug | ccc | acu | aua | aau | acu | aga | 2740
| Thr | Glu | Thr | Arg | Gln | Asn | Leu | Tyr | Met | Leu | Pro | Thr | Ile | Asn | Thr | Arg |
| | | | | 655 | | | | 660 | | | | | 665 | | |
| ugg | aug | gug | caa | uug | agg | aga | aag | uuu | gag | aug | uuc | aca | uac | aug | agg | 2788

```
                    Trp Met Val Gln Leu Arg Arg Lys Phe Glu Met Phe Thr Tyr Met Arg
                                    670                 675                 680 uuu gac aug gaa auc aca uuu guu auc acu agu aga caa cug cau cga         2836
Phe Asp Met Glu Ile Thr Phe Val Ile Thr Ser Arg Gln Leu His Arg
            685                 690                 695 acu agc aug ccg cag gac aug ccg gua cug aca cac caa auc aug uau         2884
Thr Ser Met Pro Gln Asp Met Pro Val Leu Thr His Gln Ile Met Tyr
700                 705                 710 gua cca ccu ggu ggu cca gua cca aac agu gug gac gau uac gca ugg         2932
Val Pro Pro Gly Gly Pro Val Pro Asn Ser Val Asp Asp Tyr Ala Trp
715                 720                 725                 730 caa acu ucg acu aac cca agu guc uuu ugg acu gag ggc aau gcc cca         2980
Gln Thr Ser Thr Asn Pro Ser Val Phe Trp Thr Glu Gly Asn Ala Pro
                735                 740                 745 ccg cgu aug ucc aua cca uuc aua agc aua ggg aau gca uac agc aac         3028
Pro Arg Met Ser Ile Pro Phe Ile Ser Ile Gly Asn Ala Tyr Ser Asn
            750                 755                 760 uuu uau gau ggg ucc ucg cac uuc uua caa uau ggg gua uau ggc uac         3076
Phe Tyr Asp Gly Ser Ser His Phe Leu Gln Tyr Gly Val Tyr Gly Tyr
765                 770                 775 aac aca uua aac aac aug ggg aaa uua uac gua cgc cau gug aac aac         3124
Asn Thr Leu Asn Asn Met Gly Lys Leu Tyr Val Arg His Val Asn Asn
780                 785                 790 cac aca cca uac caa aug acc agu acg guu agu gug uac uuu aaa ccc         3172
His Thr Pro Tyr Gln Met Thr Ser Thr Val Ser Val Tyr Phe Lys Pro
795                 800                 805                 810 aaa cau guc aga gcg ugg gug ccg aga cca cca cgu cug ugc ccc uac         3220
Lys His Val Arg Ala Trp Val Pro Arg Pro Pro Arg Leu Cys Pro Tyr
            815                 820                 825 aaa aau gca ugg aac guu aac uuu gaa cca aca aac gua acu gau uca         3268
Lys Asn Ala Trp Asn Val Asn Phe Glu Pro Thr Asn Val Thr Asp Ser
            830                 835                 840 aga uca agu auc aca uau auu ccu gag acg guc aaa cca gac cua uca         3316
Arg Ser Ser Ile Thr Tyr Ile Pro Glu Thr Val Lys Pro Asp Leu Ser
        845                 850                 855 aaa gcu gga gcu uuc ggc cac cag ucc ggu gcu guu uau gug ggu aac         3364
Lys Ala Gly Ala Phe Gly His Gln Ser Gly Ala Val Tyr Val Gly Asn
860                 865                 870 uac aga gug gug aau agg cac cuc gcc acg cac aac gac ugg caa aac         3412
Tyr Arg Val Val Asn Arg His Leu Ala Thr His Asn Asp Trp Gln Asn
875                 880                 885                 890 ugu gug ugg gaa gac uac aac aga gac cuc cuu gug agc acc acc aca         3460
Cys Val Trp Glu Asp Tyr Asn Arg Asp Leu Leu Val Ser Thr Thr Thr
            895                 900                 905 gcc cau ggg ugu gac acc aua gcc aga ugc cag ugc aca aca ggc gug         3508
Ala His Gly Cys Asp Thr Ile Ala Arg Cys Gln Cys Thr Thr Gly Val
            910                 915                 920 uac uuu ugu gcc uca agg aac aaa cac uac cca guc acc uuu gag ggg         3556
Tyr Phe Cys Ala Ser Arg Asn Lys His Tyr Pro Val Thr Phe Glu Gly
        925                 930                 935 cca ggc cug gug gaa guu cag gag agu gag uac uac cca aaa aga uac         3604
Pro Gly Leu Val Glu Val Gln Glu Ser Glu Tyr Tyr Pro Lys Arg Tyr
940                 945                 950 caa ucc cau gug cuu cua gcu gca gga uuu ucu gaa cca ggc gau ugu         3652
Gln Ser His Val Leu Leu Ala Ala Gly Phe Ser Glu Pro Gly Asp Cys
955                 960                 965                 970 ggu gga auc cuc agg ugu gaa cau ggu guc auc ggu auc guc acc aug         3700
Gly Gly Ile Leu Arg Cys Glu His Gly Val Ile Gly Ile Val Thr Met
            975                 980                 985
```

-continued

| | | | | | | | | | | | | | |
|---|---|---|---|---|---|---|---|---|---|---|---|---|---|
| ggu | gga | gag | ggg | guc | guu | ggg | uuu | gcc | gac | guc | cga | gac cua | cug ugg | 3748 |
| Gly | Gly | Glu | Gly | Val | Val | Gly | Phe | Ala | Asp | Val | Arg | Asp Leu | Leu Trp |
| | | 990 | | | | 995 | | | | 1000 | | | |

| uua | gag | gau | gau | gcc | aug | gaa | cag | ggc | gua | aga | gac | uau | guu gaa | 3793 |
|---|---|---|---|---|---|---|---|---|---|---|---|---|---|---|
| Leu | Glu | Asp | Asp | Ala | Met | Glu | Gln | Gly | Val | Arg | Asp | Tyr | Val Glu |
| | | 1005 | | | | 1010 | | | | 1015 | | | |

| caa | cua | gga | aau | gcu | uuu | ggc | uca | ggu | uuc | acc | aac | caa | auu ugu | 3838 |
|---|---|---|---|---|---|---|---|---|---|---|---|---|---|---|
| Gln | Leu | Gly | Asn | Ala | Phe | Gly | Ser | Gly | Phe | Thr | Asn | Gln | Ile Cys |
| | | 1020 | | | | 1025 | | | | 1030 | | | |

| gaa | caa | guc | aac | cuc | cuc | aaa | gag | uca | cug | guu | gga | cag | gac ucc | 3883 |
|---|---|---|---|---|---|---|---|---|---|---|---|---|---|---|
| Glu | Gln | Val | Asn | Leu | Leu | Lys | Glu | Ser | Leu | Val | Gly | Gln | Asp Ser |
| | | 1035 | | | | 1040 | | | | 1045 | | | |

| auu | cug | gag | aaa | ucc | cuu | aaa | gcc | cua | guu | aag | auu | auc | uca gca | 3928 |
|---|---|---|---|---|---|---|---|---|---|---|---|---|---|---|
| Ile | Leu | Glu | Lys | Ser | Leu | Lys | Ala | Leu | Val | Lys | Ile | Ile | Ser Ala |
| | | 1050 | | | | 1055 | | | | 1060 | | | |

| cug | guc | auu | gua | gug | aga | aau | cac | gau | gac | cuc | auc | aca | gug acu | 3973 |
|---|---|---|---|---|---|---|---|---|---|---|---|---|---|---|
| Leu | Val | Ile | Val | Val | Arg | Asn | His | Asp | Asp | Leu | Ile | Thr | Val Thr |
| | | 1065 | | | | 1070 | | | | 1075 | | | |

| gcc | acu | cua | gcc | cuc | auu | ggu | ugc | acc | ucu | ucu | cca | ugg | cgg ugg | 4018 |
|---|---|---|---|---|---|---|---|---|---|---|---|---|---|---|
| Ala | Thr | Leu | Ala | Leu | Ile | Gly | Cys | Thr | Ser | Ser | Pro | Trp | Arg Trp |
| | | 1080 | | | | 1085 | | | | 1090 | | | |

| cuc | aaa | cag | aaa | gug | uca | caa | uau | uau | gga | aua | ccc | aug | gcu gag | 4063 |
|---|---|---|---|---|---|---|---|---|---|---|---|---|---|---|
| Leu | Lys | Gln | Lys | Val | Ser | Gln | Tyr | Tyr | Gly | Ile | Pro | Met | Ala Glu |
| | | 1095 | | | | 1100 | | | | 1105 | | | |

| cga | caa | aac | aau | ggc | ugg | cuc | aag | aag | uuc | acu | gag | aug | acc aau | 4108 |
|---|---|---|---|---|---|---|---|---|---|---|---|---|---|---|
| Arg | Gln | Asn | Asn | Gly | Trp | Leu | Lys | Lys | Phe | Thr | Glu | Met | Thr Asn |
| | | 1110 | | | | 1115 | | | | 1120 | | | |

| gcc | ugc | aag | ggc | aug | gag | ugg | aua | gcc | auc | aaa | auu | caa | aaa uuu | 4153 |
|---|---|---|---|---|---|---|---|---|---|---|---|---|---|---|
| Ala | Cys | Lys | Gly | Met | Glu | Trp | Ile | Ala | Ile | Lys | Ile | Gln | Lys Phe |
| | | 1125 | | | | 1130 | | | | 1135 | | | |

| auu | gag | ugg | cuu | aaa | guc | aag | auc | uac | cag | aag | ugu | agg | aaa aac | 4198 |
|---|---|---|---|---|---|---|---|---|---|---|---|---|---|---|
| Ile | Glu | Trp | Leu | Lys | Val | Lys | Ile | Tyr | Gln | Lys | Cys | Arg | Lys Asn |
| | | 1140 | | | | 1145 | | | | 1150 | | | |

| aug | agu | ucc | uca | aca | gac | uau | aac | aac | uac | cac | ucu | ugg | aag agu | 4243 |
|---|---|---|---|---|---|---|---|---|---|---|---|---|---|---|
| Met | Ser | Ser | Ser | Thr | Asp | Tyr | Asn | Asn | Tyr | His | Ser | Trp | Lys Ser |
| | | 1155 | | | | 1160 | | | | 1165 | | | |

| cag | auu | gcc | acc | aua | gaa | caa | agu | gca | cca | ucg | cag | agu | gac cag | 4288 |
|---|---|---|---|---|---|---|---|---|---|---|---|---|---|---|
| Gln | Ile | Ala | Thr | Ile | Glu | Gln | Ser | Ala | Pro | Ser | Gln | Ser | Asp Gln |
| | | 1170 | | | | 1175 | | | | 1180 | | | |

| gag | caa | cug | uuu | ucc | aau | guc | cag | uac | uuc | gcc | cac | uau | ugc aga | 4333 |
|---|---|---|---|---|---|---|---|---|---|---|---|---|---|---|
| Glu | Gln | Leu | Phe | Ser | Asn | Val | Gln | Tyr | Phe | Ala | His | Tyr | Cys Arg |
| | | 1185 | | | | 1190 | | | | 1195 | | | |

| aag | uau | gcg | cca | cug | uau | gca | gcu | gag | gca | aag | aga | gug | uuc ucc | 4378 |
|---|---|---|---|---|---|---|---|---|---|---|---|---|---|---|
| Lys | Tyr | Ala | Pro | Leu | Tyr | Ala | Ala | Glu | Ala | Lys | Arg | Val | Phe Ser |
| | | 1200 | | | | 1205 | | | | 1210 | | | |

| cuu | gag | aag | aaa | aug | agc | aau | uac | aua | cag | uuc | aag | ucc | aaa ugc | 4423 |
|---|---|---|---|---|---|---|---|---|---|---|---|---|---|---|
| Leu | Glu | Lys | Lys | Met | Ser | Asn | Tyr | Ile | Gln | Phe | Lys | Ser | Lys Cys |
| | | 1215 | | | | 1220 | | | | 1225 | | | |

| cgu | auu | gag | ccu | gua | ugu | uug | cuc | nua | cau | ggc | agc | cca | ggg gcc | 4468 |
|---|---|---|---|---|---|---|---|---|---|---|---|---|---|---|
| Arg | Ile | Glu | Pro | Val | Cys | Leu | Leu | Xaa | His | Gly | Ser | Pro | Gly Ala |
| | | 1230 | | | | 1235 | | | | 1240 | | | |

| gga | aaa | ucc | gug | gcc | acc | aac | cug | auu | ggc | aga | uca | cuc | gcu gaa | 4513 |
|---|---|---|---|---|---|---|---|---|---|---|---|---|---|---|
| Gly | Lys | Ser | Val | Ala | Thr | Asn | Leu | Ile | Gly | Arg | Ser | Leu | Ala Glu |
| | | 1245 | | | | 1250 | | | | 1255 | | | |

| aaa | cuc | aac | agc | uca | gug | uac | ucc | cua | cca | cca | gac | cca | gau cac | 4558 |
|---|---|---|---|---|---|---|---|---|---|---|---|---|---|---|
| Lys | Leu | Asn | Ser | Ser | Val | Tyr | Ser | Leu | Pro | Pro | Asp | Pro | Asp His |
| | | 1260 | | | | 1265 | | | | 1270 | | | |

| uuu | gau | ggc | uac | aaa | cag | caa | gcg | guc | gug | auc | aug | gau | gau cua | 4603 |
|---|---|---|---|---|---|---|---|---|---|---|---|---|---|---|
| Phe | Asp | Gly | Tyr | Lys | Gln | Gln | Ala | Val | Val | Ile | Met | Asp | Asp Leu |
| | | 1275 | | | | 1280 | | | | 1285 | | | |

| | | | | | | | | | | | | |
|---|---|---|---|---|---|---|---|---|---|---|---|---|
| ugc | caa | aau | ccu | gau | gga | aaa | gau | gug | uca | uug | uuc | ugu | caa | aug | 4648 |
| Cys | Gln | Asn | Pro | Asp | Gly | Lys | Asp | Val | Ser | Leu | Phe | Cys | Gln | Met | |
| | | 1290 | | | 1295 | | | | 1300 | | | | | | |
| guu | ucc | agu | gug | gac | uuu | gua | cca | ccg | aug | gcu | gcg | cua | gag | gag | 4693 |
| Val | Ser | Ser | Val | Asp | Phe | Val | Pro | Pro | Met | Ala | Ala | Leu | Glu | Glu | |
| | 1305 | | | | 1310 | | | | 1315 | | | | | | |
| aaa | ggc | auu | cug | uuc | acc | ucc | ccg | uuu | guc | cug | gca | uca | acc | aau | 4738 |
| Lys | Gly | Ile | Leu | Phe | Thr | Ser | Pro | Phe | Val | Leu | Ala | Ser | Thr | Asn | |
| | 1320 | | | | 1325 | | | | 1330 | | | | | | |
| gcu | ggg | ucc | auc | aau | gca | cca | acu | gug | uca | gac | agc | aga | gcc | cuc | 4783 |
| Ala | Gly | Ser | Ile | Asn | Ala | Pro | Thr | Val | Ser | Asp | Ser | Arg | Ala | Leu | |
| | 1335 | | | | 1340 | | | | 1345 | | | | | | |
| gcu | agg | aga | uuc | cac | uuu | gac | aug | aac | auu | gaa | guc | auu | ucc | aug | 4828 |
| Ala | Arg | Arg | Phe | His | Phe | Asp | Met | Asn | Ile | Glu | Val | Ile | Ser | Met | |
| | 1350 | | | | 1355 | | | | 1360 | | | | | | |
| uac | agu | caa | aau | ggc | aag | auc | aac | aug | ccc | aug | uca | guu | aag | acg | 4873 |
| Tyr | Ser | Gln | Asn | Gly | Lys | Ile | Asn | Met | Pro | Met | Ser | Val | Lys | Thr | |
| | 1365 | | | | 1370 | | | | 1375 | | | | | | |
| ugu | gau | gaa | gag | ugu | ugu | cca | guc | aac | uuc | aag | agg | ugc | ugc | ccg | 4918 |
| Cys | Asp | Glu | Glu | Cys | Cys | Pro | Val | Asn | Phe | Lys | Arg | Cys | Cys | Pro | |
| | 1380 | | | | 1385 | | | | 1390 | | | | | | |
| cug | gug | ugu | gga | aag | gcc | aug | cag | uuc | auu | gac | aga | aga | acu | caa | 4963 |
| Leu | Val | Cys | Gly | Lys | Ala | Met | Gln | Phe | Ile | Asp | Arg | Arg | Thr | Gln | |
| | 1395 | | | | 1400 | | | | 1405 | | | | | | |
| guu | aga | uac | ucg | cug | gac | aug | cua | guu | acu | gag | aug | uuu | agg | gag | 5008 |
| Val | Arg | Tyr | Ser | Leu | Asp | Met | Leu | Val | Thr | Glu | Met | Phe | Arg | Glu | |
| | 1410 | | | | 1415 | | | | 1420 | | | | | | |
| uac | aac | cac | aga | cac | agu | gug | gga | gcc | acc | cuu | gag | gcu | cug | uuc | 5053 |
| Tyr | Asn | His | Arg | His | Ser | Val | Gly | Ala | Thr | Leu | Glu | Ala | Leu | Phe | |
| | 1425 | | | | 1430 | | | | 1435 | | | | | | |
| caa | ggg | cca | cca | guc | uac | aga | gag | auc | aaa | auu | agu | guc | gca | cca | 5098 |
| Gln | Gly | Pro | Pro | Val | Tyr | Arg | Glu | Ile | Lys | Ile | Ser | Val | Ala | Pro | |
| | 1440 | | | | 1445 | | | | 1450 | | | | | | |
| gag | aca | cca | cca | cca | cca | gcu | auu | gcu | gac | uua | cug | aaa | uca | gug | 5143 |
| Glu | Thr | Pro | Pro | Pro | Pro | Ala | Ile | Ala | Asp | Leu | Leu | Lys | Ser | Val | |
| | 1455 | | | | 1460 | | | | 1465 | | | | | | |
| gac | agu | gaa | gcu | gug | aga | gag | uac | ugc | aaa | gaa | aag | gga | ugg | cuu | 5188 |
| Asp | Ser | Glu | Ala | Val | Arg | Glu | Tyr | Cys | Lys | Glu | Lys | Gly | Trp | Leu | |
| | 1470 | | | | 1475 | | | | 1480 | | | | | | |
| gug | cca | gag | auc | aac | ucc | acc | cua | caa | auu | gag | aag | cau | gug | agc | 5233 |
| Val | Pro | Glu | Ile | Asn | Ser | Thr | Leu | Gln | Ile | Glu | Lys | His | Val | Ser | |
| | 1485 | | | | 1490 | | | | 1495 | | | | | | |
| cgg | gca | uuc | auc | ugu | cug | caa | gca | cua | acc | acg | uuu | guu | uca | guu | 5278 |
| Arg | Ala | Phe | Ile | Cys | Leu | Gln | Ala | Leu | Thr | Thr | Phe | Val | Ser | Val | |
| | 1500 | | | | 1505 | | | | 1510 | | | | | | |
| gcu | gga | aua | aua | uac | auu | auu | uac | aag | cua | uuu | gca | ggu | uuc | caa | 5323 |
| Ala | Gly | Ile | Ile | Tyr | Ile | Ile | Tyr | Lys | Leu | Phe | Ala | Gly | Phe | Gln | |
| | 1515 | | | | 1520 | | | | 1525 | | | | | | |
| ggc | gca | uac | aca | ggg | aug | ccc | aac | cag | aaa | ccc | aag | gug | ccc | acc | 5368 |
| Gly | Ala | Tyr | Thr | Gly | Met | Pro | Asn | Gln | Lys | Pro | Lys | Val | Pro | Thr | |
| | 1530 | | | | 1535 | | | | 1540 | | | | | | |
| cug | aga | caa | gcc | aaa | gug | caa | ggc | cca | gcg | uuu | gag | uuu | gcu | gug | 5413 |
| Leu | Arg | Gln | Ala | Lys | Val | Gln | Gly | Pro | Ala | Phe | Glu | Phe | Ala | Val | |
| | 1545 | | | | 1550 | | | | 1555 | | | | | | |
| gcg | aug | aug | aag | agg | aac | ucc | agu | aca | gug | aaa | acc | gag | uac | ggu | 5458 |
| Ala | Met | Met | Lys | Arg | Asn | Ser | Ser | Thr | Val | Lys | Thr | Glu | Tyr | Gly | |
| | 1560 | | | | 1565 | | | | 1570 | | | | | | |
| gag | uuc | acc | aug | cuu | ggc | auu | uau | gac | agg | ugg | gcg | gug | uua | cca | 5503 |
| Glu | Phe | Thr | Met | Leu | Gly | Ile | Tyr | Asp | Arg | Trp | Ala | Val | Leu | Pro | |

-continued

|  |  |  |  |
|---|---|---|---|
| 1575 | 1580 | 1585 | |

| cgc | cac | gcc | aaa | ccu | ggc | cca | acc | auc | uug | aug | aau | gac | cag | gaa | 5548 |
|---|---|---|---|---|---|---|---|---|---|---|---|---|---|---|---|
| Arg | His | Ala | Lys | Pro | Gly | Pro | Thr | Ile | Leu | Met | Asn | Asp | Gln | Glu | |
| | 1590 | | | | 1595 | | | | 1600 | | | | | | |

| guc | ggc | gug | uug | gau | gcc | aag | gaa | cua | gug | gau | aag | gau | ggg | aca | 5593 |
|---|---|---|---|---|---|---|---|---|---|---|---|---|---|---|---|
| Val | Gly | Val | Leu | Asp | Ala | Lys | Glu | Leu | Val | Asp | Lys | Asp | Gly | Thr | |
| 1605 | | | | | 1610 | | | | | 1615 | | | | | |

| aac | cua | gaa | cug | aca | cuc | cug | aag | cuc | aac | agu | aau | gag | aag | uuc | 5638 |
|---|---|---|---|---|---|---|---|---|---|---|---|---|---|---|---|
| Asn | Leu | Glu | Leu | Thr | Leu | Leu | Lys | Leu | Asn | Ser | Asn | Glu | Lys | Phe | |
| 1620 | | | | | 1625 | | | | | 1630 | | | | | |

| aga | gac | auc | aga | ggg | uuc | cua | gcc | aaa | gaa | gag | guu | gag | gug | aau | 5683 |
|---|---|---|---|---|---|---|---|---|---|---|---|---|---|---|---|
| Arg | Asp | Ile | Arg | Gly | Phe | Leu | Ala | Lys | Glu | Glu | Val | Glu | Val | Asn | |
| | 1635 | | | | 1640 | | | | | 1645 | | | | | |

| gaa | gcu | guc | cua | gca | aua | aac | aca | agc | aag | uuc | ccc | aac | aug | uac | 5728 |
|---|---|---|---|---|---|---|---|---|---|---|---|---|---|---|---|
| Glu | Ala | Val | Leu | Ala | Ile | Asn | Thr | Ser | Lys | Phe | Pro | Asn | Met | Tyr | |
| 1650 | | | | | 1655 | | | | | 1660 | | | | | |

| aua | cca | gug | ggc | cag | gug | acu | gac | uac | ggg | uuc | cug | aac | cug | ggu | 5773 |
|---|---|---|---|---|---|---|---|---|---|---|---|---|---|---|---|
| Ile | Pro | Val | Gly | Gln | Val | Thr | Asp | Tyr | Gly | Phe | Leu | Asn | Leu | Gly | |
| | 1665 | | | | 1670 | | | | | 1675 | | | | | |

| ggg | acg | ccc | acu | aag | aga | aug | cuc | aug | uac | aac | uuc | ccc | acu | aga | 5818 |
|---|---|---|---|---|---|---|---|---|---|---|---|---|---|---|---|
| Gly | Thr | Pro | Thr | Lys | Arg | Met | Leu | Met | Tyr | Asn | Phe | Pro | Thr | Arg | |
| 1680 | | | | | 1685 | | | | | 1690 | | | | | |

| gca | ggu | cag | ugu | ggu | ggu | guc | cuc | aug | ucc | acu | ggg | aaa | guc | cug | 5863 |
|---|---|---|---|---|---|---|---|---|---|---|---|---|---|---|---|
| Ala | Gly | Gln | Cys | Gly | Gly | Val | Leu | Met | Ser | Thr | Gly | Lys | Val | Leu | |
| | 1695 | | | | 1700 | | | | | 1705 | | | | | |

| ggg | aua | cau | guu | ggu | ggg | aau | ggu | cau | caa | ggg | uuc | uca | gca | gca | 5908 |
|---|---|---|---|---|---|---|---|---|---|---|---|---|---|---|---|
| Gly | Ile | His | Val | Gly | Gly | Asn | Gly | His | Gln | Gly | Phe | Ser | Ala | Ala | |
| 1710 | | | | | 1715 | | | | | 1720 | | | | | |

| cuc | cuc | aag | cac | uac | uuc | aac | gau | gaa | caa | ggu | gaa | aua | gag | uuc | 5953 |
|---|---|---|---|---|---|---|---|---|---|---|---|---|---|---|---|
| Leu | Leu | Lys | His | Tyr | Phe | Asn | Asp | Glu | Gln | Gly | Glu | Ile | Glu | Phe | |
| | 1725 | | | | 1730 | | | | | 1735 | | | | | |

| auu | gag | agc | uca | aag | gac | gcg | ggg | uuc | ccu | auc | auc | aac | aca | ccc | 5998 |
|---|---|---|---|---|---|---|---|---|---|---|---|---|---|---|---|
| Ile | Glu | Ser | Ser | Lys | Asp | Ala | Gly | Phe | Pro | Ile | Ile | Asn | Thr | Pro | |
| 1740 | | | | | 1745 | | | | | 1750 | | | | | |

| agc | aag | acc | aaa | cug | gaa | cca | agu | guc | uuc | cac | cag | ugu | uug | aag | 6043 |
|---|---|---|---|---|---|---|---|---|---|---|---|---|---|---|---|
| Ser | Lys | Thr | Lys | Leu | Glu | Pro | Ser | Val | Phe | His | Gln | Cys | Leu | Lys | |
| | 1755 | | | | 1760 | | | | | 1765 | | | | | |

| gca | aca | aag | aac | cca | gca | guc | cuc | aga | aau | ggu | gau | cca | cga | cuc | 6088 |
|---|---|---|---|---|---|---|---|---|---|---|---|---|---|---|---|
| Ala | Thr | Lys | Asn | Pro | Ala | Val | Leu | Arg | Asn | Gly | Asp | Pro | Arg | Leu | |
| 1770 | | | | | 1775 | | | | | 1780 | | | | | |

| aaa | gcc | aac | uuu | gag | gag | gcc | auc | uuc | ucc | aaa | uac | auu | ggc | aau | 6133 |
|---|---|---|---|---|---|---|---|---|---|---|---|---|---|---|---|
| Lys | Ala | Asn | Phe | Glu | Glu | Ala | Ile | Phe | Ser | Lys | Tyr | Ile | Gly | Asn | |
| | 1785 | | | | 1790 | | | | | 1795 | | | | | |

| guc | aac | acg | cau | gug | gau | gag | uac | aug | uug | gaa | gcu | gug | gac | cau | 6178 |
|---|---|---|---|---|---|---|---|---|---|---|---|---|---|---|---|
| Val | Asn | Thr | His | Val | Asp | Glu | Tyr | Met | Leu | Glu | Ala | Val | Asp | His | |
| 1800 | | | | | 1805 | | | | | 1810 | | | | | |

| uau | gca | gga | caa | cug | gcu | acu | cug | gac | auc | agc | acg | gaa | cca | aug | 6223 |
|---|---|---|---|---|---|---|---|---|---|---|---|---|---|---|---|
| Tyr | Ala | Gly | Gln | Leu | Ala | Thr | Leu | Asp | Ile | Ser | Thr | Glu | Pro | Met | |
| | 1815 | | | | 1820 | | | | | 1825 | | | | | |

| aag | cug | gag | gau | gcc | gug | uau | ggu | aca | gag | ggg | cug | gaa | gca | cua | 6268 |
|---|---|---|---|---|---|---|---|---|---|---|---|---|---|---|---|
| Lys | Leu | Glu | Asp | Ala | Val | Tyr | Gly | Thr | Glu | Gly | Leu | Glu | Ala | Leu | |
| 1830 | | | | | 1835 | | | | | 1840 | | | | | |

| gac | cua | aca | acc | agu | gca | ggc | uac | ccu | uau | guu | gcc | cug | ggc | auc | 6313 |
|---|---|---|---|---|---|---|---|---|---|---|---|---|---|---|---|
| Asp | Leu | Thr | Thr | Ser | Ala | Gly | Tyr | Pro | Tyr | Val | Ala | Leu | Gly | Ile | |
| | 1845 | | | | 1850 | | | | | 1855 | | | | | |

| aag | aag | aga | gac | auc | cua | ucu | aag | aag | acc | agg | gac | cuc | acu | aag | 6358 |
|---|---|---|---|---|---|---|---|---|---|---|---|---|---|---|---|
| Lys | Lys | Arg | Asp | Ile | Leu | Ser | Lys | Lys | Thr | Arg | Asp | Leu | Thr | Lys | |
| 1860 | | | | | 1865 | | | | | 1870 | | | | | |

| uug | aaa | gaa | ugc | aug | gac | aag | uau | ggc | cua | aac | cug | cca | aug | gua | 6403 |

-continued

| | | | | | | | | | | | | |
|---|---|---|---|---|---|---|---|---|---|---|---|---|
| Leu | Lys | Glu | Cys | Met | Asp | Lys | Tyr | Gly | Leu | Asn | Leu | Pro | Met | Val |
| | | 1875 | | | | 1880 | | | | 1885 | | |

| acc | uau | gug | aaa | gau | gag | cuc | aga | ucu | gca | gag | aag | gug | gcc | aaa | 6448 |
| Thr | Tyr | Val | Lys | Asp | Glu | Leu | Arg | Ser | Ala | Glu | Lys | Val | Ala | Lys |
| | | 1890 | | | | 1895 | | | | 1900 | | |

| gga | aaa | ucc | agg | cuu | auu | gaa | gcu | ucc | agu | uug | aau | gac | uca | gug | 6493 |
| Gly | Lys | Ser | Arg | Leu | Ile | Glu | Ala | Ser | Ser | Leu | Asn | Asp | Ser | Val |
| | | 1905 | | | | 1910 | | | | 1915 | | |

| gca | aug | aga | cag | aca | uuu | gga | aac | cug | uac | aaa | acc | uuc | cac | cuc | 6538 |
| Ala | Met | Arg | Gln | Thr | Phe | Gly | Asn | Leu | Tyr | Lys | Thr | Phe | His | Leu |
| | | 1920 | | | | 1925 | | | | 1930 | | |

| aac | cca | ggc | auu | gug | acg | ggc | agu | gca | guu | ggu | ugu | gac | cca | gau | 6583 |
| Asn | Pro | Gly | Ile | Val | Thr | Gly | Ser | Ala | Val | Gly | Cys | Asp | Pro | Asp |
| | | 1935 | | | | 1940 | | | | 1945 | | |

| cug | uuu | ugg | agc | aag | aua | cca | guc | aug | uug | gau | gga | cau | cuc | aua | 6628 |
| Leu | Phe | Trp | Ser | Lys | Ile | Pro | Val | Met | Leu | Asp | Gly | His | Leu | Ile |
| | | 1950 | | | | 1955 | | | | 1960 | | |

| gcu | uuu | gau | uac | uca | ggc | uau | gau | gcu | agc | cuc | agc | cca | gug | ugg | 6673 |
| Ala | Phe | Asp | Tyr | Ser | Gly | Tyr | Asp | Ala | Ser | Leu | Ser | Pro | Val | Trp |
| | | 1965 | | | | 1970 | | | | 1975 | | |

| uuu | gca | ugu | cug | aaa | cug | cuc | cua | gag | aag | cuu | ggg | uac | aca | cac | 6718 |
| Phe | Ala | Cys | Leu | Lys | Leu | Leu | Leu | Glu | Lys | Leu | Gly | Tyr | Thr | His |
| | | 1980 | | | | 1985 | | | | 1990 | | |

| aag | gaa | aca | aac | uac | aua | gau | uac | cuc | ugc | aac | ucc | cac | cac | cug | 6763 |
| Lys | Glu | Thr | Asn | Tyr | Ile | Asp | Tyr | Leu | Cys | Asn | Ser | His | His | Leu |
| | | 1995 | | | | 2000 | | | | 2005 | | |

| uac | aga | gac | aaa | cac | uac | uuu | gug | cga | ggu | ggu | aug | cca | uca | ggg | 6808 |
| Tyr | Arg | Asp | Lys | His | Tyr | Phe | Val | Arg | Gly | Gly | Met | Pro | Ser | Gly |
| | | 2010 | | | | 2015 | | | | 2020 | | |

| ugu | ucu | ggc | acc | agc | auc | uuu | aac | uca | aug | auu | aac | aac | auc | aua | 6853 |
| Cys | Ser | Gly | Thr | Ser | Ile | Phe | Asn | Ser | Met | Ile | Asn | Asn | Ile | Ile |
| | | 2025 | | | | 2030 | | | | 2035 | | |

| auc | agg | aca | cuc | aug | cug | aaa | gug | uac | aag | ggc | auu | gac | uug | gac | 6898 |
| Ile | Arg | Thr | Leu | Met | Leu | Lys | Val | Tyr | Lys | Gly | Ile | Asp | Leu | Asp |
| | | 2040 | | | | 2045 | | | | 2050 | | |

| caa | uuc | agg | auu | auu | gcc | uau | ggu | gau | gau | gug | auu | gcu | ucc | uac | 6943 |
| Gln | Phe | Arg | Ile | Ile | Ala | Tyr | Gly | Asp | Asp | Val | Ile | Ala | Ser | Tyr |
| | | 2055 | | | | 2060 | | | | 2065 | | |

| ccg | ugg | ccc | auu | gau | gcu | ucc | cug | cua | gcu | gaa | gca | gga | aaa | gau | 6988 |
| Pro | Trp | Pro | Ile | Asp | Ala | Ser | Leu | Leu | Ala | Glu | Ala | Gly | Lys | Asp |
| | | 2070 | | | | 2075 | | | | 2080 | | |

| uau | ggu | uug | auc | aug | aca | cca | gca | gau | aaa | gga | gag | ugc | uuc | aau | 7033 |
| Tyr | Gly | Leu | Ile | Met | Thr | Pro | Ala | Asp | Lys | Gly | Glu | Cys | Phe | Asn |
| | | 2085 | | | | 2090 | | | | 2095 | | |

| gaa | guc | aac | ugg | acg | aau | guc | acc | uuc | cug | aaa | agg | uac | uuu | aga | 7078 |
| Glu | Val | Asn | Trp | Thr | Asn | Val | Thr | Phe | Leu | Lys | Arg | Tyr | Phe | Arg |
| | | 2100 | | | | 2105 | | | | 2110 | | |

| gca | gau | gag | caa | uac | cca | uuc | cug | guc | cac | ccu | guu | aug | ccc | aug | 7123 |
| Ala | Asp | Glu | Gln | Tyr | Pro | Phe | Leu | Val | His | Pro | Val | Met | Pro | Met |
| | | 2115 | | | | 2120 | | | | 2125 | | |

| aaa | gac | auc | cau | gaa | ucu | auu | aga | ugg | acc | aaa | gau | cca | aag | aac | 7168 |
| Lys | Asp | Ile | His | Glu | Ser | Ile | Arg | Trp | Thr | Lys | Asp | Pro | Lys | Asn |
| | | 2130 | | | | 2135 | | | | 2140 | | |

| acc | caa | gau | cau | gug | cgc | ucg | cug | ugc | cua | uug | gcu | ugg | cac | aau | 7213 |
| Thr | Gln | Asp | His | Val | Arg | Ser | Leu | Cys | Leu | Leu | Ala | Trp | His | Asn |
| | | 2145 | | | | 2150 | | | | 2155 | | |

| ggg | gag | cac | gaa | uau | gag | gag | uuc | auu | cgc | aaa | auc | aga | aag | cgu | 7258 |
| Gly | Glu | His | Glu | Tyr | Glu | Glu | Phe | Ile | Arg | Lys | Ile | Arg | Lys | Arg |
| | | 2160 | | | | 2165 | | | | 2170 | | |

-continued

```
gcc agu ugg  acg cug uuu gac ccu  acc ugc guu uuc aac  ccu gcg      7303
Ala Ser Trp  Thr Leu Phe Asp Pro  Thr Cys Val Phe Asn  Pro Ala
        2175                2180                2185 cag gaa gug  guu gga cuc cuu uua  aaa uaa agcacaauuu aguaaauuug     7353
Gln Glu Val  Val Gly Leu Leu Leu  Lys
        2190                2195 aauuggcuua acccuaccgc acuaaccgaa cuagauaacg gugcgguagg gguaaauucu   7413
ccgcauucgg ugcggucgag g                                             7434

<210> SEQ ID NO 3
<211> LENGTH: 7427
<212> TYPE: RNA
<213> ORGANISM: Enterovirus sp. Echo 7
<220> FEATURE:
<221> NAME/KEY: CDS
<222> LOCATION: (743)..(7327)
<223> OTHER INFORMATION: Modified virus after propagation for 12 months

<400> SEQUENCE: 3
uuaaaacagc cugugggguug uucccaccca cagggcccac ugggcgcuag cacacuggua     60
ucacgguacc cuugugcgcc uguuuuaucu uccccucccc acuguaacuu agaagaauga    120
cauaaacggu caacagauag cucaguacac caacugagcc ccgaccaagc acuucuguua    180
ccccggaccg aguaacaaua ggcugcucgc gcggcugaag gugaaaacgu ucguuacccg    240
gccaauuacu ucgagaaacc uaguaccacc augaagguug cgcagcguuu cgcuccgcac    300
aaccccagug uagaucaggu cgaugaguca ccgcacuccc cacgggcgac cguggcggug    360
gcugcgcugg cggccugccu auggggcaac ccaugggacg cuucaauacu gacauggugc    420
gaagagucua uugagcuaau ugguaguccu ccggccccug aaugcggcua auccuaacug    480
cggggcaagu gcccacaaac cagugggugg cuugucguaa cggguaaccc ugcagcggaa    540
ccgacuacuu ugggguguccg uguuuccuuu uauucuuauu cuggcugcuu auggugacaa    600
uugagagauu guugccauau agcuauugga uuggccaucu ggugaguaac agagcaauca    660
uauuccucuu uguuggauuu auaccacuug auuccacuag uuacaacacu cugcuacaua    720
uuauuugcuu aaauacaaga ag aug gga gca caa gua ucg aca caa aag acu     772
                         Met Gly Ala Gln Val Ser Thr Gln Lys Thr
                         1               5                   10 ggu gca cac gag acc ggu uug agc gcu aac gga cac ucu auc auu cac      820
Gly Ala His Glu Thr Gly Leu Ser Ala Asn Gly His Ser Ile Ile His
                15                  20                  25 uau acc aac auc aac uac uac aaa gau gca gca ucc aac uca gcc aac      868
Tyr Thr Asn Ile Asn Tyr Tyr Lys Asp Ala Ala Ser Asn Ser Ala Asn
            30                  35                  40 agg cag gau uuc acc cag gau cca ggu aag uuc acu gaa ccg guc aag      916
Arg Gln Asp Phe Thr Gln Asp Pro Gly Lys Phe Thr Glu Pro Val Lys
        45                  50                  55 gau auc aug auc aaa ucg aug ccc gcc cua aac uca ccg ucc gcg gag      964
Asp Ile Met Ile Lys Ser Met Pro Ala Leu Asn Ser Pro Ser Ala Glu
    60                  65                  70 gag ugc ggg uac agc gac agg gug aga ucc cua acg yuc ggc aac uca     1012
Glu Cys Gly Tyr Ser Asp Arg Val Arg Ser Leu Thr Xaa Gly Asn Ser
75                  80                  85                  90 acc auu acc acu caa gaa agu gca aac gua guu guu ggc uau ggc agg     1060
Thr Ile Thr Thr Gln Glu Ser Ala Asn Val Val Val Gly Tyr Gly Arg
                95                  100                 105 ugg cca gag uac uug aaa gau gaa gaa gcu acu gcg gaa gau cag cca     1108
Trp Pro Glu Tyr Leu Lys Asp Glu Glu Ala Thr Ala Glu Asp Gln Pro
            110                 115                 120
```

-continued

```
aca caa ccc gau gua gcc aca ugc agg uuc uac acg uug gaa ucc guc      1156
Thr Gln Pro Asp Val Ala Thr Cys Arg Phe Tyr Thr Leu Glu Ser Val
        125                 130                 135 cag ugg gag aaa aau agc gcu gga ugg ugg ugg aag uuc ccc gaa gca      1204
Gln Trp Glu Lys Asn Ser Ala Gly Trp Trp Trp Lys Phe Pro Glu Ala
    140                 145                 150 cuu aag gac aug ggc cuc uuu ggu cag aac aug cuu uac cac uau cuc      1252
Leu Lys Asp Met Gly Leu Phe Gly Gln Asn Met Leu Tyr His Tyr Leu
155                 160                 165                 170 ggu aga gca ggc uac acu aua cau gug cag ugc aac gca ucc aaa uuu      1300
Gly Arg Ala Gly Tyr Thr Ile His Val Gln Cys Asn Ala Ser Lys Phe
                175                 180                 185 cau cag ggc ugu cua cuu guu guc ugu gua ccu gaa gcu gag aug ggg      1348
His Gln Gly Cys Leu Leu Val Val Cys Val Pro Glu Ala Glu Met Gly
            190                 195                 200 ugu ucc cag acg gac aaa gag guu gcu gcg aug aac cuc acg aag ggu      1396
Cys Ser Gln Thr Asp Lys Glu Val Ala Ala Met Asn Leu Thr Lys Gly
        205                 210                 215 gaa acg gcg cac aag uuu gaa cca acc aaa acc aca ggc ggc cac aca      1444
Glu Thr Ala His Lys Phe Glu Pro Thr Lys Thr Thr Gly Gly His Thr
    220                 225                 230 gug caa ucc aua gug ugc aac gcg ggu aug ggc auc ggc gug ggg aac      1492
Val Gln Ser Ile Val Cys Asn Ala Gly Met Gly Ile Gly Val Gly Asn
235                 240                 245                 250 cuc acc auc uac ccu cac cag ugg auc aac uug cgc acu aau aac ugc      1540
Leu Thr Ile Tyr Pro His Gln Trp Ile Asn Leu Arg Thr Asn Asn Cys
                255                 260                 265 gcu aca auu gug aug ccg uau aua aau uca gua ccc aug gau aac aug      1588
Ala Thr Ile Val Met Pro Tyr Ile Asn Ser Val Pro Met Asp Asn Met
            270                 275                 280 uuu agg cac uac aau uuc acg cua aug gug auc cca uuu gca ccc cug      1636
Phe Arg His Tyr Asn Phe Thr Leu Met Val Ile Pro Phe Ala Pro Leu
        285                 290                 295 gau uac aau gcc caa gca ucu gag uac gua ccu gua acu guc aca aua      1684
Asp Tyr Asn Ala Gln Ala Ser Glu Tyr Val Pro Val Thr Val Thr Ile
    300                 305                 310 gcc cca aug ugu gca gaa uac aau ggu uur agg cug gcu uac cag caa      1732
Ala Pro Met Cys Ala Glu Tyr Asn Gly Xaa Arg Leu Ala Tyr Gln Gln
315                 320                 325                 330 ggg cug cca gug cua aau aca ccg gga agc aau cag uuu aug aca ucg      1780
Gly Leu Pro Val Leu Asn Thr Pro Gly Ser Asn Gln Phe Met Thr Ser
                335                 340                 345 gau gau uuu caa ucc ccu ucg gcu aug cca caa uuu gau gug acu ccg      1828
Asp Asp Phe Gln Ser Pro Ser Ala Met Pro Gln Phe Asp Val Thr Pro
            350                 355                 360 cac aug gac auc cca ggu gaa gug cac aac cuc aug gag auu gca gaa      1876
His Met Asp Ile Pro Gly Glu Val His Asn Leu Met Glu Ile Ala Glu
        365                 370                 375 guu gau ucg gug gua ccu guu aac aac acu gcg gcc aau cug caa agc      1924
Val Asp Ser Val Val Pro Val Asn Asn Thr Ala Ala Asn Leu Gln Ser
    380                 385                 390 aug gac gca uau cac aua gag gug aac gca gga aau cac caa ggu gaa      1972
Met Asp Ala Tyr His Ile Glu Val Asn Ala Gly Asn His Gln Gly Glu
395                 400                 405                 410 aag aua uuc gcu uuc cag aua caa ccc ggg cug gau uca gug uuu aag      2020
Lys Ile Phe Ala Phe Gln Ile Gln Pro Gly Leu Asp Ser Val Phe Lys
                415                 420                 425 aga aca cug cua ggu gaa gug cuc aau uau uac gcg cac ugg uca ggg      2068
Arg Thr Leu Leu Gly Glu Val Leu Asn Tyr Tyr Ala His Trp Ser Gly
```

```
                430             435             440
agc auu aag cua aca uuc aca uuu ugu ggu uca gca aug gcc acg ggc      2116
Ser Ile Lys Leu Thr Phe Thr Phe Cys Gly Ser Ala Met Ala Thr Gly
        445             450             455 aag cua cuc uua gca uac ucc cca ccu ggc gcc gau gua ccg gcu agc      2164
Lys Leu Leu Leu Ala Tyr Ser Pro Pro Gly Ala Asp Val Pro Ala Ser
460             465             470 aga aag cag gca aug mug gga acc cau auc auc ugg gac uua ggg cug      2212
Arg Lys Gln Ala Met Xaa Gly Thr His Ile Ile Trp Asp Leu Gly Leu
475             480             485             490 caa ucc agu ugc guu cua ugu auu cca ugg auc agu cag aca cau uau      2260
Gln Ser Ser Cys Val Leu Cys Ile Pro Trp Ile Ser Gln Thr His Tyr
        495             500             505 cgc cua gug caa cag gau gag uac acc agc gcc ggc aau guc acc ugc      2308
Arg Leu Val Gln Gln Asp Glu Tyr Thr Ser Ala Gly Asn Val Thr Cys
        510             515             520 ugg uau cag aca ggu aua gug guu cca ccc ggc aca ccc aac aag ugu      2356
Trp Tyr Gln Thr Gly Ile Val Val Pro Pro Gly Thr Pro Asn Lys Cys
        525             530             535 guc guc cug ugc uuu gug uca gcg ugu aau gac uuc ucc gug cgc aug      2404
Val Val Leu Cys Phe Val Ser Ala Cys Asn Asp Phe Ser Val Arg Met
        540             545             550 cug cgu gac aca cca uuc auc ggc caa aca aca cug cua caa ggu gau      2452
Leu Arg Asp Thr Pro Phe Ile Gly Gln Thr Thr Leu Leu Gln Gly Asp
555             560             565             570 acg gac gug gcc guc aac aau gca gua gcc agg gua gcu gau aca auu      2500
Thr Asp Val Ala Val Asn Asn Ala Val Ala Arg Val Ala Asp Thr Ile
        575             580             585 gcc agu ggg ccc agc aac ucc acu agc auu ccu gca cua acc gca guu      2548
Ala Ser Gly Pro Ser Asn Ser Thr Ser Ile Pro Ala Leu Thr Ala Val
        590             595             600 gag acu ggg cac aca uca cag gua gag ccu agu gau aca aug caa aca      2596
Glu Thr Gly His Thr Ser Gln Val Glu Pro Ser Asp Thr Met Gln Thr
        605             610             615 cgg cau gua aag aac uac cau ucg cga ucu gaa uca aca aua gag aac      2644
Arg His Val Lys Asn Tyr His Ser Arg Ser Glu Ser Thr Ile Glu Asn
        620             625             630 uuc cuu agc cgg ucg gcc ugu gua uau wuu gaa gas uac uuu acc aaa      2692
Phe Leu Ser Arg Ser Ala Cys Val Tyr Xaa Glu Xaa Tyr Phe Thr Lys
635             640             645             650 gau caa gac agc gcc aau agg uac aug uca ugg acu aua aau gcu aga      2740
Asp Gln Asp Ser Ala Asn Arg Tyr Met Ser Trp Thr Ile Asn Ala Arg
            655             660             665 agg aug gug caa uug agg cga aag uuu gaa cug uuc aca uac aug cgg      2788
Arg Met Val Gln Leu Arg Arg Lys Phe Glu Leu Phe Thr Tyr Met Arg
        670             675             680 uuu gau aug gag auc aca uuu guu auc acu agu aga caa cug ccu ggg      2836
Phe Asp Met Glu Ile Thr Phe Val Ile Thr Ser Arg Gln Leu Pro Gly
        685             690             695 acu agc auc gcg caa gac aug ccg cca cug aca cac caa auc aug uau      2884
Thr Ser Ile Ala Gln Asp Met Pro Pro Leu Thr His Gln Ile Met Tyr
700             705             710 aua ccc ccu ggu ggu cca rua cca aac agu gug acc gau uuu gca ugg      2932
Ile Pro Pro Gly Gly Pro Xaa Pro Asn Ser Val Thr Asp Phe Ala Trp
715             720             725             730 caa acu ucg acu aau cca agu auc uuu ugg acu gag ggc aau gcc ccc      2980
Gln Thr Ser Thr Asn Pro Ser Ile Phe Trp Thr Glu Gly Asn Ala Pro
        735             740             745 ccg cgu aug ucc aua cca uuu aua agc aua ggg aau gca uac agc aac      3028
```

```
                Pro Arg Met Ser Ile Pro Phe Ile Ser Ile Gly Asn Ala Tyr Ser Asn
                            750                 755                 760 uuu uau gac gga ugg ucg cac uuc uca caa aau ggg gua uac ggc uac              3076
Phe Tyr Asp Gly Trp Ser His Phe Ser Gln Asn Gly Val Tyr Gly Tyr
            765                 770                 775 aau gca uua aac aac aug ggc aaa uua uac gca cgc cau gug aac aaa              3124
Asn Ala Leu Asn Asn Met Gly Lys Leu Tyr Ala Arg His Val Asn Lys
            780                 785                 790 gac aca ccg uac cag aug ucc agu acg auu cgu gug uac uuu aaa ccc              3172
Asp Thr Pro Tyr Gln Met Ser Ser Thr Ile Arg Val Tyr Phe Lys Pro
795                 800                 805                 810 aaa cau auc aga gug ugg gug cca aga cca cca cgu uug ugc ccc uau              3220
Lys His Ile Arg Val Trp Val Pro Arg Pro Pro Arg Leu Cys Pro Tyr
                815                 820                 825 auu aaa ucu agu aac guu aac uuu gac cca acc aac cua acu gau uca              3268
Ile Lys Ser Ser Asn Val Asn Phe Asp Pro Thr Asn Leu Thr Asp Ser
                830                 835                 840 aga uca agu aua aca uau gug cca gac acu auc cgu ccg gaa guc cgu              3316
Arg Ser Ser Ile Thr Tyr Val Pro Asp Thr Ile Arg Pro Glu Val Arg
                845                 850                 855 aca gcu gga aaa uuc ggc cac cag ucc ggu gcu guu uac gug ggu aau              3364
Thr Ala Gly Lys Phe Gly His Gln Ser Gly Ala Val Tyr Val Gly Asn
                860                 865                 870 uac aga aua gug aac agg cac cuc gcc acg cac aac gac ugg caa aac              3412
Tyr Arg Ile Val Asn Arg His Leu Ala Thr His Asn Asp Trp Gln Asn
875                 880                 885                 890 ugu gug ugg gaa gac uac aac aga gac cuc cuu gug agc acc acu aca              3460
Cys Val Trp Glu Asp Tyr Asn Arg Asp Leu Leu Val Ser Thr Thr Thr
                895                 900                 905 gcc cau ggg ugu gac acu auc gcc aga ugu cag ugc aca gca ggc gua              3508
Ala His Gly Cys Asp Thr Ile Ala Arg Cys Gln Cys Thr Ala Gly Val
                910                 915                 920 uau uuu ugu gcc uca agg aac aaa cau uac cca guc acc uuc gag ggg              3556
Tyr Phe Cys Ala Ser Arg Asn Lys His Tyr Pro Val Thr Phe Glu Gly
                925                 930                 935 cca ggc uug gug gaa guu cag gag agc gag uac uac cca aaa aga uau              3604
Pro Gly Leu Val Glu Val Gln Glu Ser Glu Tyr Tyr Pro Lys Arg Tyr
940                 945                 950 cag ucc cac gug cuu cua gcu gca gga uuu ucu gaa ccg ggc gau ugu              3652
Gln Ser His Val Leu Leu Ala Ala Gly Phe Ser Glu Pro Gly Asp Cys
955                 960                 965                 970 ggc gga auc cuc aga ugu caa cac ggc gug auc ggu auc guc acc aug              3700
Gly Gly Ile Leu Arg Cys Gln His Gly Val Ile Gly Ile Val Thr Met
                975                 980                 985 ggu gga gag ggg guc guu ggg uuu gcc gac guc aga gac cua cug ugg              3748
Gly Gly Glu Gly Val Val Gly Phe Ala Asp Val Arg Asp Leu Leu Trp
                990                 995                 1000 uua gag gau gau gcc aug gaa cag ggc gua aga gac uau guu gaa              3793
Leu Glu Asp Asp Ala Met Glu Gln Gly Val Arg Asp Tyr Val Glu
            1005                1010                1015 caa cua gga aau gcu uuc ggc uca ggu uuc acc aau caa auu ugu              3838
Gln Leu Gly Asn Ala Phe Gly Ser Gly Phe Thr Asn Gln Ile Cys
            1020                1025                1030 gaa cag guc aac cuc cuc aaa gag uca uug guu gga cag gau ucu              3883
Glu Gln Val Asn Leu Leu Lys Glu Ser Leu Val Gly Gln Asp Ser
            1035                1040                1045 auu cug gaa aaa ucc cuu aag gcu cua guu aag auu auc uca gca              3928
Ile Leu Glu Lys Ser Leu Lys Ala Leu Val Lys Ile Ile Ser Ala
            1050                1055                1060
```

| | | | | | | | | | | | | |
|---|---|---|---|---|---|---|---|---|---|---|---|---|
| cug | guc | guu | gua | gug | aga | aau | cac | gau | gau | cuc | aua | acg | guu | acc | 3973 |
| Leu | Val | Val | Val | Val | Arg | Asn | His | Asp | Asp | Leu | Ile | Thr | Val | Thr | |
| | | 1065 | | | | 1070 | | | | | 1075 | | | | |
| gcc | acu | cua | gcu | uua | auu | ggu | ugc | acc | ucu | ucu | ccg | ugg | cgg | ugg | 4018 |
| Ala | Thr | Leu | Ala | Leu | Ile | Gly | Cys | Thr | Ser | Ser | Pro | Trp | Arg | Trp | |
| | | 1080 | | | | 1085 | | | | | 1090 | | | | |
| cuc | aag | cag | aag | gug | uca | caa | uau | uau | gga | aua | ccc | agg | gcc | gag | 4063 |
| Leu | Lys | Gln | Lys | Val | Ser | Gln | Tyr | Tyr | Gly | Ile | Pro | Arg | Ala | Glu | |
| | | 1095 | | | | 1100 | | | | | 1105 | | | | |
| cga | caa | aac | aau | agc | ugg | cuc | aag | aag | uuu | acu | gag | aug | acc | aac | 4108 |
| Arg | Gln | Asn | Asn | Ser | Trp | Leu | Lys | Lys | Phe | Thr | Glu | Met | Thr | Asn | |
| | | 1110 | | | | 1115 | | | | | 1120 | | | | |
| gcc | ugc | aag | ggc | aug | gag | ugg | aua | gcc | aua | aaa | auu | caa | aag | uuu | 4153 |
| Ala | Cys | Lys | Gly | Met | Glu | Trp | Ile | Ala | Ile | Lys | Ile | Gln | Lys | Phe | |
| | | 1125 | | | | 1130 | | | | | 1135 | | | | |
| auu | gag | ugg | cuu | aaa | guc | aag | auu | cug | ccg | gaa | gug | aag | gaa | aaa | 4198 |
| Ile | Glu | Trp | Leu | Lys | Val | Lys | Ile | Leu | Pro | Glu | Val | Lys | Glu | Lys | |
| | | 1140 | | | | 1145 | | | | | 1150 | | | | |
| cac | gag | uuc | cuc | aac | agg | cua | aag | caa | uua | cca | cuc | cuc | gag | agc | 4243 |
| His | Glu | Phe | Leu | Asn | Arg | Leu | Lys | Gln | Leu | Pro | Leu | Leu | Glu | Ser | |
| | | 1155 | | | | 1160 | | | | | 1165 | | | | |
| cag | auu | gca | acc | aua | gag | cag | agu | gca | cca | ucg | cag | agu | gau | caa | 4288 |
| Gln | Ile | Ala | Thr | Ile | Glu | Gln | Ser | Ala | Pro | Ser | Gln | Ser | Asp | Gln | |
| | | 1170 | | | | 1175 | | | | | 1180 | | | | |
| gag | caa | cuc | uuc | ucc | aac | guc | cag | uac | uuc | gcc | cau | uau | ugc | aga | 4333 |
| Glu | Gln | Leu | Phe | Ser | Asn | Val | Gln | Tyr | Phe | Ala | His | Tyr | Cys | Arg | |
| | | 1185 | | | | 1190 | | | | | 1195 | | | | |
| aag | uau | gcg | cca | uug | uac | gcu | gcc | gag | gcg | aag | aga | gug | uuc | uca | 4378 |
| Lys | Tyr | Ala | Pro | Leu | Tyr | Ala | Ala | Glu | Ala | Lys | Arg | Val | Phe | Ser | |
| | | 1200 | | | | 1205 | | | | | 1210 | | | | |
| cuu | gag | aag | aaa | aug | agc | aac | uac | aua | cag | uuc | aag | ucc | aaa | ugc | 4423 |
| Leu | Glu | Lys | Lys | Met | Ser | Asn | Tyr | Ile | Gln | Phe | Lys | Ser | Lys | Cys | |
| | | 1215 | | | | 1220 | | | | | 1225 | | | | |
| cgu | auu | gag | ccu | gua | ugc | uua | cuc | cua | cau | ggc | agc | cca | ggg | gcc | 4468 |
| Arg | Ile | Glu | Pro | Val | Cys | Leu | Leu | Leu | His | Gly | Ser | Pro | Gly | Ala | |
| | | 1230 | | | | 1235 | | | | | 1240 | | | | |
| gga | aag | ucc | gug | gcc | acc | aac | uug | auu | ggc | aga | ucc | cuc | gca | gaa | 4513 |
| Gly | Lys | Ser | Val | Ala | Thr | Asn | Leu | Ile | Gly | Arg | Ser | Leu | Ala | Glu | |
| | | 1245 | | | | 1250 | | | | | 1255 | | | | |
| aaa | cuc | aac | agc | ucu | gua | uac | ucc | cua | cca | cca | gac | ccc | gac | cac | 4558 |
| Lys | Leu | Asn | Ser | Ser | Val | Tyr | Ser | Leu | Pro | Pro | Asp | Pro | Asp | His | |
| | | 1260 | | | | 1265 | | | | | 1270 | | | | |
| uuu | gac | ggc | uac | aag | cag | caa | gcg | guc | gug | auc | aug | gau | gac | uua | 4603 |
| Phe | Asp | Gly | Tyr | Lys | Gln | Gln | Ala | Val | Val | Ile | Met | Asp | Asp | Leu | |
| | | 1275 | | | | 1280 | | | | | 1285 | | | | |
| ugc | caa | aau | ccu | gau | gga | aaa | gau | guc | uca | cua | uuu | ugu | cag | aug | 4648 |
| Cys | Gln | Asn | Pro | Asp | Gly | Lys | Asp | Val | Ser | Leu | Phe | Cys | Gln | Met | |
| | | 1290 | | | | 1295 | | | | | 1300 | | | | |
| guu | ucu | agc | gug | gac | uuu | gua | cca | ccg | aug | gcu | gcg | cua | gag | gaa | 4693 |
| Val | Ser | Ser | Val | Asp | Phe | Val | Pro | Pro | Met | Ala | Ala | Leu | Glu | Glu | |
| | | 1305 | | | | 1310 | | | | | 1315 | | | | |
| aaa | gga | auc | cua | uuu | acc | ucc | ccg | uuc | gug | uug | gca | uca | acc | aac | 4738 |
| Lys | Gly | Ile | Leu | Phe | Thr | Ser | Pro | Phe | Val | Leu | Ala | Ser | Thr | Asn | |
| | | 1320 | | | | 1325 | | | | | 1330 | | | | |
| gcu | ggg | ucc | auc | aau | gca | ccc | acu | gug | ucu | gac | agc | aga | gcg | cuc | 4783 |
| Ala | Gly | Ser | Ile | Asn | Ala | Pro | Thr | Val | Ser | Asp | Ser | Arg | Ala | Leu | |
| | | 1335 | | | | 1340 | | | | | 1345 | | | | |
| gcu | agg | aga | uuc | cac | uuu | gac | aug | aac | auu | gaa | guc | auu | ucu | aug | 4828 |
| Ala | Arg | Arg | Phe | His | Phe | Asp | Met | Asn | Ile | Glu | Val | Ile | Ser | Met | |
| | | 1350 | | | | 1355 | | | | | 1360 | | | | |

```
uac agu caa aac ggc aag auc aac aug ccc aug uca guu aaa aca         4873
Tyr Ser Gln Asn Gly Lys Ile Asn Met Pro Met Ser Val Lys Thr
        1365                1370                1375 ugu gau gaa gag ugu ugu cca guu aac uuc aaa agg ugc ugc ccg         4918
Cys Asp Glu Glu Cys Cys Pro Val Asn Phe Lys Arg Cys Cys Pro
        1380                1385                1390 uug gug ugu ggg aag gcy aug caa uuc auu gau agg aga acu caa         4963
Leu Val Cys Gly Lys Ala Met Gln Phe Ile Asp Arg Arg Thr Gln
        1395                1400                1405 guu aga uau ucg cug gac aug cua guu acu gaa aug uuu agg gag         5008
Val Arg Tyr Ser Leu Asp Met Leu Val Thr Glu Met Phe Arg Glu
        1410                1415                1420 uau aac cau aga cac agu gug gga gcc acu cuu gaa gcu cug uuc         5053
Tyr Asn His Arg His Ser Val Gly Ala Thr Leu Glu Ala Leu Phe
        1425                1430                1435 caa ggg cca cca guc uac aga gag auc aaa auc agc guc gcc cca         5098
Gln Gly Pro Pro Val Tyr Arg Glu Ile Lys Ile Ser Val Ala Pro
        1440                1445                1450 gag aca ccc cca cca cca gcu auu gcu gau uua cug aaa uca gug         5143
Glu Thr Pro Pro Pro Pro Ala Ile Ala Asp Leu Leu Lys Ser Val
        1455                1460                1465 gac agu gaa gcu gug agg gaa uac ugc aag gag aga ggg ugg cuu         5188
Asp Ser Glu Ala Val Arg Glu Tyr Cys Lys Glu Arg Gly Trp Leu
        1470                1475                1480 gug cca gag auc aau ucu acc cua caa aua gag aag cau gug agu         5233
Val Pro Glu Ile Asn Ser Thr Leu Gln Ile Glu Lys His Val Ser
        1485                1490                1495 aga gca uuc aua ugu uua caa gcc cua acc acg uuu guu uca guu         5278
Arg Ala Phe Ile Cys Leu Gln Ala Leu Thr Thr Phe Val Ser Val
        1500                1505                1510 gcu ggu aua aua uac auu auu uac aaa uua uuu gca ggu uuc caa         5323
Ala Gly Ile Ile Tyr Ile Ile Tyr Lys Leu Phe Ala Gly Phe Gln
        1515                1520                1525 ggc gcc uac aca ggg aug ccc aac cag aaa ccu aag gug ccc acc         5368
Gly Ala Tyr Thr Gly Met Pro Asn Gln Lys Pro Lys Val Pro Thr
        1530                1535                1540 cug aga cag gcc aaa gua cag ggc cca gcg uuu gag uuc gcu gug         5413
Leu Arg Gln Ala Lys Val Gln Gly Pro Ala Phe Glu Phe Ala Val
        1545                1550                1555 gcg aug aug aaa agg aac gcc agu aca gua aaa acc gag uac ggu         5458
Ala Met Met Lys Arg Asn Ala Ser Thr Val Lys Thr Glu Tyr Gly
        1560                1565                1570 gaa uuc acc aug cuu ggc auu uac gac aag ugg gcg gug uua ccg         5503
Glu Phe Thr Met Leu Gly Ile Tyr Asp Lys Trp Ala Val Leu Pro
        1575                1580                1585 cgc cac gcc aag ccu ggc ccc acc auc uug aug aau gau cag gaa         5548
Arg His Ala Lys Pro Gly Pro Thr Ile Leu Met Asn Asp Gln Glu
        1590                1595                1600 guc ggc gug uug gau gcc aag gaa cua guu gau aaa gau ggg aca         5593
Val Gly Val Leu Asp Ala Lys Glu Leu Val Asp Lys Asp Gly Thr
        1605                1610                1615 aau cua gaa uug acu cuc cug aag cuc aac cgu aac gaa aag uuc         5638
Asn Leu Glu Leu Thr Leu Leu Lys Leu Asn Arg Asn Glu Lys Phe
        1620                1625                1630 aga gau auu agg ggg uuu cua gca aga gaa gag guu gaa gug aau         5683
Arg Asp Ile Arg Gly Phe Leu Ala Arg Glu Glu Val Glu Val Asn
        1635                1640                1645 gaa gcu guc cua gca aua aau aca agc aaa uuc ccu aac aug uac         5728
Glu Ala Val Leu Ala Ile Asn Thr Ser Lys Phe Pro Asn Met Tyr
```

```
                    1650                    1655                    1660 aua cca gug ggc cag gug acu gac uac ggg uuu cug aac cug gga         5773
Ile Pro Val Gly Gln Val Thr Asp Tyr Gly Phe Leu Asn Leu Gly
            1665                    1670                    1675 ggg acu ccc acg aag aga aug cuc aug uau aac uuc cca acu aga         5818
Gly Thr Pro Thr Lys Arg Met Leu Met Tyr Asn Phe Pro Thr Arg
        1680                    1685                    1690 gca ggu cag ugu gga ggu guc cuc aug uca aca ggg aaa guc cug         5863
Ala Gly Gln Cys Gly Gly Val Leu Met Ser Thr Gly Lys Val Leu
    1695                    1700                    1705 gga aua cau gua gga ggg aau gga cau caa ggg uuc uca gcg gca         5908
Gly Ile His Val Gly Gly Asn Gly His Gln Gly Phe Ser Ala Ala
1710                    1715                    1720 cuc cuc agg cac uac uuc aac gag gag cag ggu gaa aua gaa uuc         5953
Leu Leu Arg His Tyr Phe Asn Glu Glu Gln Gly Glu Ile Glu Phe
        1725                    1730                    1735 auu gag agc uca aag gac gcg gga uuc ccu gug auc aac acu ccc         5998
Ile Glu Ser Ser Lys Asp Ala Gly Phe Pro Val Ile Asn Thr Pro
    1740                    1745                    1750 agu aag aca aaa uug gaa cca agu gug uuu cac cag gug uuc gag         6043
Ser Lys Thr Lys Leu Glu Pro Ser Val Phe His Gln Val Phe Glu
1755                    1760                    1765 ggc aac aag gaa cca gcg guc cuu aga aau ggg gac cca cga cuc         6088
Gly Asn Lys Glu Pro Ala Val Leu Arg Asn Gly Asp Pro Arg Leu
        1770                    1775                    1780 aaa gcc aac uuc gag gaa gca auc uuc ucc aag uac auu ggc aau         6133
Lys Ala Asn Phe Glu Glu Ala Ile Phe Ser Lys Tyr Ile Gly Asn
    1785                    1790                    1795 guc aac acg cau gua gau gag uac aug uug gag gcu gug gac cau         6178
Val Asn Thr His Val Asp Glu Tyr Met Leu Glu Ala Val Asp His
1800                    1805                    1810 uau gca gga caa cua gcu acu cug gac auc agu acg gag ccc aug         6223
Tyr Ala Gly Gln Leu Ala Thr Leu Asp Ile Ser Thr Glu Pro Met
        1815                    1820                    1825 aag cua gag gac gcc gug uau ggu aca gag ggg cug gaa gca cua         6268
Lys Leu Glu Asp Ala Val Tyr Gly Thr Glu Gly Leu Glu Ala Leu
    1830                    1835                    1840 gac cua acc acc agu gca ggc uac ccu uac gug gcc cug ggc auc         6313
Asp Leu Thr Thr Ser Ala Gly Tyr Pro Tyr Val Ala Leu Gly Ile
1845                    1850                    1855 aag aaa aga gau auu cua ucu aag aag acu aaa gac cuc acu aag         6358
Lys Lys Arg Asp Ile Leu Ser Lys Lys Thr Lys Asp Leu Thr Lys
        1860                    1865                    1870 uug aag gaa ugc aug gac aaa uau ggc cua aau uug cca aug gua         6403
Leu Lys Glu Cys Met Asp Lys Tyr Gly Leu Asn Leu Pro Met Val
    1875                    1880                    1885 acc uac guc aaa gau gag uug aga ucu gcu gag aag gug gcc aag         6448
Thr Tyr Val Lys Asp Glu Leu Arg Ser Ala Glu Lys Val Ala Lys
1890                    1895                    1900 gga aaa ucc agg cuu auu gag gcu ucu agu cuc aau gac uca gua         6493
Gly Lys Ser Arg Leu Ile Glu Ala Ser Ser Leu Asn Asp Ser Val
        1905                    1910                    1915 gca aug agg caa aca uuu gga aau uua uau aag acc uuu cac cuc         6538
Ala Met Arg Gln Thr Phe Gly Asn Leu Tyr Lys Thr Phe His Leu
    1920                    1925                    1930 aac ccg ggc auc guu acg ggc agu gcu guu ggg ugu gau cca gau         6583
Asn Pro Gly Ile Val Thr Gly Ser Ala Val Gly Cys Asp Pro Asp
1935                    1940                    1945 gug uuu ugg agc aag auc ccu guu aug cuu gau gga cau cuc aua         6628
```

```
Val Phe Trp Ser Lys Ile Pro Val Met Leu Asp Gly His Leu Ile
        1950            1955            1960 gcu uuu gac uau uca ggc uau gac gcu agc cuc agc cca gug ugg      6673
Ala Phe Asp Tyr Ser Gly Tyr Asp Ala Ser Leu Ser Pro Val Trp
1965            1970            1975 uuu gca ugu uug aaa cuu cuc cua gag aaa cua ggg uau aca aac      6718
Phe Ala Cys Leu Lys Leu Leu Leu Glu Lys Leu Gly Tyr Thr Asn
    1980            1985            1990 aag gaa aca aac uac aua gau uac cuc ugu aau ucc cau cac cug      6763
Lys Glu Thr Asn Tyr Ile Asp Tyr Leu Cys Asn Ser His His Leu
        1995            2000            2005 uau aga gac aag cac uac uuu gua aga ggc ggu aug cca uca ggg      6808
Tyr Arg Asp Lys His Tyr Phe Val Arg Gly Gly Met Pro Ser Gly
2010            2015            2020 ugu uca ggc acc agc aua uuu aau ucc aug auu aac aac auc aua      6853
Cys Ser Gly Thr Ser Ile Phe Asn Ser Met Ile Asn Asn Ile Ile
    2025            2030            2035 auc agg acu cuc aug cug aag guu uau aaa ggc auu gau uug gac      6898
Ile Arg Thr Leu Met Leu Lys Val Tyr Lys Gly Ile Asp Leu Asp
        2040            2045            2050 caa uuc aga aug auu gcc uau ggg gau gau gug auu gcu ucc uau      6943
Gln Phe Arg Met Ile Ala Tyr Gly Asp Asp Val Ile Ala Ser Tyr
2055            2060            2065 ccg ugg ccu auc gau gcu ucg cug uua gcu gaa gca gga aaa gau      6988
Pro Trp Pro Ile Asp Ala Ser Leu Leu Ala Glu Ala Gly Lys Asp
    2070            2075            2080 uau ggu uua auc aug acc cca gca gac aaa ggc gag ugc uuc aac      7033
Tyr Gly Leu Ile Met Thr Pro Ala Asp Lys Gly Glu Cys Phe Asn
        2085            2090            2095 gag gua acc ugg acg aau gug acc uuu cug aaa agg uac uuu agg      7078
Glu Val Thr Trp Thr Asn Val Thr Phe Leu Lys Arg Tyr Phe Arg
2100            2105            2110 gca gau gag caa uac cca uuu cug guc cau ccu guu aug cca aug      7123
Ala Asp Glu Gln Tyr Pro Phe Leu Val His Pro Val Met Pro Met
    2115            2120            2125 aag gac aua cau gag ucc auu agg ugg acc aaa gau ccc aag aac      7168
Lys Asp Ile His Glu Ser Ile Arg Trp Thr Lys Asp Pro Lys Asn
        2130            2135            2140 aca cag gau cau gug cgc ucg cug ugc cua uug gcu ugg cac aac      7213
Thr Gln Asp His Val Arg Ser Leu Cys Leu Leu Ala Trp His Asn
2145            2150            2155 ggg gag caa gaa uau gag gag uuu auu cgc aag auc aga agc gug      7258
Gly Glu Gln Glu Tyr Glu Glu Phe Ile Arg Lys Ile Arg Ser Val
    2160            2165            2170 ccc guu ggg cgc ugc uug acc cua ccc gcu uuu uca aca cug cgc      7303
Pro Val Gly Arg Cys Leu Thr Leu Pro Ala Phe Ser Thr Leu Arg
        2175            2180            2185 agg aag ugg cug gac ucc uuu uaa aauuagagca uaauuaguaa aucauaauug  7357
Arg Lys Trp Leu Asp Ser Phe
2190 gcuuaacccu accgcaugaa ccgaacuuga uaaaagugcg guaggggtaa auucuccgca  7417 uucggugcgg                                                         7427

<210> SEQ ID NO 4
<211> LENGTH: 2194
<212> TYPE: PRT
<213> ORGANISM: Enterovirus sp. Echo 7
<220> FEATURE:
<221> NAME/KEY: MISC_FEATURE
<222> LOCATION: (16)..(16)
```

-continued

<223> OTHER INFORMATION: unknown
      Amino acid sequence of the modified virus
<220> FEATURE:
<221> NAME/KEY: MISC_FEATURE
<222> LOCATION: (404)..(404)
<223> OTHER INFORMATION: unknown
<220> FEATURE:
<221> NAME/KEY: MISC_FEATURE
<222> LOCATION: (954)..(954)
<223> OTHER INFORMATION: unknown
<220> FEATURE:
<221> NAME/KEY: MISC_FEATURE
<222> LOCATION: (1065)..(1065)
<223> OTHER INFORMATION: unknown

<400> SEQUENCE: 4

Met Gly Ala Gln Val Ser Thr Gln Lys Thr Gly Ala His Glu Thr Xaa
1               5                   10                  15

Leu Ser Ala Asn Gly His Ser Ile Ile His Tyr Thr Asn Ile Asn Tyr
            20                  25                  30

Tyr Lys Asp Ala Ala Ser Asn Ser Ala Asn Arg Gln Asp Phe Thr Gln
        35                  40                  45

Asp Pro Gly Lys Phe Thr Glu Pro Val Lys Asp Ile Met Ile Lys Ser
    50                  55                  60

Met Pro Ala Leu Asn Ser Pro Ser Ala Glu Glu Cys Gly Tyr Ser Asp
65                  70                  75                  80

Arg Val Arg Ser Leu Thr Leu Gly Asn Ser Thr Ile Thr Thr Gln Glu
                85                  90                  95

Ser Ala Asn Val Val Val Gly Tyr Gly Arg Trp Pro Glu Tyr Leu Lys
            100                 105                 110

Asp Glu Glu Ala Thr Ala Glu Asp Gln Pro Thr Gln Pro Asp Val Ala
        115                 120                 125

Thr Cys Arg Phe Tyr Thr Leu Glu Ser Val Gln Trp Glu Lys Asn Ser
    130                 135                 140

Ala Gly Trp Trp Trp Lys Phe Pro Glu Ala Leu Lys Asp Met Gly Leu
145                 150                 155                 160

Phe Gly Gln Asn Met Leu Tyr His Tyr Leu Gly Arg Ala Gly Tyr Thr
                165                 170                 175

Ile His Val Gln Cys Asn Ala Ser Lys Phe His Gln Gly Cys Leu Leu
            180                 185                 190

Val Val Cys Val Pro Glu Ala Glu Met Gly Cys Ser Gln Thr Asp Lys
        195                 200                 205

Glu Val Ala Ala Met Asn Leu Thr Lys Gly Glu Thr Ala His Lys Phe
    210                 215                 220

Glu Pro Thr Lys Thr Thr Gly Gly His Thr Val Gln Ser Ile Val Cys
225                 230                 235                 240

Asn Ala Gly Met Gly Ile Gly Val Gly Asn Leu Thr Ile Tyr Pro His
                245                 250                 255

Gln Trp Ile Asn Leu Arg Thr Asn Asn Cys Ala Thr Ile Val Met Pro
            260                 265                 270

Tyr Ile Asn Ser Val Pro Met Asp Asn Met Phe Arg His Tyr Asn Phe
        275                 280                 285

Thr Leu Met Val Ile Pro Phe Ala Pro Leu Asp Tyr Asn Ala Gln Ala
    290                 295                 300

Ser Glu Tyr Val Pro Val Thr Val Thr Ile Ala Pro Met Cys Ala Glu
305                 310                 315                 320

Tyr Asn Gly Leu Arg Leu Ala Tyr Gln Gln Gly Leu Pro Val Leu Asn
                325                 330                 335

-continued

```
Thr Pro Gly Ser Asn Gln Phe Met Thr Ser Asp Asp Phe Gln Ser Pro
            340                 345                 350

Ser Ala Met Pro Gln Phe Asp Val Thr Pro His Met Asp Ile Pro Gly
        355                 360                 365

Glu Val His Asn Leu Met Glu Ile Ala Glu Val Asp Ser Val Val Pro
370                 375                 380

Val Asn Thr Ala Ala Asn Leu Gln Ser Met Asp Ala Tyr His Ile
385                 390                 395                 400

Glu Val Asn Xaa Gly Asn His Gln Gly Glu Lys Ile Phe Ala Phe Gln
                405                 410                 415

Ile Gln Pro Gly Leu Asp Ser Val Phe Lys Arg Thr Leu Leu Gly Glu
            420                 425                 430

Val Leu Asn Tyr Tyr Ala His Trp Ser Gly Ser Ile Lys Leu Thr Phe
        435                 440                 445

Thr Phe Cys Gly Ser Ala Met Ala Thr Gly Lys Leu Leu Leu Ala Tyr
    450                 455                 460

Ser Pro Pro Gly Ala Asp Val Pro Ala Ser Arg Lys Gln Ala Met Met
465                 470                 475                 480

Gly Thr His Ile Ile Trp Asp Leu Gly Leu Gln Ser Ser Cys Val Leu
                485                 490                 495

Cys Ile Pro Trp Ile Ser Gln Thr His Tyr Arg Leu Val Gln Gln Asp
            500                 505                 510

Glu Tyr Thr Ser Ala Gly Asn Val Thr Cys Trp Tyr Gln Thr Gly Ile
        515                 520                 525

Val Val Pro Pro Gly Thr Pro Asn Lys Cys Val Val Leu Cys Phe Val
    530                 535                 540

Ser Ala Cys Asn Asp Phe Ser Val Arg Met Leu Arg Asp Thr Pro Phe
545                 550                 555                 560

Ile Gly Gln Thr Thr Leu Leu Gln Gly Asp Thr Asp Val Ala Val Asn
                565                 570                 575

Asn Ala Val Ala Arg Val Ala Asp Thr Ile Ala Ser Gly Pro Ser Asn
            580                 585                 590

Ser Thr Ser Ile Pro Ala Leu Thr Ala Val Glu Thr Gly His Thr Ser
        595                 600                 605

Gln Val Glu Pro Ser Asp Thr Met Gln Thr Arg His Val Lys Asn Tyr
    610                 615                 620

His Ser Arg Ser Glu Ser Thr Ile Glu Asn Phe Leu Ser Arg Ser Ala
625                 630                 635                 640

Cys Val Tyr Ile Glu Glu Tyr Phe Thr Lys Asp Gln Asp Ser Ala Asn
                645                 650                 655

Arg Tyr Met Ser Trp Thr Ile Asn Ala Arg Arg Met Val Gln Leu Arg
            660                 665                 670

Arg Lys Phe Glu Leu Phe Thr Tyr Met Arg Phe Asp Met Glu Ile Thr
        675                 680                 685

Phe Val Ile Thr Ser Arg Gln Leu Pro Gly Thr Ser Ile Ala Gln Asp
    690                 695                 700

Met Pro Pro Leu Thr His Gln Ile Met Tyr Ile Pro Pro Gly Gly Pro
705                 710                 715                 720

Val Pro Asn Ser Val Thr Asp Phe Ala Trp Gln Thr Ser Thr Asn Pro
                725                 730                 735

Ser Ile Phe Trp Thr Glu Gly Asn Ala Pro Pro Arg Met Ser Ile Pro
            740                 745                 750
```

-continued

Phe Ile Ser Ile Gly Asn Ala Tyr Ser Asn Phe Tyr Asp Gly Trp Ser
            755                 760                 765

His Phe Ser Gln Asn Gly Val Tyr Gly Tyr Asn Ala Leu Asn Asn Met
        770                 775                 780

Gly Lys Leu Tyr Ala Arg His Val Asn Lys Asp Thr Pro Tyr Gln Met
785                 790                 795                 800

Ser Ser Thr Ile Arg Val Tyr Phe Lys Pro Lys His Ile Arg Val Trp
                805                 810                 815

Val Pro Arg Pro Arg Leu Cys Pro Tyr Ile Lys Ser Asn Val
            820                 825                 830

Asn Phe Asp Pro Thr Asn Leu Thr Asp Ser Arg Ser Ser Ile Thr Tyr
            835                 840                 845

Val Pro Asp Thr Ile Arg Pro Glu Val Arg Thr Ala Gly Lys Phe Gly
    850                 855                 860

His Gln Ser Gly Ala Val Tyr Val Gly Asn Tyr Arg Ile Val Asn Arg
865                 870                 875                 880

His Leu Ala Thr His Asn Asp Trp Gln Asn Cys Val Trp Glu Asp Tyr
                885                 890                 895

Asn Arg Asp Leu Leu Val Ser Thr Thr Thr Ala His Gly Cys Asp Thr
            900                 905                 910

Ile Ala Arg Cys Gln Cys Thr Ala Gly Val Tyr Phe Cys Ala Ser Arg
        915                 920                 925

Asn Lys His Tyr Pro Val Thr Phe Glu Gly Pro Gly Leu Val Glu Val
        930                 935                 940

Gln Glu Ser Glu Tyr Tyr Pro Lys Arg Xaa Gln Ser His Val Leu Leu
945                 950                 955                 960

Ala Ala Gly Phe Ser Glu Pro Gly Asp Cys Gly Gly Ile Leu Arg Cys
                965                 970                 975

Gln His Gly Val Ile Gly Ile Val Thr Met Gly Gly Glu Gly Val Val
            980                 985                 990

Gly Phe Ala Asp Val Arg Asp Leu Leu Trp Leu Glu Asp Asp Ala Met
        995                 1000                1005

Glu Gln Gly Val Arg Asp Tyr Val Glu Gln Leu Gly Asn Ala Phe
    1010                1015                1020

Gly Ser Gly Phe Thr Asn Gln Ile Cys Glu Gln Val Asn Leu Leu
    1025                1030                1035

Lys Glu Ser Leu Val Gly Gln Asp Ser Ile Leu Glu Lys Ser Leu
    1040                1045                1050

Lys Ala Leu Val Lys Ile Ile Ser Ala Leu Val Xaa Val Val Arg
    1055                1060                1065

Asn His Asp Asp Leu Ile Thr Val Thr Ala Thr Leu Ala Leu Ile
    1070                1075                1080

Gly Cys Thr Ser Ser Pro Trp Arg Trp Leu Lys Gln Lys Val Ser
    1085                1090                1095

Gln Tyr Tyr Gly Ile Pro Arg Ala Glu Arg Gln Asn Asn Ser Trp
    1100                1105                1110

Leu Lys Lys Phe Thr Glu Met Thr Asn Ala Cys Lys Gly Met Glu
    1115                1120                1125

Trp Ile Ala Ile Lys Ile Gln Lys Phe Ile Glu Trp Leu Lys Val
    1130                1135                1140

Lys Ile Leu Pro Glu Val Lys Glu Lys His Glu Phe Leu Asn Arg
    1145                1150                1155

Leu Lys Gln Leu Pro Leu Leu Glu Ser Gln Ile Ala Thr Ile Glu

```
            1160                1165                1170
Gln Ser Ala Pro Ser Gln Ser Asp Gln Glu Gln Leu Phe Ser Asn
    1175                1180                1185
Val Gln Tyr Phe Ala His Tyr Cys Arg Lys Tyr Ala Pro Leu Tyr
    1190                1195                1200
Ala Ala Glu Ala Lys Arg Val Phe Ser Leu Glu Lys Lys Met Ser
    1205                1210                1215
Asn Tyr Ile Gln Phe Lys Ser Lys Cys Arg Ile Glu Pro Val Cys
    1220                1225                1230
Leu Leu Leu His Gly Ser Pro Gly Ala Gly Lys Ser Val Ala Thr
    1235                1240                1245
Asn Leu Ile Gly Arg Ser Leu Ala Glu Lys Leu Asn Ser Ser Val
    1250                1255                1260
Tyr Ser Leu Pro Pro Asp Pro Asp His Phe Asp Gly Tyr Lys Gln
    1265                1270                1275
Gln Ala Val Val Ile Met Asp Asp Leu Cys Gln Asn Pro Asp Gly
    1280                1285                1290
Lys Asp Val Ser Leu Phe Cys Gln Met Val Ser Ser Val Asp Phe
    1295                1300                1305
Val Pro Pro Met Ala Ala Leu Glu Glu Lys Gly Ile Leu Phe Thr
    1310                1315                1320
Ser Pro Phe Val Leu Ala Ser Thr Asn Ala Gly Ser Ile Asn Ala
    1325                1330                1335
Pro Thr Val Ser Asp Ser Arg Ala Leu Ala Arg Arg Phe His Phe
    1340                1345                1350
Asp Met Asn Ile Glu Val Ile Ser Met Tyr Ser Gln Asn Gly Lys
    1355                1360                1365
Ile Asn Met Pro Met Ser Val Lys Thr Cys Asp Glu Glu Cys Cys
    1370                1375                1380
Pro Val Asn Phe Lys Arg Cys Cys Pro Leu Val Cys Gly Lys Ala
    1385                1390                1395
Met Gln Phe Ile Asp Arg Arg Thr Gln Val Arg Tyr Ser Leu Asp
    1400                1405                1410
Met Leu Val Thr Glu Met Phe Arg Glu Tyr Asn His Arg His Ser
    1415                1420                1425
Val Gly Ala Thr Leu Glu Ala Leu Phe Gln Gly Pro Pro Val Tyr
    1430                1435                1440
Arg Glu Ile Lys Ile Ser Val Ala Pro Glu Thr Pro Pro Pro Pro
    1445                1450                1455
Ala Ile Ala Asp Leu Leu Lys Ser Val Asp Ser Glu Ala Val Arg
    1460                1465                1470
Glu Tyr Cys Lys Glu Arg Gly Trp Leu Val Pro Glu Ile Asn Ser
    1475                1480                1485
Thr Leu Gln Ile Glu Lys His Val Ser Arg Ala Phe Ile Cys Leu
    1490                1495                1500
Gln Ala Leu Thr Thr Phe Val Ser Val Ala Gly Ile Ile Tyr Ile
    1505                1510                1515
Ile Tyr Lys Leu Phe Ala Gly Phe Gln Gly Ala Tyr Thr Gly Met
    1520                1525                1530
Pro Asn Gln Lys Pro Lys Val Pro Thr Leu Arg Gln Ala Lys Val
    1535                1540                1545
Gln Gly Pro Ala Phe Glu Phe Ala Val Ala Met Met Lys Arg Asn
    1550                1555                1560
```

```
Ala Ser Thr Val Lys Thr Glu Tyr Gly Glu Phe Thr Met Leu Gly
1565                 1570                 1575

Ile Tyr Asp Lys Trp Ala Val Leu Pro Arg His Ala Lys Pro Gly
1580                 1585                 1590

Pro Thr Ile Leu Met Asn Asp Gln Glu Val Gly Val Leu Asp Ala
1595                 1600                 1605

Lys Glu Leu Val Asp Lys Asp Gly Thr Asn Leu Glu Leu Thr Leu
1610                 1615                 1620

Leu Lys Leu Asn Arg Asn Glu Lys Phe Arg Asp Ile Arg Gly Phe
1625                 1630                 1635

Leu Ala Arg Glu Glu Val Glu Val Asn Glu Ala Val Leu Ala Ile
1640                 1645                 1650

Asn Thr Ser Lys Phe Pro Asn Met Tyr Ile Pro Val Gly Gln Val
1655                 1660                 1665

Thr Asp Tyr Gly Phe Leu Asn Leu Gly Gly Thr Pro Thr Lys Arg
1670                 1675                 1680

Met Leu Met Tyr Asn Phe Pro Thr Arg Ala Gly Gln Cys Gly Gly
1685                 1690                 1695

Val Leu Met Ser Thr Gly Lys Val Leu Gly Ile His Val Gly Gly
1700                 1705                 1710

Asn Gly His Gln Gly Phe Ser Ala Ala Leu Leu Arg His Tyr Phe
1715                 1720                 1725

Asn Glu Glu Gln Gly Glu Ile Glu Phe Ile Glu Ser Ser Lys Asp
1730                 1735                 1740

Ala Gly Phe Pro Val Ile Asn Thr Pro Ser Lys Thr Lys Leu Glu
1745                 1750                 1755

Pro Ser Val Phe His Gln Val Phe Glu Gly Asn Lys Glu Pro Ala
1760                 1765                 1770

Val Leu Arg Asn Gly Asp Pro Arg Leu Lys Ala Asn Phe Glu Glu
1775                 1780                 1785

Ala Ile Phe Ser Lys Tyr Ile Gly Asn Val Asn Thr His Val Asp
1790                 1795                 1800

Glu Tyr Met Leu Glu Ala Val Asp His Tyr Ala Gly Gln Leu Ala
1805                 1810                 1815

Thr Leu Asp Ile Ser Thr Glu Pro Met Lys Leu Glu Asp Ala Val
1820                 1825                 1830

Tyr Gly Thr Glu Gly Leu Glu Ala Leu Asp Leu Thr Thr Ser Ala
1835                 1840                 1845

Gly Tyr Pro Tyr Val Ala Leu Gly Ile Lys Lys Arg Asp Ile Leu
1850                 1855                 1860

Ser Lys Lys Thr Lys Asp Leu Thr Lys Leu Lys Glu Cys Met Asp
1865                 1870                 1875

Lys Tyr Gly Leu Asn Leu Pro Met Val Thr Tyr Val Lys Asp Glu
1880                 1885                 1890

Leu Arg Ser Ala Glu Lys Val Ala Lys Gly Lys Ser Arg Leu Ile
1895                 1900                 1905

Glu Ala Ser Ser Leu Asn Asp Ser Val Ala Met Arg Gln Thr Phe
1910                 1915                 1920

Gly Asn Leu Tyr Lys Thr Phe His Leu Asn Pro Gly Ile Val Thr
1925                 1930                 1935

Gly Ser Ala Val Gly Cys Asp Pro Asp Val Phe Trp Ser Lys Ile
1940                 1945                 1950
```

```
Pro Val Met Leu Asp Gly His Leu Ile Ala Phe Asp Tyr Ser Gly
1955                1960                1965

Tyr Asp Ala Ser Leu Ser Pro Val Trp Phe Ala Cys Leu Lys Leu
1970                1975                1980

Leu Leu Glu Lys Leu Gly Tyr Thr Asn Lys Glu Thr Asn Tyr Ile
1985                1990                1995

Asp Tyr Leu Cys Asn Ser His His Leu Tyr Arg Asp Lys His Tyr
2000                2005                2010

Phe Val Arg Gly Gly Met Pro Ser Gly Cys Ser Gly Thr Ser Ile
2015                2020                2025

Phe Asn Ser Met Ile Asn Asn Ile Ile Ile Arg Thr Leu Met Leu
2030                2035                2040

Lys Val Tyr Lys Gly Ile Asp Leu Asp Gln Phe Arg Met Ile Ala
2045                2050                2055

Tyr Gly Asp Asp Val Ile Ala Ser Tyr Pro Trp Pro Ile Asp Ala
2060                2065                2070

Ser Leu Leu Ala Glu Ala Gly Lys Asp Tyr Gly Leu Ile Met Thr
2075                2080                2085

Pro Ala Asp Lys Gly Glu Cys Phe Asn Glu Val Thr Trp Thr Asn
2090                2095                2100

Val Thr Phe Leu Lys Arg Tyr Phe Arg Ala Asp Glu Gln Tyr Pro
2105                2110                2115

Phe Leu Val His Pro Val Met Pro Met Lys Asp Ile His Glu Ser
2120                2125                2130

Ile Arg Trp Thr Lys Asp Pro Lys Asn Thr Gln Asp His Val Arg
2135                2140                2145

Ser Leu Cys Leu Leu Ala Trp His Asn Gly Glu Gln Glu Tyr Glu
2150                2155                2160

Glu Phe Ile Arg Lys Ile Arg Ser Val Pro Val Gly Arg Cys Leu
2165                2170                2175

Thr Leu Pro Ala Phe Ser Thr Leu Arg Arg Lys Trp Leu Asp Ser
2180                2185                2190

Phe

<210> SEQ ID NO 5
<211> LENGTH: 2196
<212> TYPE: PRT
<213> ORGANISM: Enterovirus sp. Echo 7
<220> FEATURE:
<221> NAME/KEY: MISC_FEATURE
<222> LOCATION: (16)..(16)
<223> OTHER INFORMATION: unknown
      Amino acid sequence of the unmodified virus
<220> FEATURE:
<221> NAME/KEY: MISC_FEATURE
<222> LOCATION: (404)..(404)
<223> OTHER INFORMATION: unknown
<220> FEATURE:
<221> NAME/KEY: MISC_FEATURE
<222> LOCATION: (1236)..(1236)
<223> OTHER INFORMATION: unknown

<400> SEQUENCE: 5

Met Gly Ala Gln Val Ser Thr Gln Lys Thr Gly Ala His Glu Thr Xaa
1               5                   10                  15

Leu Ser Ala Asn Gly Ser Ser Ile Ile His Tyr Thr Asn Ile Asn Tyr
            20                  25                  30

Tyr Lys Asp Ala Ala Ser Asn Ser Ala Asn Arg Gln Asp Phe Thr Gln
        35                  40                  45
```

```
Asp Pro Gly Lys Phe Thr Glu Pro Val Lys Asp Ile Met Ile Lys Ser
 50                  55                  60

Met Pro Ala Leu Asn Ser Pro Thr Val Glu Glu Cys Gly Tyr Ser Asp
 65                  70                  75                  80

Arg Val Arg Ser Ile Thr Leu Gly Asn Ser Thr Ile Thr Thr Gln Glu
                 85                  90                  95

Ser Ala Asn Val Val Val Gly Tyr Gly Gly Trp Pro Glu Tyr Leu Lys
                100                 105                 110

Asp Glu Glu Ala Thr Ala Glu Asp Gln Pro Thr Gln Pro Asp Val Ala
            115                 120                 125

Thr Cys Arg Phe Tyr Thr Leu Glu Ser Val Gln Trp Glu Lys Asn Ser
130                 135                 140

Ala Gly Trp Trp Trp Lys Phe Pro Glu Ala Leu Lys Asp Met Gly Leu
145                 150                 155                 160

Phe Gly Gln Asn Met His Tyr His Tyr Leu Gly Arg Ala Gly Tyr Thr
                165                 170                 175

Ile His Val Gln Cys Asn Ala Ser Lys Phe His Gln Gly Cys Leu Leu
                180                 185                 190

Val Val Cys Val Pro Glu Ala Glu Met Gly Cys Ser Lys Val Asp Gly
            195                 200                 205

Thr Val Asn Glu Gln Glu Leu Thr Glu Gly Thr Asp Met Lys Leu
210                 215                 220

Glu Pro Thr Arg Thr Thr Gly Val Arg Arg Val Gln Ser Ala Val Tyr
225                 230                 235                 240

Asn Ala Gly Met Gly Val Gly Val Gly Asn Leu Thr Ile Phe Pro His
                245                 250                 255

Gln Trp Ile Asn Leu Arg Thr Asn Asn Cys Ala Thr Ile Val Met Pro
                260                 265                 270

Tyr Ile Asn Ser Val Pro Met Asp Asn Met Phe Arg His Tyr Asn Phe
                275                 280                 285

Thr Leu Met Met Ile Pro Phe Ala Pro Leu Asp Tyr Thr Asn Gln Ala
            290                 295                 300

Ser Thr Tyr Val Pro Ile Thr Val Thr Ile Ala Pro Met Cys Ala Glu
305                 310                 315                 320

Tyr Asn Gly Leu Arg Leu Val Thr Ser Gln Gly Leu Pro Val Met Asn
                325                 330                 335

Thr Pro Gly Ser Asn Gln Phe Leu Thr Ser Asp Phe Gln Ser Pro
            340                 345                 350

Ser Ala Met Pro Gln Phe Asp Val Thr Pro Asp Met Asp Ile Pro Gly
            355                 360                 365

Glu Val Asn Asn Leu Met Glu Ile Ala Glu Val Asp Ser Val Val Pro
            370                 375                 380

Val Asn Asn Asn Glu Ala Asn Leu Lys Ser Met Asp Ala Tyr Arg Ile
385                 390                 395                 400

Pro Val Asn Xaa Gly Asn Gln Gln Gly Glu Lys Ile Phe Gly Phe Gln
                405                 410                 415

Ile Gln Pro Gly Leu Asp Ser Val Phe Lys Arg Thr Leu Leu Gly Glu
            420                 425                 430

Met Leu Asn Tyr Tyr Thr His Trp Ser Gly Ser Ile Lys Leu Thr Phe
            435                 440                 445

Met Phe Cys Gly Ser Ala Met Ala Thr Gly Lys Leu Leu Leu Ala Tyr
450                 455                 460
```

```
Ser Pro Gly Ala Asp Val Pro Thr Ser Arg Lys Glu Ala Met Leu
465                 470                 475                 480

Gly Thr His Val Ile Trp Asp Phe Gly Leu Gln Ser Ser Cys Val Leu
            485                 490                 495

Cys Val Pro Trp Ile Ser Gln Thr His Tyr Arg Leu Val Gln Gln Asp
            500                 505                 510

Glu Tyr Thr Gly Ala Gly Tyr Ile Thr Cys Trp Tyr Gln Thr Ser Ile
        515                 520                 525

Val Val Pro Pro Gly Thr Pro Lys Lys Cys Val Ile Leu Cys Phe Val
    530                 535                 540

Ser Ala Cys Asn Asp Phe Ser Val Ser Met Leu Ser Asp Thr Pro Phe
545                 550                 555                 560

Ile Gly Gln Thr Ala Leu Leu Gln Ser Pro Val Glu Glu Ala Glu Glu
                565                 570                 575

Asn Ala Val Ala Arg Val Ala Asp Thr Ile Ala Ser Gly Pro Ser Asn
            580                 585                 590

Ser Glu Ser Val Pro Ala Leu Thr Ala Val Glu Thr Gly His Thr Ser
        595                 600                 605

Gln Val Val Pro Ser Asp Thr Met Gln Thr Arg His Val Lys Asn Tyr
    610                 615                 620

His Ser Arg Ser Glu Ser Thr Ile Glu Asn Phe Leu Ser Arg Ser Ala
625                 630                 635                 640

Cys Val Tyr Ile Glu Glu Tyr Tyr Thr Asn Thr Glu Thr Arg Gln Asn
                645                 650                 655

Leu Tyr Met Leu Pro Thr Ile Asn Thr Arg Trp Met Val Gln Leu Arg
                660                 665                 670

Arg Lys Phe Glu Met Phe Thr Tyr Met Arg Phe Asp Met Glu Ile Thr
            675                 680                 685

Phe Val Ile Thr Ser Arg Gln Leu His Arg Thr Ser Met Pro Gln Asp
            690                 695                 700

Met Pro Val Leu Thr His Gln Ile Met Tyr Val Pro Pro Gly Gly Pro
705                 710                 715                 720

Val Pro Asn Ser Val Asp Asp Tyr Ala Trp Gln Thr Ser Thr Asn Pro
                725                 730                 735

Ser Val Phe Trp Thr Glu Gly Asn Ala Pro Pro Arg Met Ser Ile Pro
                740                 745                 750

Phe Ile Ser Ile Gly Asn Ala Tyr Ser Asn Phe Tyr Asp Gly Ser Ser
            755                 760                 765

His Phe Leu Gln Tyr Gly Val Tyr Gly Tyr Asn Thr Leu Asn Asn Met
    770                 775                 780

Gly Lys Leu Tyr Val Arg His Val Asn Asn His Thr Pro Tyr Gln Met
785                 790                 795                 800

Thr Ser Thr Val Ser Val Tyr Phe Lys Pro Lys His Val Arg Ala Trp
                805                 810                 815

Val Pro Arg Pro Pro Arg Leu Cys Pro Tyr Lys Asn Ala Trp Asn Val
    820                 825                 830

Asn Phe Glu Pro Thr Asn Val Thr Asp Ser Arg Ser Ser Ile Thr Tyr
        835                 840                 845

Ile Pro Glu Thr Val Lys Pro Asp Leu Ser Lys Ala Gly Ala Phe Gly
    850                 855                 860

His Gln Ser Gly Ala Val Tyr Val Gly Asn Tyr Arg Val Val Asn Arg
865                 870                 875                 880

His Leu Ala Thr His Asn Asp Trp Gln Asn Cys Val Trp Glu Asp Tyr
```

-continued

```
                885                 890                 895
Asn Arg Asp Leu Leu Val Ser Thr Thr Thr Ala His Gly Cys Asp Thr
                900                 905                 910
Ile Ala Arg Cys Gln Cys Thr Thr Gly Val Tyr Phe Cys Ala Ser Arg
                915                 920                 925
Asn Lys His Tyr Pro Val Thr Phe Glu Gly Pro Gly Leu Val Glu Val
                930                 935                 940
Gln Glu Ser Glu Tyr Tyr Pro Lys Arg Tyr Gln Ser His Val Leu Leu
945                 950                 955                 960
Ala Ala Gly Phe Ser Glu Pro Gly Asp Cys Gly Gly Ile Leu Arg Cys
                965                 970                 975
Glu His Gly Val Ile Gly Ile Val Thr Met Gly Gly Glu Gly Val Val
                980                 985                 990
Gly Phe Ala Asp Val Arg Asp Leu Leu Trp Leu Glu Asp Asp Ala Met
                995                1000                1005
Glu Gln Gly Val Arg Asp Tyr Val Glu Gln Leu Gly Asn Ala Phe
        1010                1015                1020
Gly Ser Gly Phe Thr Asn Gln Ile Cys Glu Gln Val Asn Leu Leu
        1025                1030                1035
Lys Glu Ser Leu Val Gly Gln Asp Ser Ile Leu Glu Lys Ser Leu
        1040                1045                1050
Lys Ala Leu Val Lys Ile Ile Ser Ala Leu Val Ile Val Val Arg
        1055                1060                1065
Asn His Asp Asp Leu Ile Thr Val Thr Ala Thr Leu Ala Leu Ile
        1070                1075                1080
Gly Cys Thr Ser Ser Pro Trp Arg Trp Leu Lys Gln Lys Val Ser
        1085                1090                1095
Gln Tyr Tyr Gly Ile Pro Met Ala Glu Arg Gln Asn Asn Gly Trp
        1100                1105                1110
Leu Lys Lys Phe Thr Glu Met Thr Asn Ala Cys Lys Gly Met Glu
        1115                1120                1125
Trp Ile Ala Ile Lys Ile Gln Lys Phe Ile Glu Trp Leu Lys Val
        1130                1135                1140
Lys Ile Tyr Gln Lys Cys Arg Lys Asn Met Ser Ser Ser Thr Asp
        1145                1150                1155
Tyr Asn Asn Tyr His Ser Trp Lys Ser Gln Ile Ala Thr Ile Glu
        1160                1165                1170
Gln Ser Ala Pro Ser Gln Ser Asp Gln Glu Gln Leu Phe Ser Asn
        1175                1180                1185
Val Gln Tyr Phe Ala His Tyr Cys Arg Lys Tyr Ala Pro Leu Tyr
        1190                1195                1200
Ala Ala Glu Ala Lys Arg Val Phe Ser Leu Glu Lys Lys Met Ser
        1205                1210                1215
Asn Tyr Ile Gln Phe Lys Ser Lys Cys Arg Ile Glu Pro Val Cys
        1220                1225                1230
Leu Leu Xaa His Gly Ser Pro Gly Ala Gly Lys Ser Val Ala Thr
        1235                1240                1245
Asn Leu Ile Gly Arg Ser Leu Ala Glu Lys Leu Asn Ser Ser Val
        1250                1255                1260
Tyr Ser Leu Pro Pro Asp Pro His Phe Asp Gly Tyr Lys Gln
        1265                1270                1275
Gln Ala Val Val Ile Met Asp Asp Leu Cys Gln Asn Pro Asp Gly
        1280                1285                1290
```

```
Lys Asp Val Ser Leu Phe Cys Gln Met Val Ser Ser Val Asp Phe
    1295                1300                1305

Val Pro Pro Met Ala Ala Leu Glu Glu Lys Gly Ile Leu Phe Thr
    1310                1315                1320

Ser Pro Phe Val Leu Ala Ser Thr Asn Ala Gly Ser Ile Asn Ala
    1325                1330                1335

Pro Thr Val Ser Asp Ser Arg Ala Leu Ala Arg Arg Phe His Phe
    1340                1345                1350

Asp Met Asn Ile Glu Val Ile Ser Met Tyr Ser Gln Asn Gly Lys
    1355                1360                1365

Ile Asn Met Pro Met Ser Val Lys Thr Cys Asp Glu Glu Cys Cys
    1370                1375                1380

Pro Val Asn Phe Lys Arg Cys Cys Pro Leu Val Cys Gly Lys Ala
    1385                1390                1395

Met Gln Phe Ile Asp Arg Arg Thr Gln Val Arg Tyr Ser Leu Asp
    1400                1405                1410

Met Leu Val Thr Glu Met Phe Arg Glu Tyr Asn His Arg His Ser
    1415                1420                1425

Val Gly Ala Thr Leu Glu Ala Leu Phe Gln Gly Pro Pro Val Tyr
    1430                1435                1440

Arg Glu Ile Lys Ile Ser Val Ala Pro Glu Thr Pro Pro Pro Pro
    1445                1450                1455

Ala Ile Ala Asp Leu Leu Lys Ser Val Asp Ser Glu Ala Val Arg
    1460                1465                1470

Glu Tyr Cys Lys Glu Lys Gly Trp Leu Val Pro Glu Ile Asn Ser
    1475                1480                1485

Thr Leu Gln Ile Glu Lys His Val Ser Arg Ala Phe Ile Cys Leu
    1490                1495                1500

Gln Ala Leu Thr Thr Phe Val Ser Val Ala Gly Ile Ile Tyr Ile
    1505                1510                1515

Ile Tyr Lys Leu Phe Ala Gly Phe Gln Gly Ala Tyr Thr Gly Met
    1520                1525                1530

Pro Asn Gln Lys Pro Lys Val Pro Thr Leu Arg Gln Ala Lys Val
    1535                1540                1545

Gln Gly Pro Ala Phe Glu Phe Ala Val Ala Met Met Lys Arg Asn
    1550                1555                1560

Ser Ser Thr Val Lys Thr Glu Tyr Gly Glu Phe Thr Met Leu Gly
    1565                1570                1575

Ile Tyr Asp Arg Trp Ala Val Leu Pro Arg His Ala Lys Pro Gly
    1580                1585                1590

Pro Thr Ile Leu Met Asn Asp Gln Glu Val Gly Val Leu Asp Ala
    1595                1600                1605

Lys Glu Leu Val Asp Lys Asp Gly Thr Asn Leu Glu Leu Thr Leu
    1610                1615                1620

Leu Lys Leu Asn Ser Asn Glu Lys Phe Arg Asp Ile Arg Gly Phe
    1625                1630                1635

Leu Ala Lys Glu Glu Val Glu Val Asn Glu Ala Val Leu Ala Ile
    1640                1645                1650

Asn Thr Ser Lys Phe Pro Asn Met Tyr Ile Pro Val Gly Gln Val
    1655                1660                1665

Thr Asp Tyr Gly Phe Leu Asn Leu Gly Gly Thr Pro Thr Lys Arg
    1670                1675                1680
```

```
Met Leu Met Tyr Asn Phe Pro Thr Arg Ala Gly Gln Cys Gly Gly
1685                1690                1695

Val Leu Met Ser Thr Gly Lys Val Leu Gly Ile His Val Gly Gly
1700                1705                1710

Asn Gly His Gln Gly Phe Ser Ala Ala Leu Leu Lys His Tyr Phe
1715                1720                1725

Asn Asp Glu Gln Gly Glu Ile Glu Phe Ile Glu Ser Ser Lys Asp
1730                1735                1740

Ala Gly Phe Pro Ile Ile Asn Thr Pro Ser Lys Thr Lys Leu Glu
1745                1750                1755

Pro Ser Val Phe His Gln Cys Leu Lys Ala Thr Lys Asn Pro Ala
1760                1765                1770

Val Leu Arg Asn Gly Asp Pro Arg Leu Lys Ala Asn Phe Glu Glu
1775                1780                1785

Ala Ile Phe Ser Lys Tyr Ile Gly Asn Val Asn Thr His Val Asp
1790                1795                1800

Glu Tyr Met Leu Glu Ala Val Asp His Tyr Ala Gly Gln Leu Ala
1805                1810                1815

Thr Leu Asp Ile Ser Thr Glu Pro Met Lys Leu Glu Asp Ala Val
1820                1825                1830

Tyr Gly Thr Glu Gly Leu Glu Ala Leu Asp Leu Thr Thr Ser Ala
1835                1840                1845

Gly Tyr Pro Tyr Val Ala Leu Gly Ile Lys Lys Arg Asp Ile Leu
1850                1855                1860

Ser Lys Lys Thr Arg Asp Leu Thr Lys Leu Lys Glu Cys Met Asp
1865                1870                1875

Lys Tyr Gly Leu Asn Leu Pro Met Val Thr Tyr Val Lys Asp Glu
1880                1885                1890

Leu Arg Ser Ala Glu Lys Val Ala Lys Gly Lys Ser Arg Leu Ile
1895                1900                1905

Glu Ala Ser Ser Leu Asn Asp Ser Val Ala Met Arg Gln Thr Phe
1910                1915                1920

Gly Asn Leu Tyr Lys Thr Phe His Leu Asn Pro Gly Ile Val Thr
1925                1930                1935

Gly Ser Ala Val Gly Cys Asp Pro Asp Leu Phe Trp Ser Lys Ile
1940                1945                1950

Pro Val Met Leu Asp Gly His Leu Ile Ala Phe Asp Tyr Ser Gly
1955                1960                1965

Tyr Asp Ala Ser Leu Ser Pro Val Trp Phe Ala Cys Leu Lys Leu
1970                1975                1980

Leu Leu Glu Lys Leu Gly Tyr Thr His Lys Glu Thr Asn Tyr Ile
1985                1990                1995

Asp Tyr Leu Cys Asn Ser His His Leu Tyr Arg Asp Lys His Tyr
2000                2005                2010

Phe Val Arg Gly Gly Met Pro Ser Gly Cys Ser Gly Thr Ser Ile
2015                2020                2025

Phe Asn Ser Met Ile Asn Asn Ile Ile Ile Arg Thr Leu Met Leu
2030                2035                2040

Lys Val Tyr Lys Gly Ile Asp Leu Asp Gln Phe Arg Ile Ile Ala
2045                2050                2055

Tyr Gly Asp Asp Val Ile Ala Ser Tyr Pro Trp Pro Ile Asp Ala
2060                2065                2070

Ser Leu Leu Ala Glu Ala Gly Lys Asp Tyr Gly Leu Ile Met Thr
```

```
                    2075                2080                2085
Pro Ala  Asp Lys Gly Glu  Cys Phe Asn Glu  Val Asn Trp Thr Asn
         2090                2095                2100

Val Thr  Phe Leu Lys Arg  Tyr Phe Arg Ala  Asp Glu Gln Tyr Pro
         2105                2110                2115

Phe Leu  Val His Pro Val  Met Pro Met Lys  Asp Ile His Glu Ser
         2120                2125                2130

Ile Arg  Trp Thr Lys Asp  Pro Lys Asn Thr  Gln Asp His Val Arg
         2135                2140                2145

Ser Leu  Cys Leu Leu Ala  Trp His Asn Gly  Glu His Glu Tyr Glu
         2150                2155                2160

Glu Phe  Ile Arg Lys Ile  Arg Lys Arg Ala  Ser Trp Thr Leu Phe
         2165                2170                2175

Asp Pro  Thr Cys Val Phe  Asn Pro Ala Gln  Glu Val Val Gly Leu
         2180                2185                2190

Leu Leu  Lys
         2195

<210> SEQ ID NO 6
<211> LENGTH: 20
<212> TYPE: DNA
<213> ORGANISM: Artificial sequence
<220> FEATURE:
<223> OTHER INFORMATION: Primer Eo7-1F

<400> SEQUENCE: 6
ttaaaacagc ctgtgggttg                                              20

<210> SEQ ID NO 7
<211> LENGTH: 22
<212> TYPE: DNA
<213> ORGANISM: Artificial sequence
<220> FEATURE:
<223> OTHER INFORMATION: Primer Eo7-1R

<400> SEQUENCE: 7
gaaacacgga cacccaaagt ag                                           22

<210> SEQ ID NO 8
<211> LENGTH: 20
<212> TYPE: DNA
<213> ORGANISM: Artificial sequence
<220> FEATURE:
<223> OTHER INFORMATION: Primer Eo7-2F

<400> SEQUENCE: 8
ccatgggacg cttcaatact                                              20

<210> SEQ ID NO 9
<211> LENGTH: 20
<212> TYPE: DNA
<213> ORGANISM: Artificial sequence
<220> FEATURE:
<223> OTHER INFORMATION: Primer Eo7-2R

<400> SEQUENCE: 9
gcaccagtct tttgtgtcga                                              20

<210> SEQ ID NO 10
<211> LENGTH: 25
<212> TYPE: DNA
<213> ORGANISM: Artificial sequence
```

```
<220> FEATURE:
<223> OTHER INFORMATION: Primer Eo7-3F

<400> SEQUENCE: 10
cgactacttt gggtgtccgt gtttc                                           25

<210> SEQ ID NO 11
<211> LENGTH: 23
<212> TYPE: DNA
<213> ORGANISM: Artificial sequence
<220> FEATURE:
<223> OTHER INFORMATION: Primer Eo7-3R

<400> SEQUENCE: 11
tcdggraayt tccaccacca ccc                                             23

<210> SEQ ID NO 12
<211> LENGTH: 20
<212> TYPE: DNA
<213> ORGANISM: Artificial sequence
<220> FEATURE:
<223> OTHER INFORMATION: Primer Eo7-4F

<400> SEQUENCE: 12
cgacagggtg agatccctaa                                                 20

<210> SEQ ID NO 13
<211> LENGTH: 20
<212> TYPE: DNA
<213> ORGANISM: Artificial sequence
<220> FEATURE:
<223> OTHER INFORMATION: Primer Eo7-4R

<400> SEQUENCE: 13 tttcacccett cgtgaggttc                                                20

<210> SEQ ID NO 14
<211> LENGTH: 20
<212> TYPE: DNA
<213> ORGANISM: Artificial sequence
<220> FEATURE:
<223> OTHER INFORMATION: Primer Eo7-5F

<400> SEQUENCE: 14
gcatcyaart tycaycargg                                                 20

<210> SEQ ID NO 15
<211> LENGTH: 20
<212> TYPE: DNA
<213> ORGANISM: Artificial sequence
<220> FEATURE:
<223> OTHER INFORMATION: Primer Eo7-5R

<400> SEQUENCE: 15
cacatkggkg caatsgtgac                                                 20

<210> SEQ ID NO 16
<211> LENGTH: 20
<212> TYPE: DNA
<213> ORGANISM: Artificial sequence
<220> FEATURE:
<223> OTHER INFORMATION: Primer Eo7-6F

<400> SEQUENCE: 16
gtggatcaac ttgcgcacta                                                 20
```

```
<210> SEQ ID NO 17
<211> LENGTH: 20
<212> TYPE: DNA
<213> ORGANISM: Artificial sequence
<220> FEATURE:
<223> OTHER INFORMATION: Primer Eo7-6R

<400> SEQUENCE: 17
aaattgtggc atagccgaag                                                    20

<210> SEQ ID NO 18
<211> LENGTH: 20
<212> TYPE: DNA
<213> ORGANISM: Artificial sequence
<220> FEATURE:
<223> OTHER INFORMATION: Primer Eo7-7F

<400> SEQUENCE: 18
gtcacsattg cmccmatgtg                                                    20

<210> SEQ ID NO 19
<211> LENGTH: 23
<212> TYPE: DNA
<213> ORGANISM: Artificial sequence
<220> FEATURE:
<223> OTHER INFORMATION: Primer Eo7-7R
<220> FEATURE:
<221> NAME/KEY: misc_feature
<222> LOCATION: (4)..(4)
<223> OTHER INFORMATION: n = any nucleotide

<400> SEQUENCE: 19
cttnatrcty cctgaccagt gtg                                                23

<210> SEQ ID NO 20
<211> LENGTH: 20
<212> TYPE: DNA
<213> ORGANISM: Artificial sequence
<220> FEATURE:
<223> OTHER INFORMATION: Primer Eo7-8F

<400> SEQUENCE: 20
aagcatggac gcatatcaca                                                    20

<210> SEQ ID NO 21
<211> LENGTH: 20
<212> TYPE: DNA
<213> ORGANISM: Artificial sequence
<220> FEATURE:
<223> OTHER INFORMATION: Primer Eo7-8R

<400> SEQUENCE: 21
gatatgggtt cccacattgc                                                    20

<210> SEQ ID NO 22
<211> LENGTH: 23
<212> TYPE: DNA
<213> ORGANISM: Artificial sequence
<220> FEATURE:
<223> OTHER INFORMATION: Primer Eo7-9F
<220> FEATURE:
<221> NAME/KEY: misc_feature
<222> LOCATION: (20)..(20)
<223> OTHER INFORMATION: n = any nucleotide

<400> SEQUENCE: 22
cacactggtc aggragyatn aag                                                23
```

<210> SEQ ID NO 23
<211> LENGTH: 20
<212> TYPE: DNA
<213> ORGANISM: Artificial sequence
<220> FEATURE:
<223> OTHER INFORMATION: Primer Eo7-10F

<400> SEQUENCE: 23
caagtgtgtc gtcctgtgct                                          20

<210> SEQ ID NO 24
<211> LENGTH: 20
<212> TYPE: DNA
<213> ORGANISM: Artificial sequence
<220> FEATURE:
<223> OTHER INFORMATION: Primer Eo7-9R

<400> SEQUENCE: 24
cctattggcg ctgtcttgat                                          20

<210> SEQ ID NO 25
<211> LENGTH: 20
<212> TYPE: DNA
<213> ORGANISM: Artificial sequence
<220> FEATURE:
<223> OTHER INFORMATION: Primer Eo7-11F

<400> SEQUENCE: 25
accaaagatc aagacagcgc                                          20

<210> SEQ ID NO 26
<211> LENGTH: 20
<212> TYPE: DNA
<213> ORGANISM: Artificial sequence
<220> FEATURE:
<223> OTHER INFORMATION: Primer Eo7-11R

<400> SEQUENCE: 26
ttggcaccca cactctgata                                          20

<210> SEQ ID NO 27
<211> LENGTH: 20
<212> TYPE: DNA
<213> ORGANISM: Artificial sequence
<220> FEATURE:
<223> OTHER INFORMATION: Primer Eo7-12F

<400> SEQUENCE: 27
accagtccgg tgctgtttac                                          20

<210> SEQ ID NO 28
<211> LENGTH: 23
<212> TYPE: DNA
<213> ORGANISM: Artificial sequence
<220> FEATURE:
<223> OTHER INFORMATION: Primer Eo7-12R

<400> SEQUENCE: 28
tcccayacac arttytgcca gtc                                      23

<210> SEQ ID NO 29
<211> LENGTH: 23
<212> TYPE: DNA
<213> ORGANISM: Artificial sequence
<220> FEATURE:

<210> SEQ ID NO 30
<211> LENGTH: 27
<212> TYPE: DNA
<213> ORGANISM: Artificial sequence
<220> FEATURE:
<223> OTHER INFORMATION: Primer Eo7-13F

<400> SEQUENCE: 29
caraaytgtg tgtgggaaga cta                                    23

<210> SEQ ID NO 30
<211> LENGTH: 27
<212> TYPE: DNA
<213> ORGANISM: Artificial sequence
<220> FEATURE:
<223> OTHER INFORMATION: Primer Eo7-13R

<400> SEQUENCE: 30
ccctgytcca tkgcttcatc ytcyarc                                27

<210> SEQ ID NO 31
<211> LENGTH: 20
<212> TYPE: DNA
<213> ORGANISM: Artificial sequence
<220> FEATURE:
<223> OTHER INFORMATION: Primer Eo7-14F

<400> SEQUENCE: 31
ttacccagtc accttcgagg                                        20

<210> SEQ ID NO 32
<211> LENGTH: 20
<212> TYPE: DNA
<213> ORGANISM: Artificial sequence
<220> FEATURE:
<223> OTHER INFORMATION: Primer Eo7-14R

<400> SEQUENCE: 32
tgtttttcct tcacttccgg                                        20

<210> SEQ ID NO 33
<211> LENGTH: 27
<212> TYPE: DNA
<213> ORGANISM: Artificial sequence
<220> FEATURE:
<223> OTHER INFORMATION: Primer Eo7-15F
<220> FEATURE:
<221> NAME/KEY: misc_feature
<222> LOCATION: (16)..(16)
<223> OTHER INFORMATION: n = any nucleotide

<400> SEQUENCE: 33
gttrgargat gatgcnatgg arcargg                                27

<210> SEQ ID NO 34
<211> LENGTH: 23
<212> TYPE: DNA
<213> ORGANISM: Artificial sequence
<220> FEATURE:
<223> OTHER INFORMATION: Primer Eo7-15R

<400> SEQUENCE: 34
tcaatacggy rtttgswctt gaa                                    23

<210> SEQ ID NO 35
<211> LENGTH: 20
<212> TYPE: DNA
<213> ORGANISM: Artificial sequence
<220> FEATURE:
<223> OTHER INFORMATION: Primer Eo7-16F

<400> SEQUENCE: 35
cctytrtayg cvgcygargc                                              20

<210> SEQ ID NO 36
<211> LENGTH: 23
<212> TYPE: DNA
<213> ORGANISM: Artificial sequence
<220> FEATURE:
<223> OTHER INFORMATION: Primer Eo7-17F

<400> SEQUENCE: 36
ttcaagwsca aayrccgtat tga                                          23

<210> SEQ ID NO 37
<211> LENGTH: 23
<212> TYPE: DNA
<213> ORGANISM: Artificial sequence
<220> FEATURE:
<223> OTHER INFORMATION: Primer Eo7-16R

<400> SEQUENCE: 37
aaytgaatgg cctthccaca cac                                          23

<210> SEQ ID NO 38
<211> LENGTH: 23
<212> TYPE: DNA
<213> ORGANISM: Artificial sequence
<220> FEATURE:
<223> OTHER INFORMATION: Primer Eo7-18F
<220> FEATURE:
<221> NAME/KEY: misc_feature
<222> LOCATION: (21)..(21)
<223> OTHER INFORMATION: n = any nucleotide

<400> SEQUENCE: 38
ctdgtgtgtg graaggcyat nca                                          23

<210> SEQ ID NO 39
<211> LENGTH: 23
<212> TYPE: DNA
<213> ORGANISM: Artificial sequence
<220> FEATURE:
<223> OTHER INFORMATION: Primer Eo7-18R

<400> SEQUENCE: 39
tatgctccyt graarcctgc aaa                                          23

<210> SEQ ID NO 40
<211> LENGTH: 20
<212> TYPE: DNA
<213> ORGANISM: Artificial sequence
<220> FEATURE:
<223> OTHER INFORMATION: Primer Eo7-19F

<400> SEQUENCE: 40
caagccctaa ccacgtttgt                                              20

<210> SEQ ID NO 41
<211> LENGTH: 20
<212> TYPE: DNA
<213> ORGANISM: Artificial sequence
<220> FEATURE:
<223> OTHER INFORMATION: Primer Eo7-19R

<400> SEQUENCE: 41
acccgtagtc agtcacctgg                                              20

```
<210> SEQ ID NO 42
<211> LENGTH: 23
<212> TYPE: DNA
<213> ORGANISM: Artificial sequence
<220> FEATURE:
<223> OTHER INFORMATION: Primer Eo7-20F

<400> SEQUENCE: 42
tttgcaggmt tycarggwgc ata                                            23

<210> SEQ ID NO 43
<211> LENGTH: 23
<212> TYPE: DNA
<213> ORGANISM: Artificial sequence
<220> FEATURE:
<223> OTHER INFORMATION: Primer Eo7-20R

<400> SEQUENCE: 43
gcyctwgtgg graagttrta cat                                            23

<210> SEQ ID NO 44
<211> LENGTH: 20
<212> TYPE: DNA
<213> ORGANISM: Artificial sequence
<220> FEATURE:
<223> OTHER INFORMATION: Primer Eo7-21F

<400> SEQUENCE: 44
gtgttggatg ccaaggaact                                                20

<210> SEQ ID NO 45
<211> LENGTH: 20
<212> TYPE: DNA
<213> ORGANISM: Artificial sequence
<220> FEATURE:
<223> OTHER INFORMATION: Primer Eo7-21R

<400> SEQUENCE: 45
atgggctccg atctgatgtc                                                20

<210> SEQ ID NO 46
<211> LENGTH: 26
<212> TYPE: DNA
<213> ORGANISM: Artificial sequence
<220> FEATURE:
<223> OTHER INFORMATION: Primer Eo7-22F

<400> SEQUENCE: 46
ttccccacwa grgcaggcca rtgygg                                         26

<210> SEQ ID NO 47
<211> LENGTH: 23
<212> TYPE: DNA
<213> ORGANISM: Artificial sequence
<220> FEATURE:
<223> OTHER INFORMATION: Primer Eo7-22R

<400> SEQUENCE: 47
ctccaaaaba srtcygggtc rca                                            23

<210> SEQ ID NO 48
<211> LENGTH: 20
<212> TYPE: DNA
<213> ORGANISM: Artificial sequence
<220> FEATURE:
<223> OTHER INFORMATION: Primer Eo7-23F
```

<400> SEQUENCE: 48
tgaaggaatg catggacaaa　　　　　　　　　　　　　　　　　　　　　20

<210> SEQ ID NO 49
<211> LENGTH: 20
<212> TYPE: DNA
<213> ORGANISM: Artificial sequence
<220> FEATURE:
<223> OTHER INFORMATION: Primer Eo7-23R

<400> SEQUENCE: 49
atgggtattg ctcatctgcc　　　　　　　　　　　　　　　　　　　　　20

<210> SEQ ID NO 50
<211> LENGTH: 23
<212> TYPE: DNA
<213> ORGANISM: Artificial sequence
<220> FEATURE:
<223> OTHER INFORMATION: Primer Eo7-24F

<400> SEQUENCE: 50
tgygacccrg aystvttttg gag　　　　　　　　　　　　　　　　　　　23

<210> SEQ ID NO 51
<211> LENGTH: 22
<212> TYPE: DNA
<213> ORGANISM: Artificial sequence
<220> FEATURE:
<223> OTHER INFORMATION: Primer Eo7-24R

<400> SEQUENCE: 51
tcrtgdatdt cyttcatggg ca　　　　　　　　　　　　　　　　　　　22

<210> SEQ ID NO 52
<211> LENGTH: 20
<212> TYPE: DNA
<213> ORGANISM: Artificial sequence
<220> FEATURE:
<223> OTHER INFORMATION: Primer Eo7-25F

<400> SEQUENCE: 52
cctggacgaa tgtgaccttt　　　　　　　　　　　　　　　　　　　　　20

<210> SEQ ID NO 53
<211> LENGTH: 20
<212> TYPE: DNA
<213> ORGANISM: Artificial sequence
<220> FEATURE:
<223> OTHER INFORMATION: Primer Eo7-25R

<400> SEQUENCE: 53
ccctaccgca cttttatcca　　　　　　　　　　　　　　　　　　　　　20

<210> SEQ ID NO 54
<211> LENGTH: 23
<212> TYPE: DNA
<213> ORGANISM: Artificial sequence
<220> FEATURE:
<223> OTHER INFORMATION: Primer Eo7-26F

<400> SEQUENCE: 54
atccaygart chatyagrtg gac　　　　　　　　　　　　　　　　　　　23

<210> SEQ ID NO 55

```
<211> LENGTH: 24
<212> TYPE: DNA
<213> ORGANISM: Artificial sequence
<220> FEATURE:
<223> OTHER INFORMATION: Primer Eo7-26R

<400> SEQUENCE: 55
ccgcaccgaa tgcggagaat ttac                                              24
```